US007342101B1

(12) United States Patent
Cox et al.

(10) Patent No.: US 7,342,101 B1
(45) Date of Patent: Mar. 11, 2008

(54) COMPOSITIONS AND METHODS COMPRISING A PROTECTIVE ANTIGEN OF COCCIDIODES IMMITIS

(75) Inventors: Rebecca A. Cox, San Antonio, TX (US); D. Mitchell Magee, Dallas, TX (US); F. Douglas Ivey, Watertown, MA (US); Melanie D. Woitaske, La Vernia, TX (US)

(73) Assignee: The University of Texas System Board of Regents, Austin, TX (US)

( * ) Notice: Subject to any disclaimer, the term of this patent is extended or adjusted under 35 U.S.C. 154(b) by 66 days.

(21) Appl. No.: 10/985,853

(22) Filed: Nov. 10, 2004

Related U.S. Application Data

(60) Provisional application No. 60/526,105, filed on Dec. 1, 2003.

(51) Int. Cl.
  *C07K 1/00* (2006.01)
  *C07K 16/00* (2006.01)
  *C12P 21/08* (2006.01)
  *C07H 21/04* (2006.01)
  *A61K 39/00* (2006.01)
  *A61K 38/00* (2006.01)
(52) U.S. Cl. .................. 530/350; 530/388.6; 530/300; 536/23.2; 536/24.2; 424/184.1
(58) Field of Classification Search ................ 530/300, 530/388.6, 350; 424/184.1; 536/23.2, 24.2
See application file for complete search history.

(56) References Cited

U.S. PATENT DOCUMENTS

| 5,284,747 A | 2/1994 | Milliman ........................ 435/6 |
| 5,622,827 A | 4/1997 | McAllister et al. ............ 435/6 |
| 5,703,057 A | 12/1997 | Johnston et al. .............. 514/44 |
| 5,837,734 A | 11/1998 | Bartsch et al. .............. 514/594 |
| 5,989,553 A | 11/1999 | Johnston et al. ......... 424/190.1 |
| 2003/0219455 A1 | 11/2003 | Cole et al. .............. 424/190.1 |
| 2003/0224013 A1 | 12/2003 | Cole et al. .............. 424/191.1 |
| 2004/0001843 A1 | 1/2004 | Galgiani et al. ........... 424/185.1 |
| 2004/0181046 A1* | 9/2004 | Cole et al. ................. 536/23.1 |

OTHER PUBLICATIONS

Cox et al (Valley Fever Vaccine Development, a progress report for Jul. 2002 through Dec. 30, 2002, Meeting held on Dec. 1, 2002).*
Ivey et al (Identification of a protective antigen of *Coccidioides immitis* by expression library immunization, Vaccine, Oct. 1, 2003; 21(27-30): 4359-4367).*
Peng et al (Localization within a proline-rich antigen (Ag2/PRA) of protective antigenicity against infection *Coccidioides immitis* in mice, Infection and Immunity, 2002; 70(7): 3330-3335).*
Kirkland et al (Evaluation of the Proline-rich antigen of *Coccidioides immitis* as a vaccine candidate in mice, Infection and Immunity, 1998; 66(8): 3519-3522).*

Abuodeh et al., "Resistance to *Coccidioides Immitis* in Mice after Immunization with Recombinant Protein or a DNA Vaccine of a Proline-Rich Antigen," *Infect. Immun.*, 67(6):2935,2940, 1999.
Ampel et al., "In vitro Assessment of Cellular Immunity in Human Coccidioidomycosis: Relationship Between Dermal Hypersensitivity, Lymphocyte Transformation, and Lymphocyte Production by Peripheral Blood Mononuclear Cells from Healthy Adults," *J. Infect. Dis.*, 165:710-715, 1992.
Barry et al., "Protection Against Mycoplasma Infection Using Expression-Library Immunization", *Nature*, 377(6550):632-635, 1995.
Billetta et al., "A Novel Antigen from *Coccidioides Immitris* Identified by Expression Library Immunization (ELI)," *Immunol. Letts.*, 73(2-3):269, 2000, Abstract = 794.
Billetta et al., "Identification of a Novel Antigen from *Coccidiodes Immitis* Using Immuno-Based Functional Genomic Methods," *The Midwinter Conference of Immunologists*, Jan. 22-25, 2000.
Burgess et al., "Possible Dissociation of the Heparin-Binding and Mitogenic Activities of Heparin-Binding (Acidic Fibroblast) Growth Factor-1 from its Receptor-Binding Activites by Site-Directed Mutagenesis of a Single Lysine Residue," *J. Cell Biol.*, 111:2129-2138, 1990.
Corry et al., "Cytokine Production by Peripheral Blood Monouclear Cells in Human *Coccidiodomycosis*," *J. Infect. Dis.*, 174:440-443, 1996.
Cox and Magee, "*Coccidiodomycosis*: Host Response and Vaccine Development," *Clin. Microbiol. Rev.*, 17(4):804-839, 2004.
Cox et al., "Valley Fever Vaccine Development," Progress Report submitted to California State Bakersfield Foundation, Valley Fever Vaccine Project Meeting, Report for Period Jul. 2002-Dec. 30, 2002. Meeting held Dec. 1, 2002.
Cox and Magee, "Vaccine Efficacy of *Coccidioides Immitis* Antigen 2," Progress Report submitted to California State Bakersfield Foundation, Valley Fever Vaccine Project Meeting, Report for Period Jul. 1, 2000-Dec. 31, 2000. Meeting held Dec. 4-5, 2000.
Cox and Magee, "Vaccine Efficacy of *Coccidioides Immitis* Antigen 2," Progress Report submitted to California State Bakersfield Foundation, Valley Fever Vaccine Project Meeting, Report for Period Jan. 1, 1998-Dec. 31, 1999. Meeting held Feb. 22-23, 2000.
Cox and Magee, "Vaccine Efficacy of *Coccidioides Immitis* Antigen 2," Progress Report submitted to California State Bakersfield Foundation, Valley Fever Vaccine Project Meeting, Report for Period Jan. 1, 2000-Jun. 31, 2000. Meeting held Jun. 13-14, 2000.

(Continued)

*Primary Examiner*—Robert A. Zeman
*Assistant Examiner*—Lakia J Tongue
(74) *Attorney, Agent, or Firm*—Myers Bigel Sibley & Sajovec, P.A.

(57) ABSTRACT

Disclosed are protein and peptide antigen and DNA compositions effective in generating immune responses against the pathogenic fungi *Coccidioides* spp., the causative agents of coccidioidomycosis and Valley Fever. The invention thus provides protein and peptide antigens, DNA constructs, combinations and related biological compositions, and prophylactic and therapeutic methods of using such components and combinations to generate effective and protective immune responses against *Coccidioides* spp., including *C. immitis*.

9 Claims, 7 Drawing Sheets

OTHER PUBLICATIONS

Cox and Magee, U.S. Appl. No. 60/178,571; Entitled "Use of DNA and Expressed Protein as a Vaccine Against Coccidioidomycosis"; by Rebecca A. Cox and D. Mitchell Magee; filed Jan. 28, 2000.

Cox and Magee, "Protective Immunity in *Coccidioidomycosis*," *Res. Immunology*, 149:417-428, 1998.

Delgado et al., "A Recombinant β-1,3-Glucanosyltransferase Homolog of *Coccidioides posadasii* Protects Mice against *Coccidioidomycosis*," *Infect. Immunol.*, 71(6):3010-3019, 2003.

Dolan and Cox, "Production and Characterization of a Monoclonal Antibody to the Complement Fixation Antigen of *Coccidioides Immitis*," *Infect. Immun.*, 59(6):2175-2180, 1991.

Dugger et al., "Cloning and Sequence Analysis of the cDNA for a Protein from *Coccidioides Immitis* with Immunogenic Potential," *Biochem. Biophys. Res. Comm.*, 218:485-489, 1996.

Franco et al., "An Immunodominant Cytotoxic T Cell Epitope on the VP7 Rotavirus Protein Overlaps the H2 Signal Peptide," *J. Gen. Virol.*, 74:2579-2586, 1993.

Hombach et al., "Strictly Transporter of Antigen Presentation (TAP)-Dependent Presentation of an Immunodominant Cytotoxic T Lymphocyte Epitope in the Signal Sequence of a Virus Protein," *J. Exp. Med.*, 182:1615-1619, 1995.

Ivey et al., "Identification of a Protective Antigen of *Coccidioides Immitis* by Expression Library Immunization," *Vaccine*, 21:4359-4367, 2003.

Jiang et al., "Genetic Vaccination Against *Coccidioides Immitis*: Comparison of Vaccine Efficacy of Recombinant Antigen 2 and Antigen 2 cDNA," *Infect. Immun.*, 67(2):630-635, 1999.

Jiang et al., "Coadministration of Interleukin 12 Expression Vector with Antigen 2 cDNA Enhances Induction of Protective Immunity Against *Coccidioides Immitis*," 67(11):5848-5853, 1999.

Jobling and Holmes,"Analysis of Structure and Function of the B Subunit of Cholera Toxin by the Use of Site-Directed Mutagenesis," *Mol. Microbiol.*, 5:1755-67, 1991.

Kirkland et al., "Evaluation of the Proline-Rich Antigen of *Coccidioides Immitis* as a Vaccine Candidate in Mice," *Infect. Immun.*, 66(8):3519-3522, 1998.

Kondo et al., "A Single Retroviral Gag Precursor Single Peptide Recognized by FBL-3 Tumor-Specific Cytotoxic T. Lymphocytes," *J. Virol.*, 69(11):6735-6741, 1995.

Lazar et al.,"Transforming Growth Factor α Mutation of Aspartic Acid 47 and Leucine 48 Results in Different Biological Activities," *Mol. Cell Biol.*, 8(3):1247-1252, 1988.

Li et al., "Recombinant Urease and Urease DNA of *Coccidioidomycosis Immitis* Elicit and Immunoproteactive Response Against *Coccidiodomycosis* in Mice," *Infect Immun.*, 69(5):2878-87, 2001.

Magee, Presented the *Ci*-ELI-AGl Data at the 15th Congress of the International Scoiety for Human and Animal Mycology, San Antonio, Texas, May 25-29, 2003.

Pan and Cole, "Molecular and Biochemical Characterization of a *Coccidioides Immitis*-Specific Antigen," *Infect. Immun.*, 63(10):3994-4002, 1995.

Rudinger, "Characteristics of the Amino Acids as Components of a Peptide Hormone Sequence," In 'Peptide Hormones', edited by Parsons, J.A., University Park Press, Jun. 1976, p. 6.

Stevens, "Current Concepts: *Coccidioidomycosis*," *N. Eng. J. Med.*, 332:1077-1082, 1995.

Yu et al., "Isolation and Characterization of the Urease Gene (URE) from the Pathogenic Fungus, *Coccidioides Immitis*," *Gene*, 198(1-2):387-91, 1997.

Zhu et al., "Identification of a *Coccidioides Immitis* Antigen 2 Domain That Expresses B-Cell Reactive Epitopes,"*Infect. Immun.*, 65(8):3376-3380, 1997.

Zhu et al., "*Coccidioides Immitis* Antigen 2: Analysis of Gene and Protein," *Gene*, 181:121-125, 1996.

Zhu et al., "Molecular Cloning and Characterization of *Coccidioides Immitis* Antigen 2 cDNA," *Infect. Immun.*, 64(7):2695-2699, 1996.

Accession No. U39835.

Accession N. U325181.

U.S. Appl. No. 10/417,923; Entitled: "Peptides and DNA Encoding the Peptides Useful for Immunizations Against *Coccidioides* SPP. Infections,"by John N. Galgiani, Kris Orsborn, Tao Peng and Lisa Shubitz; filed Apr. 16, 2003, claiming priority to U.S. Appl. No. 60/373,635, filed Apr. 19, 2002.

U.S. Appl. No. 10/081,935; Entitled "Peptide and DNA Immunization Against *Coccidioides Immitis* Infections"; by Cox, Magee and Jiang; filed: Feb. 22, 2002; claiming priority to U.S. Appl. No. 60/271,031; filed: Feb. 22, 2001.

\* cited by examiner

COMPOSITIONS AND METHODS COMPRISING A PROTECTIVE ANTIGEN OF COCCIDIODES IMMITIS

The present application claims priority to now abandoned U.S. provisional application Ser. No. 60/526,105, filed Dec. 1, 2003, the disclosure of which application, including the specification, claims, drawings and sequence listing, is specifically incorporated herein by reference without disclaimer.

BACKGROUND OF THE INVENTION

1. Field of the Invention

The present invention relates generally to the fields of pathogenic fungi and immunology. More particularly, the invention provides compositions of protein and peptide antigens, and genetic constructs expressing the protein and peptide antigens, and methods of using such compositions in generating effective immune responses against pathogenic *Coccidioides* spp. fungi, such as *C. immitis*. The compositions, combinations and methods of the invention are useful in prophylactic and therapeutic applications to combat coccidioidomycosis and Valley Fever, the diseases caused by *Coccidioides* spp. infection.

2. Description of Related Art

An estimated 100,000 persons each year contract coccidioidomycosis, also known as Valley Fever, following infection with pathogenic fungi. The saprobic phase of the etiologic agent, *Coccidioides immitis*, is geographically limited to the soil in the semi-arid regions of southwestern United States, including parts of Texas, California, Nevada, Utah, Arizona and New Mexico, parts of Mexico and in other countries in Central and South America, where it propagates in the soil in a mycelial phase which produces arthroconidia (Pappagionis, 1980). Within *Coccidioides* spp., *C. immitis* was first described, and is now becoming known as the Californian population. *C. immitis* is classified as a Select Agent. The *C. posadasii* species was recently defined, and was previously recognized as the non-Californian population of *C. immitis* (Fisher et al., 2002).

The *Coccidioides* spp. organisms grow in the soil and, following winter rains, produce arthroconidia. Primary infection is acquired via inhalation of the arthroconidia, which become airborne when the soil is disturbed. Following inhalation, the arthroconidia undergo a morphogenic conversion into endosporulating spherules. *Coccidioides* spp. infection causes disease in dogs and cats, amongst other mammals.

In humans, the majority of persons who acquire primary infection with this fungus manifest a benign or asymptomatic infection; however, others can go on to develop an acute or chronic disease involving the lungs and/or extrapulmonary organs (Galgiani, 1993). The coccidioidomycosis disease, or Valley Fever, can develop into a disseminated process involving virtually any organ in the body, with the exception of the gastrointestinal tract. Although there is not a genetic predisposition to acquiring primary coccidioidomycosis, persons of Asian, African-American or Hispanic descent are predisposed to developing disseminated disease (Pappagianis, 1980; Galgiani, 1993, Kirkland and Cole, 2002). Other high risk groups include pregnant females, older persons, and those who are immunocompromised. The morbidity and mortality of the disease causes problems for those living in the relevant geographical areas.

Certain methods are available to treat coccidioidomycosis in mammals, including systemic anti-fungal therapies. In humans, the available treatment methods are limited by problems of patient tolerance and drug resistance. The development of preventative measures is preferred over methods to treat the infection once it has occurred. The need for effective immunization strategies is further emphasized by increased travel and urbanization of the endemic areas. Thus, coccidioidomycosis is a prime candidate for vaccine development (Cox and Magee, 2004).

On the basis of the preceding, a vaccine for coccidioidomycosis would target persons residing in endemic regions, with emphasis on those who have occupational exposure to the soil, e.g. farmers, construction workers, archeologists, and persons who are genetically predisposed to developing progressive, disseminated coccidioidomycosis. In addition, military personnel training in endemic areas and retirees relocating to endemic areas would be targets for the vaccine.

A series of investigations have established that cell-mediated immune responses are important to host defense against *C. immitis* (Beaman et al., 1979; 1987; Magee and Cox, 1995; 1996; Ampel and Christian, 1997; Cox and Magee, 1998). Recovery from primary, uncomplicated infection is associated with life-long resistance to the disease (Pappagianis and Levine, 1975; Pappagianis, 1980; Galgiani, 1993; Cox and Magee, 1998) and is accompanied by the acquisition of delayed-type hypersensitivity and the production of T-helper 1 associated cytokines, such as IFN-γ and IL-2 (Levine et al., 1970; Pappagianis and Levine, 1975; Cox and Magee, 1998; Kirkland and Cole, 2002). Conversely, persons with chronic or progressive disease manifest low to nondemonstrable levels of cell-mediated immunity to *C. immitis* antigens, but high levels of anti-*Coccidioides* antibodies. The acquired immunity that develops after active infection documents the feasibility of a vaccine for this disease.

Early studies by Levine and co-workers established that formalin-killed spherules (FKS) engendered protection in mice and monkeys against pulmonary challenge with lethal challenge with *C. immitis* arthroconidia (Levine et al., 1960; 1962; 1970; Pappagianis et al., 1961; Kong et al., 1963). The protection in mice was accompanied by the induction of cell-mediated immune responses and could be adoptively transferred by splenic T cells, but not by B cells or serum from immunized donors (Beaman et al., 1979; Cox and Magee, 1998). A large, double-blind Phase 3 study of the FKS vaccine was conducted in skin-test negative persons residing in endemic areas in California and Arizona (Pappagianis and Levine, 1975). A slight, but statistically insignificant reduction was observed in the FKS-vaccinated versus placebo group. The low efficacy of the FKS vaccine in humans has been attributed to the low dose dictated by the toxicity of the killed spherule preparation.

The discouraging results obtained with the FKS vaccine prompted investigators to identify the protective component(s) of killed spherules for use as subunit vaccines. Promising results have been reported with an alkali-soluble, water-soluble spherule cell wall fraction which contains Antigen 2 (Ag2) (Lecara et al., 1983), a 27K fraction obtained from mechanically-disrupted spherules (Zimmermann et al., 1998), and a spherule outer wall (SOW) fraction (Kirkland et al., 1998; Hung et al., 2000). Although the 27K fraction induced protection comparable to that obtained with the FKS vaccine, the 27K fraction suffers from the drawback of being antigenically heterogeneous, essentially containing the spectrum of antigens present in spherule-phase cells and, as yet, the protective immunogen(s) has not been identified.

The genes that encode Ag2 (Zhu et al., 1996; Jiang et al., 1999a), a proline-rich antigen (PRA) (Dugger et al., 1996;

Jiang et al., 1999a) that has identity to Ag2 (now designated Ag2/PRA), an SOW glycoprotein (Kirkland et al., 1995; Kirkland and Cole, 2002), urease (Li et al., 2001), and a T cell-reactive protein (TCRP) (Kirkland and Cole, 2002) have been cloned and reported to induce protective responses when given as individual DNA and/or recombinant protein vaccines. While these putative vaccine candidates induce protection, they are typically not as protective as FKS or the 27K fraction. Accordingly, there remains in the art a need to identify new antigens that generate effective immune responses against *Coccidioides* spp.

SUMMARY OF THE INVENTION

The present invention addresses the long felt needs in the art by providing new protein, peptide, antigen and nucleic acid compositions from *Coccidioides* spp. for prophylactic and therapeutic uses. The invention particularly concerns compositions based upon the protective antigen termed ELI-Ag1, and methods of using such compositions in generating effective and protective immune responses against *Coccidioides* spp. fungi. The invention thus provides a range of compositions, kits and combinations comprising such proteins, peptides, antigens and genetic constructs and methods of using these agents to prevent, reduce or treat *Coccidioides* spp. infections, coccidioidomycosis and Valley Fever in animals and humans.

The invention particularly relates to isolated or purified proteins and peptides with sequences based upon the ELI-Ag1 discovered herein, and nucleic acid constructs encoding such sequences. Methods, uses and medicaments involving the application of such proteins and peptides and genetic constructs in the immunization against *Coccidioides* spp. fungi and the prevention and treatment of related diseases and conditions are particularly provided.

In exemplary embodiments, the isolated and/or purified proteins and peptides of the invention, and the nucleic acid sequences that encode such proteins and peptides, have defined sequences that substantially correspond to (or encode), or are derived from, the amino acid sequence of SEQ ID NO:2, including conservative amino acid substitutions thereof. Such proteins and the corresponding DNA sequences were herein discovered to be surprisingly effective in eliciting protective immune responses against *Coccidioides* spp.

In certain embodiments, the compositions and isolated nucleic acid segments comprise at least a first isolated coding region that encodes a first protein comprising an amino acid sequence "essentially as set forth in" the amino acid sequence of SEQ ID NO:2. Such as a protein that comprises an amino acid sequence that is at least about 90% identical to amino acids 20-224 of the amino acid sequence of SEQ ID NO:2, or a protein that comprises an amino acid sequence that is at least about 90% identical to the amino acids of SEQ ID NO:2.

The proteins may also be defined as comprising an amino acid sequence that is at least about 91%, 92%, 93%, 94%, 95%, 96%, 97%, 98% or about 99% identical to the amino acids of SEQ ID NO:2. The proteins may further be defined as comprising an amino acid sequence of SEQ ID NO:2 with conservative amino acid substitutions. In other embodiments, the encoded protein has or consists of the amino acid sequence of SEQ ID NO:2 with conservative amino acid substitutions. In further embodiments, the encoded protein consists of the amino acid sequence of SEQ ID NO:2.

Further aspects of the invention are compositions and isolated nucleic acid segments in which the at least a first isolated coding region comprises a nucleotide sequence essentially as set forth in SEQ ID NO:1. In other embodiments, the at least a first isolated coding region comprises, has or consists of the nucleotide sequence of SEQ ID NO:1.

Other exemplary embodiments concern isolated or purified peptides, e.g., of from 7 to about 50 amino acids in length, which comprise, have or consist of an amino acid sequence essentially as set forth in, or as set forth in, any of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21 or SEQ ID NO:22.

Compositions comprising isolated or purified peptides, e.g., of from 7 to about 50 amino acids in length, which comprise, have or consist of an amino acid sequence essentially as set forth in, or as set forth in, any of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21 or SEQ ID NO:22 are other aspects of the invention. Such compositions may be pharmaceutically acceptable compositions, carriers or diluents. The compositions may also further comprise an adjuvant and/or may further comprise at least a second, distinct purified *Coccidioides* spp. protein, polypeptide or peptide.

Although surprisingly unique in its discovery and effectiveness, the present invention further provides a range of biological components and methods based upon the initial findings. For example, the invention provides proteins, peptides and fusion proteins, and genetic constructs encoding such proteins, peptides and fusion proteins, that are shorter, longer, derivatized and optimized; epitopic core sequences from such peptides; mimetics; fusion proteins involving such peptides and other sequences, such as additional epitopes, targeting sequences and/or endoplasmic reticulum (ER) insertion sequences; formulations of such peptides and constructs with a range of selected adjuvants, including poly(lactide-co-glycolide) (PLG) microparticle adjuvants; and multimers and combinations of such peptides, including those packaged into "multiple antigen peptide (MAP)" constructs using carriers such as a lysine-glycine core.

The mode of administration the protein, peptide and/or genetic vaccine constructs can also be varied and optimized, if desired. Including, for example, changing the amount, route, number and timing of the immunizations, and combining the immunizations with defined adjuvants and other immunogens, optionally in prime and boost embodiments and other combined prophylactic and therapeutic protocols.

All such compositions and methods can be used without undue experimentation in light of the present disclosure. Although particularly useful in vaccination, the ELI-Ag1 protein, peptide and DNA compositions of the invention are further useful in a variety of other embodiments, including as biological tools, for use in binding assays, in diagnosis and even for therapy of other fungal conditions.

In the compositions and isolated nucleic acid segments, the at least a first isolated coding region is preferably positioned under the control of a promoter. Such constructs are therefore further defined as recombinant vectors, which may be comprised within recombinant host cells. The recombinant vectors and host cells preferably express the isolated coding region to produce the encoded peptide or polypeptide. As such, the recombinant vectors are preferably "recombinant expression vectors."

An exemplary composition of the invention is a recombinant vector, or recombinant expression vector, that comprises at least a first isolated coding region that encodes, and preferably expresses, at least a first *C. immitis* protein that comprises the amino acid sequence of amino acids 20-224 of SEQ ID NO:2 with conservative amino acid substitutions. In certain embodiments, the recombinant vector or recombinant expression vector comprises at least a first isolated coding region that encodes, and preferably expresses, at least a first *C. immitis* protein that comprises the amino acid sequence of SEQ ID NO:2 with conservative amino acid substitutions. In other embodiments, the recombinant vector or recombinant expression vector comprises at least a first isolated coding region that encodes, and preferably expresses, at least a first *C. immitis* protein that consists of the amino acid sequence of SEQ ID NO:2 with conservative amino acid substitutions. In further embodiments, the recombinant vector or recombinant expression vector comprises at least a first isolated coding region that encodes, and preferably expresses, at least a first *C. immitis* protein that consists of the amino acid sequence of SEQ ID NO:2.

The nucleic acid segments and recombinant vectors of the invention can further comprise at least a second isolated coding region that encodes a second protein, polypeptide or peptide. The second isolated coding region may encode a second, distinct *Coccidioides* spp. protein, polypeptide or peptide. A "second, distinct" *Coccidioides* spp. protein, polypeptide or peptide means a protein, polypeptide or peptide "distinct from", i.e., in addition to, the peptide encoded by the first isolated coding region. Ag2/PRA(1-18), Ag2/PRA1-106, Ag2/PRA27-106, CSA (or Csa), Ag2-Csa fusion proteins, Gel1 (Gel-1) and urease (Ure) antigens are currently preferred for combination with the ELI-Ag1 of the invention.

Alternatively, the at least a second isolated coding region may encode further copies of the first protein or peptide. Such expression constructs may be used to prepare a plurality of isolated peptides, which can be operatively assembled into a multiple antigen peptide (MAP) construct.

In either of such embodiments, the overall nucleic acid segment may comprise separate first and second isolated coding regions, wherein the first and second proteins, polypeptides or peptides are produced separately from each other, such that they exist as a mixture. In other embodiments, the first and second isolated coding regions are operatively attached, in frame, wherein the overall nucleic acid segment then encodes a fusion protein, in which the first peptide is operatively linked to the second protein, polypeptide or peptide.

Further examples of the nucleic acid segments and recombinant vectors of the invention are those in which the second isolated coding region encodes an adjuvant protein, polypeptide or peptide. Again, the adjuvant may be produced as a separate entity or as a fusion protein with the first protein or peptide.

Yet further examples are wherein the at least a second isolated coding region encodes an endoplasmic reticulum insertion sequence, such as an adenovirus glycoprotein-derived endoplasmic reticulum insertion sequence.

The nucleic acid segments, recombinant vectors and recombinant expression vectors of the invention may be comprised within a composition, such as a buffer and/or diluent. Accordingly, the invention also provides compositions comprising at least a first isolated nucleic acid segment, recombinant vector or recombinant expression vector that comprises at least a first isolated coding region that encodes, and preferably expresses, at least a first *C. immitis* protein that comprises the amino acid sequence of amino acids 20-224 of SEQ ID NO:2 with conservative amino acid substitutions. In certain embodiments, the composition comprises at least a first isolated coding region, recombinant vector or recombinant expression vector that encodes, and preferably expresses, at least a first *C. immitis* protein that comprises the amino acid sequence of SEQ ID NO:2 with conservative amino acid substitutions. In other embodiments, the composition comprises at least a first isolated coding region, recombinant vector or recombinant expression vector that encodes, and preferably expresses, at least a first *C. immitis* protein that consists of the amino acid sequence of SEQ ID NO:2 with conservative amino acid substitutions. In further embodiments, the composition comprises at least a first isolated coding region, recombinant vector or recombinant expression vector that encodes, and preferably expresses, at least a first *C. immitis* protein that consists of the amino acid sequence of SEQ ID NO:2.

Nucleic acid segments, recombinant vectors and recombinant expression vectors of the invention may also be comprised within pharmaceutically acceptable carriers or diluents, such that pharmaceutical compositions or vaccine formulations result. Such compositions may further comprise at least a first adjuvant. An exemplary adjuvant is a poly(lactide-co-glycolide) (PLG) microparticle adjuvant. These pharmaceutical compositions or vaccine formulations preferably comprise an immunologically effective amount of the at least a first isolated nucleic acid segment, recombinant vector or recombinant expression vector.

The recombinant host cells of the present invention may be maintained in vitro, e.g., for recombinant protein, polypeptide or peptide production. Equally, the recombinant host cells could be host cells in vivo, such as results from immunization of an animal or human with a nucleic acid segment of the invention. Accordingly, the recombinant host cells may be prokaryotic or eukaryotic host cells, such as *E. coli*, yeast, insect, mammalian or human host cells. The host cells will often further comprise at least a second isolated coding region that encodes a second protein, polypeptide or peptide, such as a second, distinct *Coccidioides* spp. protein, polypeptide or peptide.

The invention further provides the proteins and peptides encoded by any of the foregoing isolated nucleic acid segments. Such proteins and peptides may be prepared by purification from natural sources; by recombinant expression, including purification following cleavage; and/or by automated synthesis, particularly for smaller peptides.

One example of a protein of the invention is an isolated or purified protein that comprises the amino acid sequence of amino acids 20-224 of SEQ ID NO:2 with conservative amino acid substitutions. In certain embodiments, the protein may comprise the amino acid sequence of SEQ ID NO:2 with conservative amino acid substitutions. In other embodiments, the protein may consist of the amino acid sequence of SEQ ID NO:2 with conservative amino acid substitutions. In further embodiments, the protein may consist of the amino acid sequence of SEQ ID NO:2.

The proteins and peptides of the invention may be comprised within compositions, such as buffers and diluents. Accordingly, the invention provides compositions comprising at least a first isolated or purified *C. immitis* protein that comprises the amino acid sequence of amino acids 20-224 of SEQ ID NO:2 with conservative amino acid substitutions. In certain embodiments, the composition comprises a protein comprising the amino acid sequence of SEQ ID NO:2 with conservative amino acid substitutions. In other embodiments, the composition comprises a protein consisting of the amino acid sequence of SEQ ID NO:2 with conservative amino acid substitutions. In further embodiments, the composition comprises a protein consisting of the amino acid sequence of SEQ ID NO:2.

Proteins and peptides of the invention may also be comprised within a pharmaceutically acceptable carrier or diluent, such that a pharmaceutical composition or vaccine formulation results. These pharmaceutical compositions, antigen compositions or vaccine formulations preferably comprise an immunologically effective amount of the at least a first ELI-Ag1 protein or peptide of the invention. Such as an immunologically effective amount of first purified *C. immitis* protein that comprises the amino acid sequence of amino acids 20-224 of SEQ ID NO:2 with conservative amino acid substitutions, that comprises the amino acid sequence of SEQ ID NO:2 with conservative amino acid substitutions, that consists of the amino acid sequence of SEQ ID NO:2 with conservative amino acid substitutions or that consists of the amino acid sequence of SEQ ID NO:2.

The pharmaceutical composition or vaccine formulations of the invention may optionally further comprise at least a first adjuvant. The adjuvant may be a poly(lactide-co-glycolide) (PLG) microparticle adjuvant, in which case the at least a first isolated peptide may be encapsulated within the PLG microparticles.

In certain embodiments, such compositions will comprise a plurality of isolated ELI-Ag1 peptides operatively assembled into a multiple antigen peptide (MAP) construct, such as linked to a lysine-glycine core.

Antigenic cocktails, multivalent or polypotent vaccines of the invention result wherein the protein, pharmaceutical or antigen compositions or vaccine formulations further comprise a combined immunogenic amount of at least a second *Coccidioides* spp. component. The "at least a second" *Coccidioides* spp. component is typically at least a second immunogenic or antigenic *Coccidioides* spp. component. One example is wherein a composition further comprises at least a second, distinct purified *Coccidioides* spp. protein, polypeptide or peptide, i.e., a second, purified *Coccidioides* spp. protein, polypeptide or peptide "in addition to" the at least a first purified *C. immitis* protein that comprises an amino acid sequence based upon, derived from or comprising SEQ ID NO:2. Ag2/PRA(1-18), Ag2/PRA1-106, Ag2/PRA27-106, CSA, Ag2-Csa fusion proteins, Gel1 and urease antigens are currently preferred as "second" components for combination with the "first", ELI-Ag1 of the invention.

The invention further provides a number of methodological embodiments. For example, methods for generating an immune response, comprising providing to an animal or human an immunologically effective amount of at least a first isolated ELI-Ag1 nucleic acid segment, recombinant vector or recombinant expression vector, or at least a first isolated ELI-Ag1 protein or peptide in accordance with the present invention.

The "immunologically effective amount", as used herein, is typically an amount effective to generate an immune response following administration or provision to an animal or human. For example, an immunologically effective amount of a purified *C. immitis* protein or peptide, or a recombinant vector that expresses such a *C. immitis* protein or peptide, is "an amount effective to generate an immune response against the *C. immitis* protein or peptide following administration or provision to an animal or human".

In certain embodiments, the immunologically effective amount is an amount effective to generate an effective immune response. An "effective immune response", as used herein, is typically a response effective to generate a detectable immune, antibody or T cell response against the *C. immitis* protein or peptide. In further embodiments, the effective immune response is a response effective to suppress, attenuate, inhibit, decrease or even prevent the growth of a *Coccidioides* spp. fungus, such as *C. immitis*, in an animal or human infected with or exposed to the *Coccidioides* spp. fungus, such as *C. immitis*.

The animal or human subject may have, be suspected of having or at risk for developing coccidioidomycosis or Valley Fever. Accordingly, the invention provides methods for treating coccidioidomycosis or Valley Fever, comprising administering to an animal or human having or suspected of having coccidioidomycosis or Valley Fever, a therapeutically effective amount of at least a first isolated ELI-Ag1 nucleic acid segment, recombinant vector or recombinant expression vector, or at least a first isolated ELI-Ag1 protein or peptide in accordance with the present invention. The ELI-Ag1 may comprise the amino acid sequence of amino acids 20-224 of SEQ ID NO:2 with conservative amino acid substitutions, may comprise the amino acid sequence of SEQ ID NO:2 with conservative amino acid substitutions, may consist of the amino acid sequence of SEQ ID NO:2 with conservative amino acid substitutions or may consist of the amino acid sequence of SEQ ID NO:2.

Still further embodiments of the invention are methods for reducing, preventing or vaccinating against coccidioidomycosis or Valley Fever. Such methods comprise administering to an animal or human suspected of having, or at risk for developing, coccidioidomycosis or Valley Fever a pharmaceutically acceptable composition comprising a prophylactically effective amount of at least a first isolated ELI-Ag1 nucleic acid segment, recombinant vector or recombinant expression vector, or at least a first isolated ELI-Ag1 protein or peptide in accordance with the present invention. The ELI-Ag1 may comprise the amino acid sequence of amino acids 20-224 of SEQ ID NO:2 with conservative amino acid substitutions, may comprise the amino acid sequence of SEQ ID NO:2 with conservative amino acid substitutions, may consist of the amino acid sequence of SEQ ID NO:2 with conservative amino acid substitutions or may consist of the amino acid sequence of SEQ ID NO:2.

As with the compositions, in the methods of the invention, at least a second, distinct purified *Coccidioides* spp. protein, polypeptide or peptide, or a recombinant vector that expresses a second, distinct *Coccidioides* spp. protein, polypeptide or peptide, may also be provided to the animal or human. Ag2/PRA(1-18), Ag2/PRA1-106, Ag2/PRA27-106, CSA, Ag2-Csa fusion proteins, Gel1 and urease antigens are currently preferred as "second" components for combination with the "first", ELI-Ag1 of the invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. *Coccidioides* spp. Infections and Disease

Figure 1:
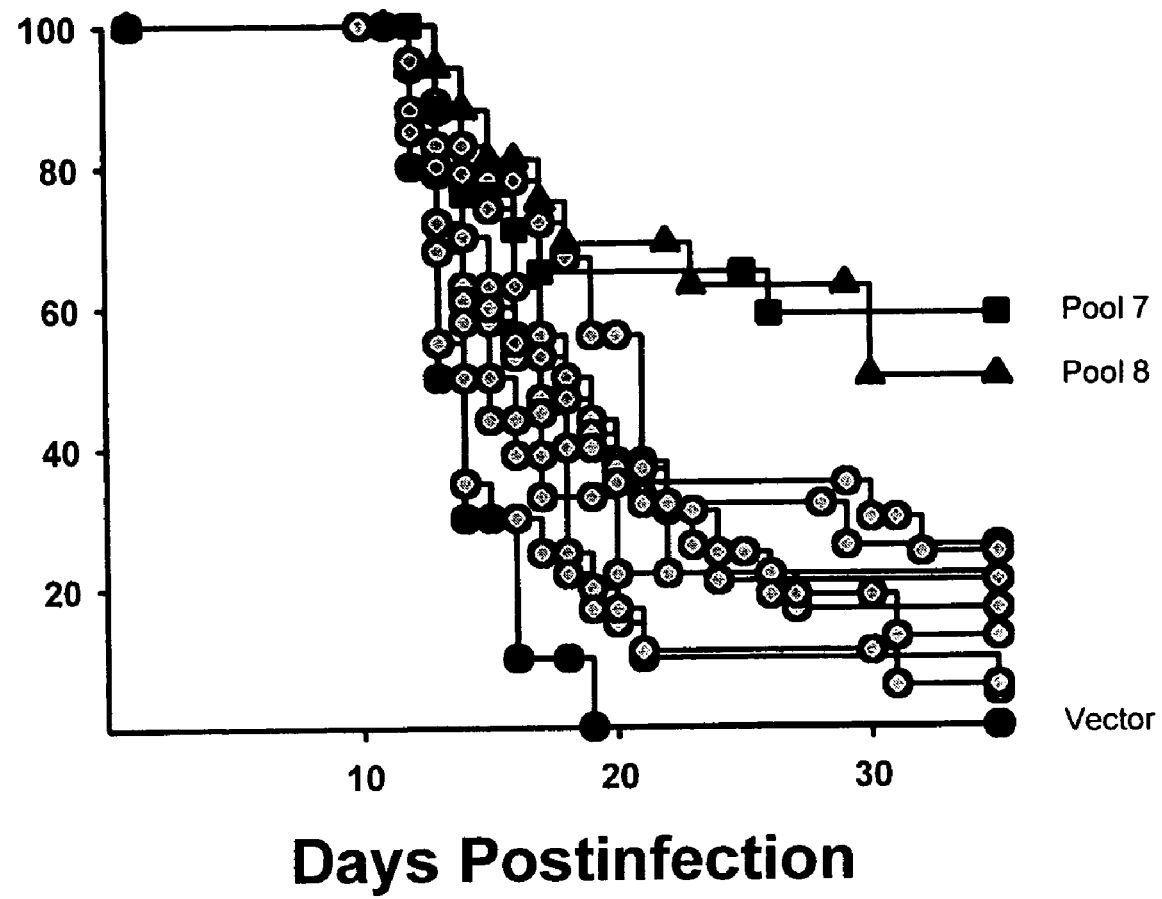
FIG. 1. First-level screening of ELI using Pools 1 through 10, each pool containing 80 to 100 genes. The figure depicts the combined data from two separate studies with a total of 18 or more mice per group. The pBK-CMV vector alone was used as the negative control. The most protective pools, Pool 7 (■) and Pool 8 (▲), and the vector control (●) are depicted using black lines. All other pools are depicted using gray circles.
Figure 2:
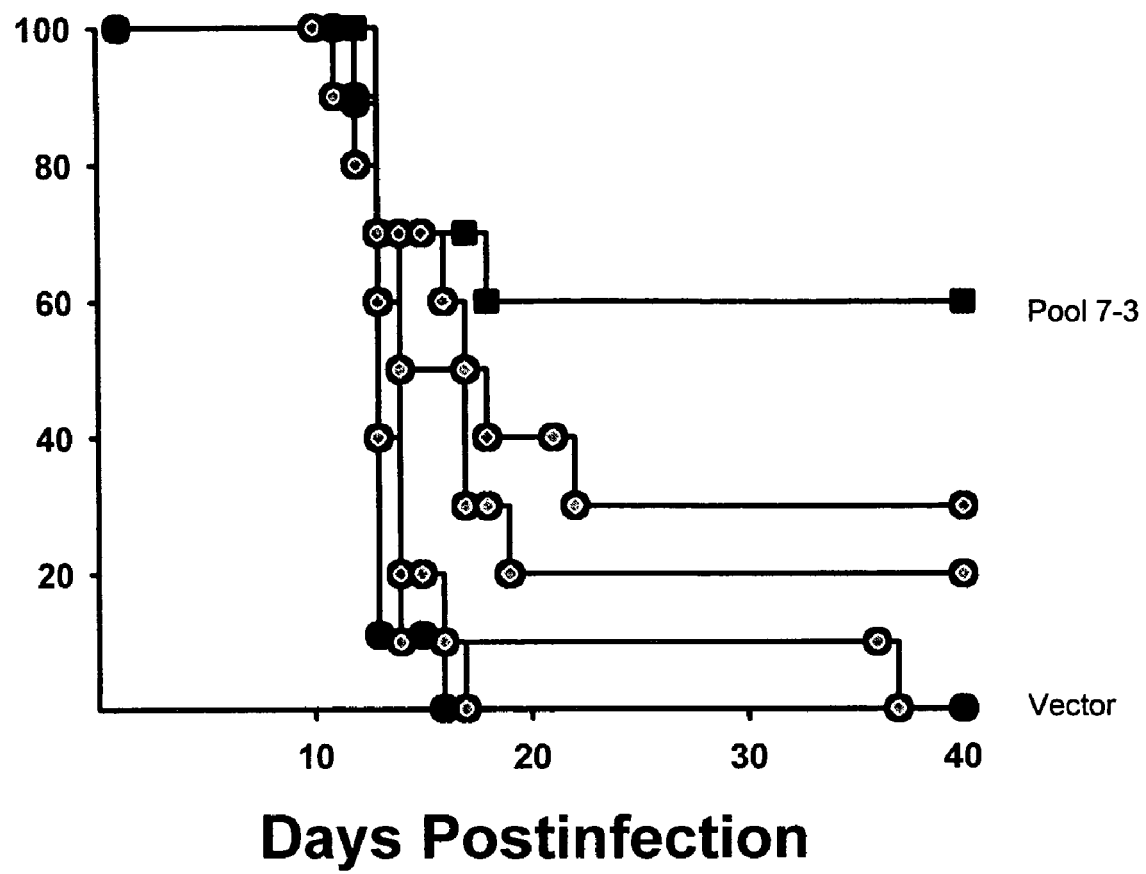
FIG. 2. Second-level screening using five Pool 7-derived sublibraries, each containing 60 genes. The most protective pool, Pool 7-3 (■), and the vector control (●) are depicted using black lines. Pools 7-1, 7-2, 7-4, and 7-5 are depicted using gray circles. Groups of 10 mice were used per pool.
Figure 3:
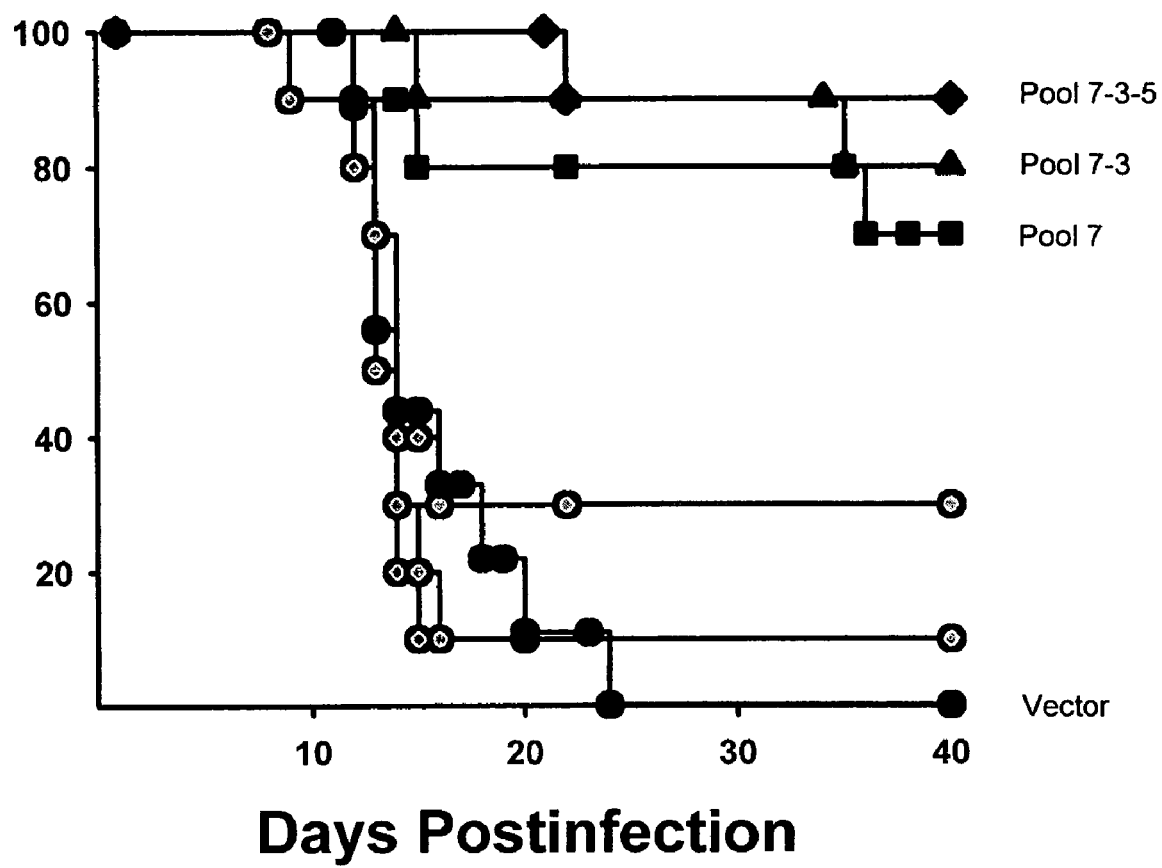
FIG. 3. Third-level screening using six Pool 7-3 derived sublibraries, each containing 10 genes. The most protective pool, Pool 7-3-5 (♦), and for comparisons Pools 7 (■) and 7-3 (▲) from whence Pool 7-3-5 was derived, and the vector control (●) are depicted using black lines. Pool 7-3-1, 7-3-2, 7-3-3, and 7-3-4 are depicted using gray circles. Groups of 10 mice were used per pool.
Figure 4:
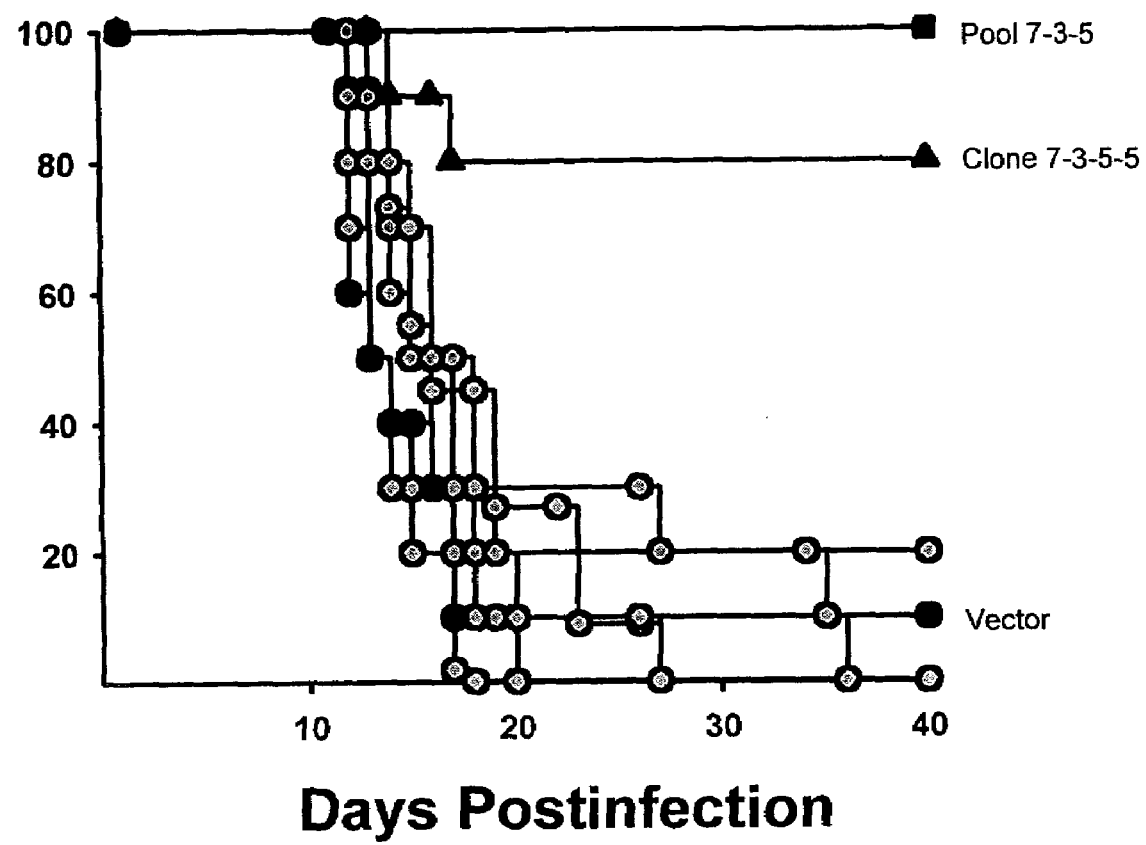
FIG. 4. Fourth-level screening using ten Pool 7-3-5-derived sublibraries, each containing a single clone. The most protective clone, Pool 7-3-5-5 (▲), and for comparison Pool 7-3-5 (■) from whence Pool 7-3-5-5 was derived, and the vector control (●) are depicted using black lines. Pools 7-3-5-1, 7-3-5-2, 7-3-5-3, 7-3-5-4, 7-3-5-6, 7-3-5-7, 7-3-5-8, 7-3-5-9, and 7-3-5-10 are depicted using gray circles. Groups of 10 mice were used per pool.

*Coccidioides* spp., such as *C. immitis* and *C. posadasii*, are geophilic, dimorphic fungi that are endemic to the southwestern United States, parts of Mexico and in Central and South America. Infection with these fungal pathogens causes coccidioidomycosis (San Joaquin Valley Fever), a respiratory disease (Pappagianis, 1980). The incidence of coccidioidomycosis in the southwestern United States sharply increased in the early 1990's as a result of environmental and demographic changes (Pappagianis, 1994).

Primary infection occurs via inhalation of mycelial-phase arthroconidia, which enter the alveoli and undergo a morphogenetic conversion to a parasitic, spherule form of growth. These large spherules (20 to 100 µm) grow, mature and divide internally to produce endospores. When released, the endospores spread the *Coccidioides* spp. infection locally or to distant sites via the lymphatic system or blood. The disease has diverse manifestations, ranging from a benign pulmonary infection to a progressive disseminated disease most commonly involving the skin, bones and/or joints and central nervous system.

Acute, primary pulmonary coccidioidomycosis usually occurs within one to three weeks following *Coccidioides* spp. infection. Early clinical signs may be absent or include a mild nonproductive cough, low-grade fever, partial anorexia, and weight loss. This form of disease is often self-limiting, but may progress to disseminated infection. Disseminated pulmonary coccidioidomycosis causes a more severe productive cough due to widespread lung involvement and tracheobronchial lymphadenopathy. Systemic signs include an antibiotic-unresponsive fluctuating fever, depression, weakness, anorexia, and weight loss. *Coccidioides* spp. may spread beyond the pulmonary tree, affecting any organ or system in the body.

Currently available treatments for coccidioidomycosis include systemic anti-fungal therapies. For example, the imidazoles such as ketoconazole and itraconazole are used for the treatment of coccidioidomycosis in the dog and cat. Liposome-encapsulated amphotericin B has also been shown to be safe and effective in the treatment of coccidioidomycosis in those dogs that cannot tolerate oral imidazole therapy. However, *C. immitis* is more resistant to amphotericin B than the other systemic mycotic agents.

In the clinical arena, problems of patient tolerance and drug resistance exist that limit the currently available treatments. Even if effective treatment strategies could be developed, this only attends to the infected individuals, and does not combat the disease at large. Preventative measures are therefore needed to provide effective immunization against *Coccidioides* spp.

Evidence from clinical and experimental investigations revealed that the severity of coccidioidomycosis directly correlates with depressed cell-mediated immunity to coccidioidal antigens (Beaman et al., 1979; Beaman, 1987; Ampel and Christian, 1997; Cox et al., 1988; Magee and Cox, 1995; 1996; Cox and Magee, 1998). Recovery from primary infection is associated with strong cell-mediated immune responses to *C. immitis* and is accompanied by life-long immunity to exogenous reinfection (Pappagianis and Levine, 1975; Pappagianis, 1980; Galgiani, 1993; Cox, 1993; Stevens, 1995; Cox and Magee, 1998).

Previous vaccine studies using experimental animal models demonstrated that immunization with killed spherules induces protection against pulmonary challenge with a lethal dose of arthroconidia (Levine et al., 1960; 1962; 1970; Kong et al., 1963). Investigations showed that the protective component(s) resided primarily in the cell walls of killed spherules (Kong et al., 1963). A degree of protection has also been observed using other spherule components, including spherule cell wall fractions (Lecara et al., 1983; Zimmermann et al., 1998; Kirkland et al., 1998; Hung et al., 2000), and antigens termed Ag2/PRA (Zhu et al., 1996; Jiang et al., 1999a; Dugger et al., 1996), SOW glycoprotein (Kirkland et al., 1995; Kirkland and Cole, 2002), urease (Li et al., 2001) and TCRP (Kirkland and Cole, 2002).

Although the foregoing studies indicate that developing a vaccine is a feasible and promising strategy against *Coccidioides* spp. in regions endemic to this fungal pathogen, a clinically effective vaccine has yet to be developed. The present inventors therefore reasoned that additional antigens should be sought for use as, or as part of, an effective vaccine.

II. New Antigen, ELI-Ag1

Several studies have been directed towards identifying immunoprotective antigens of *C. immitis* for use in vaccine development. Despite certain advances, additional antigens are still sought after. The inventors consider it likely, if not probable, that a vaccine for inducing optimal resistance will need to be a multicomponent vaccine, and that all components of such a vaccine have yet to be identified.

In searching for additional antigens capable of eliciting effective immune responses against *Coccidioides* spp., the inventors turned to expression library immunization (ELI) (Barry et al., 1995; Billetta et al., 2000; U.S. Pat. Nos. 5,989,553 and 5,703,057, each specifically incorporated herein by reference; see also, Example VII in U.S. application Ser. No. 10/081,935, filed Feb. 22, 2002). This procedure capitalizes on the fact that a pathogen's genomic DNA encodes all of the antigens produced by that pathogen. Hence, by immunizing with sequentially divided protective fractions of a genomic library, the potential of screening every gene in the pathogen's genome is realized. The strategy also offers the advantage of presenting the host with multiple genes, thereby simulating the effects of the live organism in the absence of any risk of infection. Using ELI, protective genes or gene pools have been identified from *Mycoplasma pulmonis* (Barry et al., 1995), *Taenia crassiceps* (Manoutcharian et al., 1998), *Cowdria ruminantium* (Brayton et al., 1998), *Leishmania major* (Piedrafita et al., 1999), *Leishmania donovani* (Melby et al., 2000), *Plasmodium chabaudi* (Wunderlich et al., 2000; Smooker et al., 2000), HIV-1 (Singh et al., 2002), SIV (Sykes et al., 2002) and *Mycoplasma hyopneumoniae* (Moore et al., 2000).

ELI has proven to be a useful strategy for identifying protective gene pools and offers the decided advantage of not requiring a priori knowledge of whether protection is mediated by cell-mediated or humoral immunity. On the basis that cellular immune responses, notably those mediated by T-helper 1 (Th1) cells, are an important component of host defense against *C. immitis*, earlier investigations have focused on screening libraries for T cell reactive components. The present inventors considered, however, that other immune mechanisms, such as cytotoxic T cells or antibodies, contribute to protective immunity. Since genetic immunization can induce virtually all of the immune responses induced by native antigens, the use of a genomic or cDNA expression library provided an important approach for identifying vaccine candidates.

Most investigations using ELI have been performed using genomic DNA. The inventors realized that one problem associated with ELIs using genomic DNA is that many of the DNA fragments may be in the wrong orientation, in which case they would not be expressed properly (Moore et al., 2000). Also, expression libraries prepared from genomic DNA likely contain fragments that represent only a nominal percentage of their ORFs. While genomic DNA offers the advantage of containing all the genes that encode antigens from all stages of a pathogen's life cycle, the present inventors elected to prepare the expression library using spherule-derived cDNA.

Therefore, a modification of the ELI was used in the present invention, whereby the expression library was constructed with cDNA, rather than genomic DNA (Manoutcharian et al., 1998; 2000). The inventors selected the cDNA-ELI strategy because, firstly, it emphasizes those genes that are expressed and/or up-regulated during the parasitic spherule/endospore phase, which is concordant with the increased protective efficacy of spherules over the saprobic mycelial-phase cells (Levine et al., 1960), and secondly, it decreases the complexity of the search by eliminating non-coding sequences. Although one potential limitation of using cDNA is whether the relevant mRNAs are expressed at sufficient levels to be adequately represented in the library, using this modified ELI technique, a new protective antigen for this pathogen was successfully identified. The present invention therefore provides a new vaccine candidate.

In the development of the invention, a *C. immitis* spherule-phase cDNA library containing 800 to 1,000 genes was divided into 10 pools and each was tested for its protective capacity in BALB/c mice against intraperitoneal challenge with 2,500 arthroconidia of this dimorphic fungus. The most protective pool, designated Pool 7, was fractionated into 5 sublibraries, each containing 60 genes, and of these, only Pool 7-3 induced a significant level of protection in mice. Fractionation of Pool 7-3 into 6 sublibraries, each with 10 genes, yielded a single protective fraction, designated Pool 7-3-5. Subsequent fraction of Pool 7-3-5 into 10 sublibraries, each with 1 clone, yielded a clone designated 7-3-5-5 that was highly protective in BALB/c mice. Of the mouse strains examined to date, BALB/c mice are the most susceptible (Kirkland and Fierer, 1983; Cox et al., 1988) and thus provide the art-accepted model of genetically-acquired susceptibility to *C. immitis*.

ELI was thus used effectively to identify a protective antigen from a fungus and the sequential fractionation of the expression library successfully identified the single protective gene, 7-3-5-5. As this *Coccidioides* gene was identified by ELI, the inventors have used the designation ELI-Antigen 1 (ELI-Ag1). The term "ELI-Ag1" is used throughout the present application for simplicity, notwithstanding that various modifications and combinations of this sequence are disclosed herein and will be understood to be encompassed by the claimed invention.

The ELI-Ag1 was sequenced and determined to contain a 672 bp ORF encoding a 224 amino acid protein, which shared 28% identity with 41% of the amino acids in a hypothetical protein (B24B19.340) from the filamentous fungus *Neurospora crassa*. Analyses showed that ELI-Ag1 has a 19 amino acid signal sequence at the N-terminus, a 15 amino acid C-terminal GPI anchor site and several glycosylated sites, suggestive of an outer membrane or cell wall protein. Expression of ELI-Ag1 in a eukaryotic expression system the recombinant protein to be obtained in its native, post-translationally modified form.

First level screening results showed that Pool 8, as well as Pool 7, induced a significant level of protection in BALB/c mice. Studies are in progress to identify the protective component in Pool 8, and other genes in the cDNA library that were not included in the first level screening. The inventors have presently screened only a small fraction of the spherule-derived cDNA library and the present invention focuses only on those pools yielding the greatest protection. Hence, the inventors' studies are being continued to evaluate the vaccine potential of the remaining genes.

The genome of *Coccidioides posadasii*, which is the proposed nomenclature for non-California strains of *C. immitis* (Fisher et al., 2002), is being sequenced and currently has about a 6× coverage (www.tigr.org). A total of 12,695 ORFs are predicted, representing 35% of the genome, and of these ORFs, 9,046 have a minimum length of 500 bp. Once the correct reading frame for the clone 7-3-5-5 had been delineated by the present inventors, sequence homology with a portion of an uncharacterized sequence in the database, termed Contig:1900, was noted. There are three nucleotide changes in the predicted coding regions, which results in one amino acid change in the protein (Val165Ile). Importantly, the existence of the coding sequence and expressed and isolated protein of this invention could not have been determined or predicted absent the functional studies of the present application.

Currently, the physical map of the *C. posadasii* genome is being annotated, based upon homologies with known genes. It is known, however, that homology-based genomic analysis can yield erroneous assignment of gene function (Saunders and Moxon, 1998). Thus, a direct approach towards identifying potential vaccine candidates in the *Coccidioides* genome is needed, namely cloning the ORFs and evaluating their protective capacity. The inventors reason that one way to circumvent this colossal task would be to construct linear expression elements (Sykes and Johnston, 1999), which have PCR™-amplified ORFs linked to a eukaryotic promoter and terminator, and then evaluate the protective efficacy of the linear expression elements by the ELI.

The feasibility of the foregoing approach is validated by the results of the present invention; namely, the isolation of a single protective gene from a pool of approximately 800 to 1000 genes. Some pre-selection criteria could be used in the preparation of the ELI. One strategy that the inventors envision is to target those ORFs that contain signal sequences and GPI anchor sites for initial screening. The rational for this approach is based upon studies with other coccidioidal antigens, showing that protective antigens have been of cell wall origin. Notwithstanding the potential to identify further protective genes and antigens, the present identification of a first protective antigen, ELI-Ag1, represents an important advance in the art.

Knowledge of the mechanism by which ELI-Ag1 protects mice against a lethal challenge with *C. immitis* arthroconidia is not required for those of ordinary skill in the art to practice the present invention and, indeed, the protective mechanism is not yet known. Analyses of the translated protein revealed several regions of antigenicity and potential reactivity with murine MHC Class I or Class II molecules, which would be consistent with reactivity with both B and $CD4^+$ and $CD8^+$ T cells. Other protective antigens of this fungus have been shown to induce a predominant Th1 response and the production of anti-Coccidioides IgG1 and IgG2a antibodies (Kirkland et al., 1995; Zhu et al., 1996; Kirkland et al., 1998; Jiang et al., 1999a; Abuodeh et al., 1999; Hung et al., 2000; Li et al., 2001). Co-administration of the gene encoding the Th1 cytokine IL-12, significantly enhances the vaccine efficacy of Ag2/PRA (Jiang et al., 1999b). The inclusion of IL-12 DNA or recombinant IL-12 is thus contemplated to be useful in conjunction with ELI-Ag1.

As part of the present invention, protection has already been shown in mice challenged with approximately 2,500 arthroconidia administered via an intraperitoneal injection. The natural route of infection with *C. immitis* occurs by inhalation of the arthroconidia. Hence, protection against pulmonary challenge, which is known to be more rigorous than by the intraperitoneal route (Pappagianis et al., 1961), will be important to the recombinant ELI-Ag1 protein and/or gene. When used to protect against challenge by the pulmonary route, modified immunization protocols may be employed. For example, the ELI-Ag1 may be expressed from a plasmid vector that targets ELI-Ag1 coding sequences to the lungs and/or a plasmid vector that stimulates Class I cytotoxic CD8+ T cells may be employed.

In addition to the ELI-Ag1 provided by the present invention, the inventors contemplate certain refinements designed to improve the protein, peptide and genetic vaccines of the invention. For example, in light of the present disclosure, it is now within the skill of the ordinary artisan to refine and optimize various aspects, such as proteins, peptides, fusion proteins, vectors, doses, combinations, vaccination routes, adjuvant formulations and the like, to produce even more effective vaccine compositions and methods in accordance with the present invention.

For example, although various adjuvants are appropriate for use with the present invention, the use of certain selected adjuvants may provide particular advantages in certain embodiments, as will be known those of ordinary skill in the art in light of the present disclosure. Selected adjuvants for use in the delivery of ELI-Ag1 include, e.g., the biodegradable and biocompatible polyester poly(lactide-co-glycolide) (PLG) formulated as microparticles. Such microparticles have been used in humans for many years as suture material and as controlled-release delivery systems (Putney and Burke, 1998), and more recently as adjuvants (Maloy et al., 1994; specifically incorporated herein by reference). The ELI-Ag1 proteins, peptides and associated genetic constructs of the invention are suitable for incorporation into such PLG microparticles in order to provide enhanced protection upon vaccination.

Further modifications contemplated to be useful with the ELI-Ag1 proteins, peptides and genetic constructs include various combinations and forms of the proteins and peptides, particular modifications within the sequence, variations in recombinant production and adaptation of the synthetic constructs. All such aspects can now be practiced in light of the guidance provided herein and the knowledge of those of ordinary skill in the art.

An important aspect of the protective capacity of various *C. immitis* antigens has been attributed to their ability to elicit cytotoxic CD8+ T lymphocytes. This process involves the recognition of MHC class I molecules by intracellularly processed peptides targeted to the endoplasmic reticulum by the host cell machinery. To further facilitate the processes of MHC class I recognition and the formation of Class I-peptide complexes, ELI-Ag1 protein or peptide sequence (or underlying DNA) is modified to contain one or more endoplasmic reticulum insertion sequences, such as those derived from an adenovirus glycoprotein (Restifo et al., 1995; specifically incorporated herein by reference).

Another effective strategy involves the construction of a so-called "multiple antigen peptide (MAP)" construct containing various branches of the ELI-Ag1 proteins or peptides, whether recombinant or synthetic, linked to a core structure. For example, typical MAP constructs include four or more branches of synthetic or recombinant peptide antigens linked to a lysine-glycine core (Franke et al., 2000; specifically incorporated herein by reference). Such epitope-based vaccines are delivered in adjuvants to further enhance their protective efficacy and the induction of cytotoxic T cells.

III. ELI-Ag1 Proteins and Nucleic Acids

The present invention thus provides a range of purified, and in preferred embodiments, substantially purified, ELI-Ag1 proteins and peptides with sequences based upon the sequence of the ELI-Ag1 protein provided herein (SEQ ID NO:2). Succinctly, the proteins and peptides of the invention are termed "ELI-Ag1" proteins and peptides.

The term "purified" ELI-Ag1 protein or peptide, as used herein, refers to an ELI-Ag1 protein or peptide composition of the invention, isolatable, e.g., from *C. immitis* or *C. posadasii* and/or recombinant host cells, wherein the protein or peptide is purified to any degree relative to its naturally-obtainable state, i.e., relative to its purity within a cellular extract in which the protein or peptide may be expected to be present. A purified ELI-Ag1 protein or peptide therefore also refers to an ELI-Ag1 protein or peptide free from the environment in which it naturally occurs.

ELI-Ag1 proteins may be "full length" or "substantially full length", such as being about 224 amino acids or so in length. "Substantially" full length ELI-Ag1 proteins are generally within about 10%, and preferably, within about 5%, of the length of the native, full length ELI-Ag1 protein, i.e., within about 10%, or preferably within about 5%, of 224 amino acids in length. Accordingly, substantially full length ELI-Ag1 proteins may be from about 200 amino acids to about 223 amino acids in length; preferably, from about 202 amino acids to about 223 amino acids in length; and more preferably, from about 212 or 213 to about 223 amino acids in length. Lengths of about 200, 201, 202, 203, 204, 205, 206, 207, 208, 209, 210, 211, and preferably of about 212, 213, 214, 215, 216, 217, 218, 219, 220, 221, 222 or 223 are therefore substantially full length.

The ELI-Ag1 proteins, and particularly the peptides, may also be less then full length, such as domains, fragments, regions and/or epitopic peptides, as will be known to those of ordinary skill in the art in light of the present disclosure and as further described herein. Where less than full length proteins and ELI-Ag1 peptides are concerned, certain preferred examples will be those containing predicted immunogenic sites, such as those containing epitopes that induce cell-mediated immune responses and the like. The ELI-Ag1 peptides of the invention are described in more detail hereinbelow. In reference to the following descriptions of purity, fusion proteins, equivalents and nucleic acid segments encoding the ELI-Ag1 components of the invention, the descriptions refers to full length and substantially full length proteins as well as a range of ELI-Ag1 peptides, unless otherwise specifically stated or scientifically evident.

Generally, "purified" will refer to an ELI-Ag1 protein or peptide composition that has been subjected to fractionation to remove various non-ELI-Ag1 protein or peptide components, and which composition substantially retains its ELI-Ag1 protein or peptide status, as may be readily assessed by binding to antibodies or T cells reactive with the native ELI-Ag1 protein, providing protection against challenge and such like.

Where the term "substantially purified" is used, this will refer to a composition in which the ELI-Ag1 proteins or peptides of the invention form the major component of the composition, such as constituting about 50% of the proteins or peptides in the composition or more. In preferred embodiments, a substantially purified protein or peptide will constitute more than 60%, 70%, 80%, 90%, 91%, 92%, 93%, 94%, 95%, 96%, 97%, 98% or 99% or so of the proteins or peptides in the composition. However, this does not exclude the re-mixing of the ELI-Ag1 proteins or peptides of the invention, once purified, with other antigenic and/or vaccine components.

An ELI-Ag1 protein or peptide that is "purified to homogeneity," as applied to the present invention, means that the ELI-Ag1 protein or peptide has a level of purity where the ELI-Ag1 protein or peptide is substantially free from other proteins, peptides and biological components. For example, a purified ELI-Ag1 protein or peptide will often be sufficiently free of other peptide and protein components so that degradative sequencing may be performed successfully.

To purify an ELI-Ag1 protein or peptide, a natural or recombinant composition comprising at least some ELI-Ag1 proteins or peptides will be subjected to fractionation to remove various non-ELI-Ag1 protein or peptide components from the composition. Various techniques suitable for use in protein and peptide purification are well known to those of skill in the art and can be used herein.

Certain specific examples are the purification of ELI-Ag1 protein or peptide fusion proteins using specific binding partners. Such purification methods are routine in the art. As the present invention provides DNA sequences for ELI-Ag1 proteins and peptides, any fusion protein purification method can now be practiced. This is exemplified by glutathione S-transferase fusion proteins, expression in *E. Coli*, and isolation using affinity chromatography on glutathione-agarose. His-tagged ELI-Ag1 proteins or peptides are also included in the present invention.

Although preferred for use in certain embodiments, there is no general requirement that the ELI-Ag1 protein or peptide always be provided in its most purified state. Indeed, it is contemplated that less substantially purified ELI-Ag1 proteins and peptides, which are nonetheless enriched in ELI-Ag1 protein or peptide components, relative to the natural state, will have utility in certain embodiments. Methods exhibiting a lower degree of relative purification may have advantages in total recovery of protein or peptide product, or in maintaining the activity of expressed proteins or peptides. Even inactive products have utility in certain embodiments, particularly in antibody generation.

Further important aspects of the present invention concern isolated nucleic acid segments and recombinant vectors encoding the ELI-Ag1 proteins and peptides, including wild-type, polymorphic, mutant and second generation proteins and peptides, and the creation and use of recombinant host cells through the application of DNA technology, which express any such ELI-Ag1 protein or peptide. The nucleic acid segments are generally isolated free from total genomic DNA and are capable of expressing an ELI-Ag1 protein or peptide.

The following discussion of isolated nucleic acid segments is generally applicable to various nucleic acid segments encoding full length ELI-Ag1 proteins, substantially full length ELI-Ag1 proteins and a range of ELI-Ag1 peptides, as well as to fusion proteins and co-expression vectors. The nucleic acid segments of the invention preferably encode proteins and peptides with sequences based upon, derived from and/or equivalent to SEQ ID NO:2.

As used herein, the terms "nucleic acid segment" and "DNA segment" refer to nucleic acid and DNA molecules that have been isolated free from total genomic nucleic acids or DNA of a particular species, such as *C. immitis*. Therefore, a DNA segment encoding an ELI-Ag1 protein or peptide refers to a DNA segment that contains wild-type, polymorphic, variant or mutant ELI-Ag1 protein or peptide coding sequences isolated away from, or purified free from, total *Coccidioides* spp. genomic nucleic acids or DNA.

Included within the terms "nucleic acid and DNA segment", are nucleic acids and DNA segments and smaller fragments of such segments, and also recombinant vectors, including, for example, plasmids, cosmids, phage, viruses, and the like.

A nucleic acid or DNA segment comprising an isolated or purified wild-type, polymorphic, variant or mutant ELI-Ag1 protein or peptide "gene" refers to a nucleic acid or DNA segment including coding sequences and, in certain aspects, regulatory sequences, isolated substantially away from other naturally occurring genes or protein encoding sequences. In this respect, the term "gene" is used for simplicity to refer to a functional protein- or peptide-encoding unit. As will be understood by those in the art, this functional term refers to genomic sequences, cDNA sequences and smaller engineered gene segments that express, or may be adapted to express, proteins, peptides, polypeptides, domains, fusion proteins and mutants. Where "gene" is intended to encompass genomic regulatory or non-coding sequences this will be stated.

"Isolated substantially away from other coding sequences" means that the ELI-Ag1 protein- or peptide-encoding nucleic acid or DNA segment forms the significant part of the coding region, and that the overall nucleic acid segment does not contain large portions of naturally-occurring nucleic acids or DNA, such as large chromosomal fragments or other functional genes or cDNA coding regions. Of course, this refers to the nucleic acid or DNA segment as isolated, and does not exclude genes or coding regions later added to the segment by the hand of man, such as to create fusion proteins or multi-component expression systems.

In particular embodiments, the invention concerns isolated nucleic acid and DNA segments and recombinant vectors incorporating nucleic acid sequences that encode an ELI-Ag1 protein or peptide, and the proteins or peptides themselves, which include a contiguous amino acid sequence of at least about 7 or 8 amino acids from SEQ ID NO:2. In other particular embodiments, the invention concerns isolated nucleic acid and DNA segments and recombinant vectors that encode an ELI-Ag1 protein or fusion protein, and the proteins or fusion proteins themselves, which include within their amino acid sequences the full length protein sequence of SEQ ID NO:2, the substantially full length protein sequence of SEQ ID NO:2 or the protein sequence of SEQ ID NO:2 without the signal peptide sequence (amino acids 1-19 of SEQ ID NO:2).

Intermediate between the shortest peptides, e.g. of about 7 or 8 amino acids, and the full length proteins of about 224 amino acids, the present invention provides a range of isolated nucleic acids, DNA segments and recombinant vectors encoding peptides and polypeptides, and the peptides and polypeptides themselves, comprising sequences of various lengths that are contiguous with an amino acid sequence from SEQ ID NO:2. Thus, the invention provides nucleic acids, DNA segments and recombinant vectors encoding peptides and polypeptides, and the peptides and polypeptides themselves, comprising a sequence that corresponds to at least about 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222 or up to about 223 contiguous amino acids of SEQ ID NO:2. Those are the lengths meant by the term "a sequence of between about 8 and about 224 amino acids in length", as used herein.

In other embodiments, the invention concerns isolated nucleic acid and DNA segments and recombinant vectors incorporating DNA sequences that encode an ELI-Ag1 protein or peptide, and the proteins or peptides themselves, which include an amino acid sequence of between about 7 or 8 and about 224 amino acids in length that comprises a sequence essentially as set forth in a contiguous amino acid sequence from SEQ ID NO:2, preferably in a contiguous sequence of at least about 7, 8 or 10 amino acids from SEQ ID NO:2, up to and including an amino acid sequence of between about 7 or 8 and about 224 amino acids in length essentially as set forth in SEQ ID NO:2. The term "a sequence essentially as set forth in" means that the sequence substantially corresponds to a contiguous portion of SEQ ID NO:2, such as to any contiguous sequence of between about 7 or 8 and about 224 amino acids in length from SEQ ID NO:2, and has relatively few amino acids that are not identical to, or a biologically functional equivalent of, the amino acids of the contiguous reference sequence from SEQ ID NO:2. The term "biologically functional equivalent" is well understood in the art and is further defined in detail herein.

In terms of SEQ ID NO:2 and sequences that are in their entirety, or that include a sequence that is essentially as set forth in SEQ ID NO:2, the % identity and functional equivalency is calculated according to the number of non-identical and/or non-equivalent amino acids. For example, sequences that have, or include a region that has, 168 amino acids that are identical or equivalent to the amino acids of SEQ ID NO:2 are said to be at least about 75% identical or equivalent for the purposes of the present disclosure. Preferably, this concerns sequences and sequence regions that are substantially full length, such that the sequence overall includes about 56 non-identical or non-equivalent amino acids. However, sequences and sequence regions that are shorter in length and that lack the requisite number of amino acids are by no means excluded.

Those of ordinary skill in the art will understand that the following % identities and homologies are approximations, and that the proteins and peptides of the invention do not include partial amino acids. In this context, the invention includes isolated nucleic acid and DNA segments and recombinant vectors incorporating DNA sequences that encode an ELI-Ag1 protein or peptide, and the proteins or peptides themselves, which include an amino acid sequence of at least about 7, 8, 9 or 10 amino acids in length that is between about 70% and about 80%; or preferably, between about 81% and about 89%; or more preferably, between about 90% and about 94%, or between about 95% and about 99%, or between about 90% and about 99%, of amino acids that are identical or functionally equivalent to the amino acids of SEQ ID NO:2. Sequences, and preferably substantially full length sequences (or substantially full length sequences without the 1-19 N-terminal signal sequence), of at least about 70%, 71%, 72%, 73%, 74%, 75%, 76%, 77%, 78%, 79%, preferably of at least about 80%, 81%, 82%, 83%, 84%, 85%, 86%, 87%, 88%, 89%, and more preferably of at least about 90%, 91%, 92%, 93%, 94%, 95%, 96%, 97%, 98% and about 99% sequence identity or functionally equivalency (homology) to SEQ ID NO:2 are sequences of the invention that are "essentially as set forth in SEQ ID NO:2".

It is particularly preferred that a structural and/or biological activity of a biologically functional equivalent protein or peptide be maintained. Maintenance of structural and/or biological activity may be readily determined by those of ordinary skill in the art using any one of a number of assays known in the art and further described herein, including by the ability to bind to an antibody that has immunospecificity for an ELI-Ag1 protein, such as the ELI-Ag1 protein of SEQ ID NO:2.

In terms of nucleic acid sequences, the invention concerns isolated nucleic acid and DNA segments and recombinant vectors that include a contiguous nucleotide sequence, depending on the intended use chosen, of at least about 6, 7 or 8 contiguous nucleotides from SEQ ID NO:1, and preferably of at least about 15, 18, 20 or 21 contiguous nucleotides from SEQ ID NO:1. In other particular embodiments, the invention concerns isolated nucleic acid and DNA segments and recombinant vectors that include within their sequences the full length nucleotide sequence of SEQ ID NO:1, the substantially full length nucleotide sequence of SEQ ID NO:1, or the nucleotide sequence of the coding segment of SEQ ID NO:1, i.e., without the 5' and 3' untranslated regions.

Further embodiments of the invention are isolated nucleic acids, DNA segments and recombinant vectors that include within their sequence nucleic acid sequences of various lengths that are contiguous with a nucleic acid sequence from SEQ ID NO:1. Thus, the invention provides isolated nucleic acids, DNA segments and recombinant vectors comprising a sequence of between about 6 and about 1,080 contiguous nucleotides from SEQ ID NO:1, such as a sequence that corresponds to at least about 10, 20, 30, 40, 50, 60, 70, 80, 90, 100, 110, 120, 130, 140, 150, 175, 200, 250, 300, 350, 400, 450, 500, 550, 600, 650, 700, 750, 800, 850, 900, 950, 960, 970, 980, 990, 1000, 1010, 1020, 1030, 1040, 1050, 1060, 1070 or up to about 1075 contiguous nucleotides of SEQ ID NO:1. Those are the lengths meant by the term "a sequence of between about 6 or 8 and about 1,080 nucleotides in length", as used herein.

In yet further embodiments, the invention concerns isolated DNA segments and recombinant vectors that include a nucleic acid sequence of between about 6 or 8 and about 1,080 nucleotides in length that comprises a sequence essentially as set forth in a contiguous nucleic acid sequence from SEQ ID NO:1, preferably in a contiguous sequence from at least about 6, 8, 10, 15, 18, 20 or 21 to about 1,080 nucleotides in length essentially as set forth in SEQ ID NO:1. The term "essentially as set forth in SEQ ID NO:1" is used in the same sense as described above and means that the nucleic acid sequence substantially corresponds to a contiguous portion of SEQ ID NO:1 and has relatively few codons that are not identical, or functionally equivalent, to the codons of SEQ ID NO:1. The term "functionally equivalent codon" is used herein to refer to codons that encode the same amino acid, such as the six codons for arginine or serine, and also refers to codons that encode biologically equivalent amino acids (Table A).

TABLE A

| Amino Acids | | | DNA Codons | | | | | |
|---|---|---|---|---|---|---|---|---|
| | | | Codons | | | | | |
| Alanine | Ala | A | GCC | GCT | GCA | GCG | | |
| Cysteine | Cys | C | TGC | TGT | | | | |
| Aspartic acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGC | GGG | GGA | GGT | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTG | CTC | TTG | CTT | CTA | TTA |
| Methionine | Met | M | ATG | | | | | |
| Asparagine | Asn | N | AAC | AAT | | | | |
| Proline | Pro | P | CCC | CCT | CCA | CCG | | |
| Glutamine | Gln | Q | CAG | CAA | | | | |
| Arginine | Arg | R | CGC | AGG | CGG | AGA | CGA | CGT |
| Serine | Ser | S | AGC | TCC | TCT | AGT | TCA | TCG |
| Threonine | Thr | T | ACC | ACA | ACT | ACG | | |
| Valine | Val | V | GTG | GTC | GTT | GTA | | |
| Tryptophan | Trp | W | TGG | | | | | |
| Tyrosine | Tyr | Y | TAC | TAT | | | | |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth herein, including the maintenance of structural and/or functional biological activity, where protein expression is concerned. The addition of terminal sequences as applied to nucleic acid sequences includes, for example, the addition of various regulatory or other non-coding or coding sequences flanking either of the 5' or 3' portions of the coding region.

In terms of SEQ ID NO:1, the % identity and functional equivalency (homology) is calculated according to the number of non-identical and/or non-equivalent codons, such that sequences that have, or include a region that has, 168 codons that are identical or equivalent to the codons of SEQ ID NO:1 are said to be at least about 75% identical or equivalent for the purposes of the present disclosure. In this context, the comparison preferably concerns sequences and sequence regions that are substantially full length, such that the sequence overall includes about 56 non-identical or non-equivalent codons. However, sequences and sequence regions that are shorter in length and that lack the requisite number of codons are not excluded.

Those of ordinary skill in the art will understand that the following % identities and homologies are approximations, and that the DNA segments of the invention do not include partial nucleotides. However, as the DNA segments of the invention have many uses, including in hybridization and diagnostics, the DNA segments are not limited to including entire codons and may therefore begin and/or terminate with one or two additional nucleotides as well as with a complete codon.

Excepting flanking regions, and allowing for the degeneracy of the genetic code, sequences that have between about 70% and about 79%; or more preferably, between about 80% and about 89%; or more preferably, between about 90% and about 94%, or between about 95% and about 99%, or between about 90% and about 99% of nucleotides that are identical or functionally equivalent to the nucleotides of SEQ ID NO:1 will be sequences that are "essentially as set forth in SEQ ID NO:1". Substantially full length coding sequences of at least about 70%, 71%, 72%, 73%, 74%, 75%, 76%, 77%, 78%, 79%, preferably of at least about 80%, 81%, 82%, 83%, 84%, 85%, 86%, 87%, 88%, 89%, and more preferably of at least about 90%, 91%, 92%, 93%, 94%, 95%, 96%, 97%, 98% and about 99% sequence identity or functionally equivalency (homology) to the nucleotide sequence of SEQ ID NO:1, and preferably to the coding sequence within SEQ ID NO:1, i.e., the sequence of SEQ ID NO:1 without the 5' untranslated region of 142 nucleotides and without the 3' untranslated region of 266 nucleotides will often be preferred.

Sequences that are essentially the same as those set forth in SEQ ID NO:1, or a contiguous portion thereof, may also be functionally defined as sequences that are capable of hybridizing to a nucleic acid segment of SEQ ID NO:1 or a contiguous portion thereof (or containing the complement of SEQ ID NO:1 or a contiguous portion thereof) under appropriately stringent conditions. Suitable appropriately or relatively stringent hybridization conditions will be well known to those of skill in the art and are further exemplified herein.

In addition to hybridization and stringent hybridization techniques known in the art in general in regard to nucleic acids and nucleic acid segments, and exemplified herein in regard to *Coccidioides* and *C. immitis*, there is also considerable knowledge and skill in the art regarding hybridization and stringent hybridization with particular relevance to *Coccidioides*, including *C. immitis*, nucleic acids and nucleic acid segments. In this regard, U.S. Pat. No. 5,622,827 and U.S. Pat. No. 5,284,747 are specifically incorporated herein by reference in entirety, including their specification, claims and sequences, for purposes including further describing and enabling how to make *Coccidioides* and *C. immitis* nucleic acids, nucleic acid segments, nucleotide polymers, oligonucleotides, probes and primers and how to use such compositions in hybridization, stringent hybridization, nucleic acid detection and amplification.

Naturally, the present invention also encompasses isolated DNA segments that are complementary, or essentially complementary, to the sequence of SEQ ID NO:1 or a contiguous portion thereof. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1, or a contiguous portion thereof, under relatively stringent conditions such as those described herein.

The isolated nucleic acid segments of the present invention, regardless of the length of the coding sequence itself, may be combined with other nucleic acid and DNA sequences, such as promoters, polyadenylation signals, additional restriction enzyme sites, multiple cloning sites, other coding segments, and the like, such that their overall length may vary considerably. It is therefore contemplated that an isolated nucleic acid segment or fragment of almost any length may be employed, with the total length preferably being limited by the ease of preparation and use in the intended recombinant protocol.

For example, isolated nucleic acid segments or fragments may be prepared that include a short contiguous stretch identical to or complementary to a contiguous portion of SEQ ID NO:1, such as about a 15, 18, 20 or 21 nucleotide stretch, up to about 20,000, about 10,000, about 5,000 or about 3,000 base pairs in length. Nucleic acid and DNA segments with total lengths of about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 21, 22, 23, 24, 25, etc.; 30, 31, 32, etc.; 50, 51, 52, 53, etc.; 100, 101, 102, 103, etc.; 150, 151, 152, 153, etc.; including all integers through the 200-500; 500-1,000; 1,000-2,000; 2,000-3,000; 3,000-5,000; 5,000-10,000 ranges, up to and including sequences of about 12,001, 12,002, 13,001, 13,002, 15,001, 20,001 and the like.

The various purified probes and primers designed around the disclosed nucleotide sequences of the present invention may be of any length. For use alone, they will generally include a contiguous stretch of about 15 or 18, or preferably of about 20 or 21 nucleotides or so, from SEQ ID NO:1. For use as pair or triplets of primers, or as a plurality of sequences from SEQ ID NO:1 (e.g., as arrayed on a sequencing chip), the nucleic acid segments or fragments may include even shorter contiguous stretches from SEQ ID NO:1, such as about a 6, 8, 10, 12, 14, 16, 18 or so nucleotide stretch.

By assigning numeric values to a sequence, for example, the first residue is 1, the second residue is 2, etc., an algorithm defining all primers is "n to n+y", where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

It will also be understood that this invention is not limited to the particular isolated nucleic acid and amino acid sequences of SEQ ID NO:1 and SEQ ID NO:2. Recombinant vectors and isolated DNA segments may therefore variously include the coding region from SEQ ID NO:1, optionally with flanking sequences, coding regions bearing selected alterations or modifications in the basic coding region, or they may encode larger polypeptides that nevertheless include such coding regions or may encode biologically functional equivalent proteins or peptides that have variant amino acids sequences.

The isolated nucleic acid and DNA segments of the present invention encompass biologically functional equivalent ELI-Ag1 proteins and peptides that arise as a consequence of codon redundancy and functional equivalency that are known to occur naturally within nucleic acid sequences and the proteins thus encoded. Equally, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the immunogenicity and/or antigenicity of the protein.

One may also prepare fusion proteins and peptides, e.g., where the ELI-Ag1 protein or peptide coding region is aligned within the same expression unit with other proteins or peptides having desired functions. For example, for purification or immunodetection purposes (e.g., proteins that may be purified by affinity chromatography and enzyme label coding regions, respectively). Important examples are fusion proteins and peptides in which the ELI-Ag1 protein or peptide coding region is aligned within the same expression unit with a second, distinct *Coccidioides* spp. immunogenic protein or peptide (see hereinbelow).

IV. ELI-Ag1 Peptides and Epitopes

The present invention also encompasses isolated nucleic acid and DNA segments and recombinant vectors incorporating DNA sequences that encode a relatively small ELI-Ag1 peptide, and the peptides themselves, such as, for example, peptides of from about 7 or 8, about 10 or 12 or about 15 to about 30 or 50 amino acids in length, and more preferably, of from about 12 or 15 to about 30 amino acids in length. In particular, the peptides of the invention may be of about 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and about 50 amino acids in length. As set forth above, larger polypeptides up to and including proteins corresponding to the full-length sequences set forth in SEQ ID NO:2 are also provided, as are proteins encompassing amino acids 20-224 of SEQ ID NO:2.

N-terminal signal peptides of other *C. immitis* antigens have proven to be effective in immunization and vaccination (U.S. application Ser. No. 10/081,935, filed Feb. 22, 2002, specifically incorporated herein by reference). Therefore, the present invention also encompasses isolated peptides of from 19 to about 30, 35 or about 50 amino acids in length comprising or having the predicted N-terminal signal sequence of the ELI-Ag1 protein, i.e., comprising or having amino acids 1 to 19 of SEQ ID NO:2. Further isolated peptides of the invention are those of from 15 to about 30, 35 or about 50 amino acids in length comprising or having the predicted C-terminal glycosyl phosphatidylinositol (GPI) anchor site, i.e., comprising or having amino acids 210 to 224 of SEQ ID NO:2.

Within the peptides and polypeptides, and associated DNA and expression constructs of the invention, the peptides and polypeptides may be pre-selected or designed to contain, or be likely to contain, one or more protective epitopes. The prediction and/or identification of protective epitopes from within the ELI-Ag1 protein is now routine, given that the 224 amino acid sequence is disclosed herein. However, useful, antigenic, immunogenic and/or protective peptides and polypeptides are not limited to prediction and identification from sequence analyses alone. For example, immunogenic and even protective peptides and polypeptides can now be identified from the ELI-Ag1 protein sequence using empirical immunization and vaccination studies, in accordance with those disclosed herein. Also, useful peptides and polypeptides are not required to be immunogenic or protective, as any peptide will have a number of uses, e.g., in binding assays and diagnostics.

By way of example only, one may wish to use isolated peptides of from anywhere from 7 to 23 amino acids in length, up to about 30, 35 or about 50 amino acids in length, which comprise or have one of the isolated peptide sequences from SEQ ID NO:2, as set forth in Table 1. Depending on the chosen sequence, these isolated peptides may thus be from 7, 8, 9, 10, 11, 12, 13, 14, 15, 16, 17, 18, 19, 20, 21, 22 or 23 amino acids in length at the shortest to about 30, 31, 32, 33, 34, 35, 36, 37, 38, 39, 40, 41, 42, 43, 44, 45, 46, 47, 48, 49 or about 50 amino acids in length at the longest.

The isolated peptides of from 7 to about 50 amino acids in length, depending on the chosen sequence, may thus comprise or have an amino acid sequence as set forth in, or essentially as set forth in, any of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21 or SEQ ID NO:22.

In certain embodiments, particularly those for use as an antigen, isolated peptides of from 7 to about 50 amino acids in length, depending on the chosen sequence, may preferably comprise or have an amino acid sequence as set forth in the antigenic determinants of any of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 or SEQ ID NO:12.

Other particular examples are isolated peptides of from 9 to about 50 amino acids in length that comprise or have an MHC Class I binding motif sequence as set forth in the sequences of any of SEQ ID NO:13, SEQ ID NO:14, SEQ ID NO:15, SEQ ID NO:16 or SEQ ID NO:17. Further particular examples are isolated peptides of from 9 to about 50 amino acids in length that comprise or have an MHC Class II binding motif sequence as set forth in the sequences of any of SEQ ID NO:18, SEQ ID NO:19, SEQ ID NO:20, SEQ ID NO:21 or SEQ ID NO:22.

Peptides of less than about 7 or 8 amino acids in length may also be used in the present invention, so long as they contain sufficient sequence information to provide a measurable benefit in one or more useful embodiments, such as in antibody generation or T cell binding, and most particularly, in the protection against *Coccidioides* spp. infections. The peptides may thus be of any minimum, functional length, such as, e.g., about 4, 5, 6, 7, 8 or 9 amino acids in length.

In terms of amino acid substitutions, a wide range of substitutions is tolerated within the peptides of the invention. As detailed herein, the ability to make and test variants, e.g., using site-directed mutagenesis, is now routine in the art and is performed without undue experimentation once a useful, parent sequence has been provided, as in the present invention. In choosing such variants and substitutions, it may be convenient not to modify, or at least not to extensively modify the Class I epitopes predicted within SEQ ID NO:2, as set forth in any of SEQ ID NO:13, SEQ ID NO:14, SEQ ID NO:15, SEQ ID NO:16 or SEQ ID NO:17.

It will be understood that there is no requirement for any truncated or variant sequences of the invention to function to essentially the same degree of effectiveness as the native ELI-Ag1 protein sequence. It will rather be realized that certain other benefits may be worthwhile tolerating a degree of reduction of function in certain assays. Such features include, e.g., increased bioavailability, cross-reactivity and such like. The ease and even cost of production may also favor using shorter or variant peptides or constructs, even if their vaccination profile is somewhat reduced in some aspects from the ELI-Ag1 protein. However, shorter and/or variant peptides that function to essentially the same degree as the ELI-Ag1 protein will be preferred for use in the present invention. Peptides that are at least about as effective in vaccination as the ELI-Ag1 protein of SEQ ID NO:2 will be particularly preferred, and peptides and derivatives that have increased biological effectiveness in comparison to the ELI-Ag1 protein of SEQ ID NO:2 are also encompassed within the invention.

Accordingly, peptides corresponding to one or more T cell or antigenic determinants, or "epitopic core regions", of the ELI-Ag1 protein can also be prepared. Exemplary peptides include those comprising epitopes as set forth herein in Table 1. Such peptides should generally be at least 7 amino acid residues in length. "Synthetic" peptides, i.e., peptides generated using automated peptide synthesis machines, will generally be a maximum of about 35, 36, 37, 38, 39, 40, 41, 42, 43, 44, 45, 46, 47, 48, 49 or about 50 residues long or so, which is the approximate upper length limit of automated peptide synthesis machines, such as those available from Applied Biosystems (Foster City, Calif.). Longer peptides may also be prepared, e.g., by recombinant means. Recombinant peptides of any desired length may be used.

U.S. Pat. No. 4,554,101 (Hopp), incorporated herein by reference, teaches the identification and preparation of epitopes from primary amino acid sequences on the basis of hydrophilicity. Although prediction of epitopes that induce cell-mediated immune responses is important to the present invention, through the methods disclosed in U.S. Pat. No. 4,554,101, one of skill in the art is able to identify general epitopes from within an amino acid sequence such as those of SEQ ID NO:2. Numerous scientific publications have also been devoted to the prediction of secondary structure, and to the identification of epitopes, from analyses of amino acid sequences (Chou & Fasman, 1974a; 1974b; 1978a; 1978b; 1979; each incorporated herein by reference). Any of these may be used, if desired, to supplement the teachings of U.S. Pat. No. 4,554,101.

Moreover, computer programs are currently available to assist with predicting antigenic portions and epitopic core regions of proteins. Examples include those programs based upon the Jameson-Wolf analysis (Jameson & Wolf, 1998; Wolf et al., 1988; each incorporated herein by reference), the program PepPlot® (Brutlag et al., 1990; Weinberger et al., 1985; each incorporated herein by reference), and other new programs for protein tertiary structure prediction (Fetrow & Bryant, 1993; incorporated herein by reference). Further commercially available software capable of carrying out such analyses is termed MacVector (IBI, New Haven, Conn.).

In further embodiments, major antigenic determinants of a polypeptide may be identified by an empirical approach in which portions of the cDNA (gene) encoding the polypeptide are expressed in a recombinant host, and the resulting proteins tested for their ability to elicit an immune response. For example, PCR™ can be used to prepare a range of peptides lacking successively longer fragments of, e.g., the C-terminus of the peptides of the invention. The immunoactivity of each of these peptides is determined to identify those fragments or domains of the polypeptide that are immunodominant. Further studies in which only a small number of amino acids are removed at each iteration then allows the location of the antigenic determinants of the polypeptide to be more precisely determined. The same approach is applied to substitutions. The working examples of the present application show that these approaches are suitable for use with the present invention.

Another method for determining the major antigenic determinants of a polypeptide is the SPOTs™ system (Genosys Biotechnologies, Inc., The Woodlands, Tex.). In this method, overlapping peptides are synthesized on a cellulose membrane, which following synthesis and deprotection, is screened using a polyclonal or monoclonal antibody. The antigenic determinants of the peptides that are initially identified can be further localized by performing subsequent syntheses of smaller peptides with larger overlaps, and by eventually replacing individual amino acids at each position along the immunoreactive peptide.

In terms of T cell epitopes, immunogenic portions may be identified using computer analysis, such as the Tsites program (Rothbard and Taylor, 1988; Deavin et al., 1996, each specifically incorporated herein by reference), which searches for peptide motifs that have the potential to elicit Th responses. Peptides with motifs appropriate for binding to murine and human class I or class II MHC may be identified according to BIMAS (Parker et al., 1994, specifically incorporated herein by reference) and other HLA peptide binding prediction analyses. To confirm immunogenicity, peptides may, if desired, be tested using an HLA binding assays, including a transgenic mouse model and/or using in vitro binding and stimulation assays.

Once one or more such analyses are completed, peptides are prepared that contain at least the essential features of one or more antigenic and/or sequence determinants that induce cell-mediated immune responses. The peptides are then employed in the generation of protective immune responses. Minigenes or gene fusions encoding these determinants can also be constructed and inserted into expression vectors by standard methods, for example, using PCR™ cloning methodology.

The use of particularly small peptides for vaccination can benefit from conjugation of the peptide to an immunogenic carrier protein, such as hepatitis B surface antigen, keyhole limpet hemocyanin or bovine serum albumin. Methods for performing this conjugation are well known in the art.

Modifications and changes may also be made in the structure of the ELI-Ag1 protein, peptides and nucleic acids of the present invention, and still obtain molecules having like or otherwise desirable characteristics. Such are the meanings of "biologically functional equivalents of" and "conservative amino acid substitutions within" the proteins, polypeptides and peptides of the present invention.

For example, certain amino acids may be substituted for other amino acids in a peptide structure without appreciable loss of interactive binding capacity, for example, peptide signal capacity, epitopes, immunoprotection and the like. Since it is the interactive capacity and nature of a peptide that defines that peptide's biological functional activity, certain amino acid sequence substitutions can be made in a peptide sequence (or, of course, its underlying DNA coding sequence) and nevertheless obtain a peptide with like (agonistic) properties. It is thus contemplated that various changes may be made in the sequence of the ELI-Ag1 proteins and peptides, or underlying DNA, without appreciable loss of their biological utility or activity.

In terms of functional equivalents, it is well understood by the skilled artisan that, inherent in the definition of a "biologically functional equivalent peptide or gene", is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted.

In particular, where shorter length peptides are concerned, it is contemplated that fewer amino acid substitutions should be made within the given peptide. Longer peptides may have an intermediate number of changes. Of course, a plurality of distinct peptides with different substitutions may easily be made and used in accordance with the invention, particularly within vaccines.

It is also well understood that where certain residues are shown to be particularly important to the biological or structural properties of a protein or peptide, such residues may not generally be exchanged. Particular examples are epitopes that induce cell-mediated immune responses, signal peptide sequences, sequences that target the ER and such like. Maintenance of biological structure/function can always be easily tested though. For example, functional equivalents may be defined as those peptides that maintain a substantial ability to function like the native peptides of SEQ ID NO:2.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein or peptide is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent peptide thereby created is intended for use in immunological embodiments, as in the present invention. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

In addition to the foregoing description of biologically functional equivalents and conservative amino acid substitutions within proteins, polypeptides and peptides in general, there is also considerable knowledge and skill in the art regarding biologically functional equivalents and conservative amino acid substitutions within Coccidioides spp. fungi, including C. immitis, proteins, polypeptides and peptides in particular. In this regard, U.S. application Ser. No. 10/417,923, filed Apr. 16, 2003 (published as US 2004/0001843 A1 on Jan. 1, 2004), U.S. application Ser. No. 10/418,962, filed Apr. 18, 2003 (published as US 2003/0224013 A1 on Dec. 4, 2003), U.S. application Ser. No. 10/417,997, filed Apr. 16, 2003 (published as US 2003/0219455 A1 on Dec. 4, 2003) and U.S. application Ser. No. 10/794,287, filed Mar. 3, 2004 with priority to Mar. 14, 2003 (published as US 2004/0181046 A1 on Sep. 16, 2004), are specifically incorporated herein by reference in entirety, including their specification, claims and sequence listing, for purposes including further describing and enabling how to make and use biologically functional equivalents and conservative amino acid substitutions within Coccidioides spp. and C. immitis proteins, polypeptides and peptides.

U.S. application Ser. No. 10/417,923, U.S. application Ser. No. 10/418,962, U.S. application Ser. No. 10/417,997 and U.S. application Ser. No. 10/794,287 are also specifically incorporated herein by reference in entirety for purposes including further describing and enabling how to make and use compositions comprising isolated nucleic acids, vectors and/or expression vectors encoding Coccidioides proteins, polypeptides and peptides, and compositions comprising the resultant proteins, polypeptides and peptides themselves, wherein the Coccidioides protein, polypeptide and/or peptide "comprises" an amino acid sequence of a defined SEQ ID NO or an amino acid sequence of a defined SEQ ID NO with conservative amino acid substitutions.

The "uses" incorporated from U.S. application Ser. No. 10/417,923, U.S. application Ser. No. 10/418,962, U.S. application Ser. No. 10/417,997 and U.S. application Ser. No. 10/794,287 include how to make Coccidioides compositions, nucleic acids, vectors, expression vectors, proteins, polypeptides and/or peptides, including those with conservative amino acid substitutions, and how to use such components in methods for generating and eliciting immune responses and antibodies, methods for treating or preventing valley fever or coccidioidomycosis and methods for vaccinating against valley fever or coccidioidomycosis in animals, mammals and humans.

While discussion has focused on functionally equivalent peptides arising from amino acid changes, it will be appreciated that these changes may be effected by alteration of the encoding DNA; taking into consideration also that the genetic code is degenerate and that two or more codons may code for the same amino acid. A table of amino acids and their codons is presented herein for use in such embodiments (Table A), as well as for other uses, such as in the design of probes and primers and the like.

Site-specific mutagenesis is a technique useful in the preparation of individual peptides, or biologically functional equivalent peptides, through specific mutagenesis of the underlying DNA. The technique further provides a ready ability to prepare and test sequence variants by introducing one or more nucleotide sequence changes into the DNA. U.S. Pat. No. 4,888,286 is specifically incorporated herein by reference to further exemplify such processes.

Site-specific mutagenesis allows the production of mutants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

Techniques of site-specific mutagenesis are well known in the art. Certain techniques typically employ a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector that includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the ELI-Ag1 proteins and peptides using site-directed mutagenesis described above is provided as a means of producing potentially useful species and is not meant to be limiting, as there are other ways in which sequence variants of ELI-Ag1 proteins and peptides may be obtained. For example, recombinant vectors encoding the desired gene may be treated with mutagenic agents, such as hydroxylamine, to obtain sequence variants.

Although the foregoing methods are suitable for use in mutagenesis, the use of PCR™ is generally now preferred. This technology offers a quick and efficient method for introducing desired mutations into a given DNA sequence. The following text particularly describes the use of PCR™ to introduce point mutations into a sequence, as may be used to change the amino acid encoded by the given sequence. Adaptations of this method are also suitable for introducing restriction enzyme sites into a DNA molecule.

In this method, synthetic oligonucleotides are designed to incorporate a point mutation at one end of an amplified segment. Following PCR™, the amplified fragments are blunt-ended by treating with Klenow fragments, and the blunt-ended fragments are then ligated and subcloned into a vector to facilitate sequence analysis.

To prepare the template DNA that one desires to mutagenize, the DNA is subcloned into a high copy number vector, such as pUC19, using restriction sites flanking the area to be mutated. Template DNA is then prepared using a plasmid miniprep. Appropriate oligonucleotide primers that are based upon the parent sequence, but which contain the desired point mutation and which are flanked at the 5' end by a restriction enzyme site, are synthesized using an automated synthesizer. It is generally required that the primer be homologous to the template DNA for about 15 bases or so. Primers may be purified by denaturing polyacrylamide gel electrophoresis, although this is not absolutely necessary for use in PCR™. The 5' end of the oligonucleotides should then be phosphorylated.

The template DNA should be amplified by PCR™, using the oligonucleotide primers that contain the desired point mutations. The concentration of $MgCl_2$ in the amplification buffer will generally be about 15 mM. Generally about 20-25 cycles of PCR™ should be carried out as follows: denaturation, 35 sec. at 95° C.; hybridization, 2 min. at 50° C.; and extension, 2 min. at 72° C. The PCR™ will generally include a last cycle extension of about 10 min. at 72° C. After the final extension step, about 5 units of Klenow fragments should be added to the reaction mixture and incubated for a further 15 min. at about 30° C. The exonuclease activity of the Klenow fragments is required to make the ends flush and suitable for blunt-end cloning.

The resultant reaction mixture should generally be analyzed by nondenaturing agarose or acrylamide gel electrophoresis to verify that the amplification has yielded the predicted product. One would then process the reaction mixture by removing most of the mineral oils, extracting with chloroform to remove the remaining oil, extracting with buffered phenol and then concentrating by precipitation with 100% ethanol. Next, one should digest about half of the amplified fragments with a restriction enzyme that cuts at the flanking sequences used in the oligonucleotides. The digested fragments are purified on a low gelling/melting agarose gel.

To subclone the fragments and to check the point mutation, one would subclone the two amplified fragments into an appropriately digested vector by blunt-end ligation. This would be used to transform *E. coli*, from which plasmid DNA could subsequently be prepared using a miniprep. The amplified portion of the plasmid DNA would then be analyzed by DNA sequencing to confirm that the correct point mutation was generated. This is important as Taq DNA polymerase can introduce additional mutations into DNA fragments.

The introduction of a point mutation can also be effected using sequential PCR™ steps. In this procedure, the two fragments encompassing the mutation are annealed with each other and extended by mutually primed synthesis. This fragment is then amplified by a second PCR™ step, thereby avoiding the blunt-end ligation required in the above protocol. In this method, the preparation of the template DNA, the generation of the oligonucleotide primers and the first PCR™ amplification are performed as described above. In this process, however, the chosen oligonucleotides should be homologous to the template DNA for a stretch of between about 15 and about 20 bases and must also overlap with each other by about 10 bases or more.

In the second PCR™ amplification, one would use each amplified fragment and each flanking sequence primer and carry PCR™ for between about 20 and about 25 cycles, using the conditions as described above. One would again subclone the fragments and check that the point mutation was correct by using the steps outlined above.

In using either of the foregoing methods, it is generally preferred to introduce the mutation by amplifying as small a fragment as possible. Of course, parameters such as the melting temperature of the oligonucleotide, as will generally be influenced by the GC content and the length of the oligo, should also be carefully considered. The execution of these methods, and their optimization if necessary, will be known to those of skill in the art.

One effective method of confirming that a functionally equivalent protein or peptide has retained sufficient ELI-Ag1 protein or peptide characteristics is to confirm that the equivalent peptide is immunologically cross-reactive with the ELI-Ag1 protein or peptide. Tests of immunological cross-reactivity are a straightforward matter and can be readily determined using specific assays, i.e., based upon competition for binding sites. In the present invention, assays involving T cells and antibodies may be suitable. A valuable test of biological activity in accordance with the present invention is the maintenance of significant or substantial immunoprotective capacity, which can be readily tested by those of ordinary skill in the art according to the present disclosure.

In addition to the ELI-Ag1 protein and peptidyl compounds described herein, other sterically similar compounds may be formulated to mimic the key portions of the peptide structure, e.g., to also function in immunoprotection. Such compounds, which may be termed peptidomimetics, may be used in the same manner as the peptides of the invention and hence are also functional equivalents.

The underlying rationale behind the use of peptide mimetics is that the peptide backbone exists chiefly to orientate amino acid side chains in such a way as to facilitate molecular interactions, such as those of antigens and T cells. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as known those of ordinary skill in the art. Once the component amino acids of the turn are determined, mimetics can be constructed to achieve a similar spatial orientation of the essential elements of the amino acid side chains.

The generation of further structural equivalents or mimetics may be achieved by the techniques of modeling and chemical design known to those of skill in the art. The art of modeling is now well known, and by such methods chemical variants of ELI-Ag1 proteins and peptides can be designed and synthesized. It will be understood that all such sterically designed constructs fall within the scope of the present invention.

V. Additional Antigenic Components

In certain embodiments, the ELI-Ag1 proteins, peptides and nucleic acid segments of the invention are intended for use with at least a second *Coccidioides* spp. protein, peptide or nucleic acid segment. Unless otherwise stated (e.g., where multimers and MAP constructs are concerned), the second *Coccidioides* spp. protein, peptide or nucleic acid segment is typically a second, distinct *Coccidioides* spp. protein, peptide or nucleic acid segment. A "second, distinct" *Coccidioides* spp. protein, peptide or nucleic acid segment means a protein, peptide or nucleic acid segment "distinct from", i.e., in addition to, the ELI-Ag1 protein, peptide or nucleic acid segment, which forms the "first" *Coccidioides* spp. protein, peptide or nucleic acid segment, as described herein.

Where a second, distinct *Coccidioides* spp. protein, peptide or nucleic acid segment is used in conjunction with the ELI-Ag1 protein, peptide or nucleic acid segment of the invention, the second, distinct *Coccidioides* spp. component may be used in "admixture" with the first, ELI-Ag1 component. For example, as distinct components within a multi-component or "multivalent" protein, peptide or mixed component vaccine. Admixtures and vaccines involving nucleic acids will preferably comprise nucleic acid coding regions that express the encoded products. The coding or expression regions may be maintained on separate expression vectors, or may be comprised within a single expression vector that nonetheless expresses distinct first and second *Coccidioides* spp. proteins and/or peptides.

In other aspects, the second, distinct *Coccidioides* spp. protein, peptide or nucleic acid segment is used in "operative attachment" to the ELI-Ag1 protein, peptide or nucleic acid segment of the invention. For example, where proteins and/or peptides are concerned, the second, distinct *Coccidioides* spp. protein or peptide is operatively attached or linked to the ELI-Ag1 protein or peptide to form a hybrid product or "fusion protein". Where nucleic acid segments are concerned, the second, distinct *Coccidioides* spp. nucleic acid segment or coding region is "operatively attached" to the first nucleic acid segment or coding region, which encodes the ELI-Ag1 protein or peptide. "Operatively attached" nucleic acid segments and coding regions, in this context, means nucleic acids attached "in frame", wherein the overall nucleic acid segment then encodes a recombinant fusion protein, in which the first protein or peptide is operatively linked to the second protein or peptide.

Any of the ELI-Ag1 protein or peptide sequences of the invention may thus be combined with one or more other sequences, either for ease of production and purification, or with an intended therapeutic benefit. So long as the inclusion of any additional amino acid sequences does not impair the function of the ELI-Ag1 protein or peptide sequence of the primary discovery, the use of such longer sequences is included within the present invention. Accordingly, the overall length of the peptides or proteins for use in the invention may be from about 7 or 8 amino acids or so, up to and including about 224 amino acids of the full length ELI-Ag1 protein, and further up to 230, 240, 250, 300, 350, 400, 450, 500, 550, 600, 650, 700, 800, 900 and about 1,000 amino acids in length and the like.

The following discussion of exemplary second, distinct *Coccidioides* spp. protein, peptide and nucleic acid segments applies equally to second, distinct components used in admixture and to second, distinct components used in operative attachment. The *Coccidioides* spp. components described merely exemplify certain combinations of the invention, and are by no means limiting on the type or number of *Coccidioides* spp. components for use together with the ELI-Ag1 components of the present invention.

*C. immitis* cell wall extracts enriched in a component termed "Antigen 2 (Ag2)" have been shown to induce protection against challenge with *C. immitis* (Lecara et al., 1983). Ag2 was described as a heavily glycosylated protein present in the cell walls of *Coccidioides* spp. mycelial- and spherule-phase cells. A comparison of the nucleic acid sequence of the genes that encode Ag2 (Jiang et al., 1999a) and a proline-rich antigen (PRA) (Dugger et al., 1996) showed that the two were identical. For this reason, the nomenclature "Ag2/PRA" was employed.

The deduced primary translation product of Ag2/PRA has 194 amino acids, containing a hydrophobic N-terminal of 18 amino acids that has sequence homology to signal peptide sequences, a central region containing 10 examples of a tetrapeptide repeat (TXX'P), and a C-terminal GPI anchor site. These features are consistent with a prepro-Ag2/PRA undergoing a post-translational modification to yield a mature glycosylated Ag2/PRA protein that is anchored on the plasma membrane of spherule- and mycelial-phase cells of this dimorphic fungus.

Using sequence comparison algorithms, the Ag2/PRA protein has been predicted to express T and B cell epitopes, the most prominent of which are said to be in an internal hydrophilic domain that contains tetrapeptide repeats (Zhu et al., 1996). A subsequent report indicated that Ag2/PRA expresses linear and conformational B cell epitopes localized within amino acids 19-96 (Zhu et al., 1997). Kirkland et al. (1998), Jiang et al. (1999a; 1999b) and Abuodeh et al. (1999) have reported the use of the full length Ag2/PRA recombinant protein and/or full length cDNA as a vaccine with varying degrees of success in animals challenged with *C. immitis* via the intraperitoneal route. Ag2/PRA may be used in conjunction with the ELI-Ag1 components of the present invention.

In addition to the foregoing description of the Ag2/PRA protein and the publications, each of which are specifically incorporated herein by reference, U.S. application Ser. No. 10/417,923, filed Apr. 16, 2003 (published as US 2004/0001843 A1 on Jan. 1, 2004), is also specifically incorporated herein by reference in entirety, including the specification, claims and sequence listing, for purposes including further describing and enabling the use of polypeptides and nucleic acids derived from Ag2/PRA. U.S. application Ser. No. 10/417,923 particularly concerns polypeptide fragments defined by amino acids 1 to 106 of the Ag2/PRA protein ("Ag2/PRA1-106") and by amino acids 27 to 106 of the Ag2/PRA protein ("Ag2/PRA27-106"), and the corresponding nucleic acid segments. The preparation and use of nucleic acid segments and polypeptides of amino acids 1 to 106 (Ag2/PRA1-106) and amino acids 27 to 106 (Ag2/PRA27-106) of the Ag2/PRA protein are additionally described in Peng et al., 2002, which is also specifically incorporated herein by reference for purposes including further describing and enabling the use of polypeptides and nucleic acids derived from Ag2/PRA. One or more of the Ag2/PRA1-106 and Ag2/PRA27-106 polypeptide or nucleic acid components may be used in conjunction with the ELI-Ag1 components of the present invention.

Certain of the present inventors and others undertook various lines of investigation to more precisely examine the vaccine potential of Ag2/PRA. Since studies in other models have shown that genetic vaccination was often superior to vaccination with recombinant or native peptides, studies were done to assess the vaccine efficacy of Ag2/PRA cDNA (1-194). The gene vaccine induces a very strong level of protection against intraperitoneal challenge, as judged by CFU in the lungs, livers, and spleen and by the survival of 100% of the vaccinated mice as compared to mice given the vector alone. Mice vaccinated with the Ag2/PRA cDNA showed increased production of the T-helper 1 cytokine interferon-γ (IFN-γ). The Th1 response is known to be important in host defenses against this fungus (Cox, 1993; Cox and Magee, 1998).

Further studies were undertaken to delineate the immunoprotective domain of Ag2/PRA cDNA. For these studies, Ag2/PRA cDNA (1-194) and a series of PCR™-generated truncations were constructed and evaluated for their vaccine efficacy. BALB/c mice immunized with the full-length Ag2/PRA cDNA (1-194) were protected against challenge, whereas mice immunized with Ag2/PRA cDNA (19-194), which lacked the N-terminal signal peptide, were significantly less protected (U.S. application Ser. No. 10/081,935).

The finding that the full-length, but not the 19-194 truncated Ag2/PRA cDNA, protected mice against challenge suggested that the N-terminal 18 amino acids (signal peptide) was important in inducing protective immunity. Further studies were conducted to generate the Ag2/PRA cDNA (1-18) construct and to compare the effect of the Ag2/PRA cDNA (1-18) construct directly with Ag2/PRA cDNA (1-194) and Ag2/PRA cDNA (19-194). The results established that the signal peptide construct induced protection in mice after intraperitoneal challenge with a lethal dose of 2,500 *C. immitis* arthroconidia to a level comparable to that induced by the full-length Ag2/PRA cDNA (U.S. application Ser. No. 10/081,935).

Also, the immunizing capacity of the Ag2/PRA (1-18) signal sequence was not attributable to a nonspecific immunostimulatory effect of DNA, as evidenced by the fact that mice immunized with a frame-shift mutation of Ag2/PRA (1-18) were not protected against challenge. Furthermore, a synthetic peptide corresponding to the translated sequence of Ag2/PRA (1-18) DNA protected mice, albeit at a lower level than the Ag2/PRA (1-18) DNA vaccine.

The N-terminal sequence of the Ag2/PRA protein, termed "Ag2/PRA(1-18)", may also be used in combination with the present invention. In addition to the foregoing description of Ag2/PRA(1-18), U.S. application Ser. No. 10/081,935, filed Feb. 22, 2002, is specifically incorporated herein by reference in entirety, including the sequence listing, for purposes including even further describing and enabling the use of Ag2/PRA(1-18) peptide, nucleic acid and related compositions.

Further *Coccidioides* spp. protein, peptide or nucleic acid segments that may be used as second, distinct *Coccidioides* spp. components in conjunction with the ELI-Ag1 components of the present invention include, e.g., the *Coccidioides* specific antigen (CSA or Csa), as described by Pan and Cole (1995; specifically incorporated herein by reference). In addition to the description of CSA in Pan and Cole, 1995, specifically incorporated herein by reference, U.S. provisional application Ser. No. 60/455,221, filed Mar. 14, 2003, and particularly U.S. application Ser. No. 10/794,287, filed Mar. 3, 2004 (published as US 2003/0224013 A1 on Dec. 4, 2003), are specifically incorporated herein by reference in their entirety, including the specifications, claims and sequence listings, for purposes including further describing and enabling the use of CSA proteins, polypeptides, nucleic acids, vectors and methods of use.

The urea amidohydrolase, urease or Ure protein, peptide or nucleic acid segments (Yu et al., 1997; Li et al., 2001; each specifically incorporated herein by reference) may also be combined with the ELI-Ag1 of the invention. In addition to the description of Ure in Yu et al., 1997 and Li et al., 2001, U.S. application Ser. No. 10/418,962, filed Apr. 18, 2003 (published as US 2003/0224013 A1 on Dec. 4, 2003), is also specifically incorporated herein by reference in entirety, including the specification, claims and sequence listing, for purposes including further describing and enabling the use of proteins, polypeptides, nucleic acids and vectors derived from Ure and methods of use.

1,3-β-glucanosyltransferase (Gel-1) antigens, proteins, peptides and nucleic acid segments, as described by Delgado et al., 2003, specifically incorporated herein by reference, may also be combined with the ELI-Ag1 of the invention. In addition to the description of Gel-1 in Delgado et al., 2003, U.S. application Ser. No. 10/417,997, filed Apr. 16, 2003 (published as US 2003/0219455 A1 on Dec. 4, 2003), is also specifically incorporated herein by reference in entirety, including the specification, claims and sequence listing, for purposes including further describing and enabling the use of antigens, proteins, polypeptides, nucleic acids and vectors derived from Gel-1 and methods of use.

VI. Pharmaceutical Compositions

The ELI-Ag1 protein, peptide and/or nucleic acid compositions, fusion proteins or constructs, vaccines or cocktails thereof are formulated into pharmaceutical compositions for administration. The most basic pharmaceutical compositions of the present invention will generally comprise an effective amount of at least a first ELI-Ag1 protein, peptide and/or nucleic acid, dissolved or dispersed in a pharmaceutically acceptable carrier or aqueous medium. Combined therapeutics are also contemplated, and the same type of underlying pharmaceutical compositions may be employed for both single and combined medicaments and vaccines.

The phrases "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use. Veterinary uses are particularly, although not exclusively, contemplated for applications in valuable and valued animals, such as farm animals and domestic pets, including horses, cattle, cats and dogs.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

"Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like.

A. Injectable Formulations

The ELI-Ag1 protein, peptide and/or nucleic acid constructs of the present invention may be formulated for parenteral administration, e.g., formulated for injection via the intravenous, intramuscular, sub-cutaneous, transdermal, or other such routes, including direct instillation into the lungs. The preparation of an aqueous composition that contains such an ELI-Ag1 protein, peptide and/or nucleic acid as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The ELI-Ag1 protein, peptide and/or nucleic acid compositions can be formulated into a sterile aqueous composition in a neutral or salt form. Solutions of the ELI-Ag1 protein, peptide and/or nucleic acids as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the ELI-Ag1 protein, peptide and/or nucleic acid constructs should be extensively dialyzed to remove undesired small molecular weight molecules, and/or lyophilized for more ready formulation into a desired vehicle, where appropriate. Sterile injectable solutions are prepared by incorporating the active ELI-Ag1 protein, peptide and/or nucleic acid agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of the ELI-Ag1 protein, peptide and/or nucleic acid construct admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards. Upon formulation, the ELI-Ag1 protein, peptide and/or nucleic acid solutions will be administered in a manner compatible with the dosage formulation and in such amount as is therapeutically effective.

B. Sustained Release Formulations

Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver the ELI-Ag1 protein, peptide and/or nucleic acid constructs in accordance with the present invention.

Pharmaceutical "slow release" capsules or "sustained release" compositions or preparations may also be used. Slow release formulations are generally designed to give a constant drug level over an extended period and may be used to deliver ELI-Ag1 protein, peptide and/or nucleic acid construct in accordance with the present invention. The slow release formulations are typically implanted in the vicinity of the disease site, for example, the lungs.

Suitable examples of sustained-release preparations include semipermeable matrices of solid hydrophobic polymers containing the ELI-Ag1 protein, peptide and/or nucleic acid construct, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and γ ethyl-L-glutamate; non-degradable ethylene-vinyl acetate; degradable lactic acid-glycolic acid copolymers, such as the Lupron Depot™ (injectable microspheres composed of lactic acid-glycolic acid copolymer and leuprolide acetate); and poly-D-(−)-3-hydroxybutyric acid.

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thio-disulfide interchange, stabilization is achieved by modifying sulfhydryl residues, lyophilizing from acidic solutions, controlling moisture content, using appropriate additives, developing specific polymer matrix compositions, and the like.

C. Liposomes and Nanocapsules

In certain embodiments, liposomes and/or nanoparticles may also be employed with the ELI-Ag1 protein, peptide and/or nucleic acid constructs. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles may be are easily made.

D. Topical Formulations

In the broadest sense, formulations for topical administration include those for delivery via the mouth (buccal) and through the skin. "Topical delivery systems" also include transdermal patches containing the ingredient to be administered. Delivery through the skin can further be achieved by iontophoresis or electrotransport, if desired.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin include ointments, creams, gels and pastes comprising the ingredient to be administered in a pharmaceutical acceptable carrier. The formulation of an ELI-Ag1 protein, peptide and/or nucleic acid construct for topical use, such as in creams, ointments and gels, includes the preparation of oleaginous or water-soluble ointment bases, will be well known to those in the art in light of the present disclosure. For example, these compositions may include vegetable oils, animal fats, and more preferably, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Formulations for rectal administration may be presented as a suppository with a suitable base comprising, for example, cocoa butter or a salicylate. Formulations suitable for vaginal administration may be presented as pessaries, tampons, creams, gels, pastes, foams or spray formulations containing in addition to the active ingredient such carriers as are known in the art to be appropriate.

E. Nasal Formulations Local delivery via the nasal and respiratory routes is particularly contemplated for use in the present invention. These delivery routes are also suitable for delivering agents into the systemic circulation. Formulations of active ingredients in carriers suitable for nasal administration are therefore also included within the invention, for example, nasal solutions, sprays, aerosols and inhalants. Where the carrier is a solid, the formulations include a coarse powder having a particle size, for example, in the range of 20 to 500 microns, which is administered, e.g., by rapid inhalation through the nasal passage from a container of the powder held close up to the nose.

Suitable formulations wherein the carrier is a liquid are useful in nasal administration. Nasal solutions are usually aqueous solutions designed to be administered to the nasal passages in drops or sprays and are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Inhalations and inhalants are pharmaceutical preparations designed for delivering a drug or compound into the respiratory tree of a patient. A vapor or mist is administered and reaches the affected area. This route can also be employed to deliver agents into the systemic circulation. Inhalations may be administered by the nasal or oral respiratory routes. The administration of inhalation solutions is only effective if the droplets are sufficiently fine and uniform in size so that the mist reaches the bronchioles.

Another group of products, also known as inhalations, and sometimes called insufflations, comprises finely powdered or liquid drugs that are carried into the respiratory passages by the use of special delivery systems, such as pharmaceutical aerosols, that hold a solution or suspension of the drug in a liquefied gas propellant. When released through a suitable valve and oral adapter, a metered does of the inhalation is propelled into the respiratory tract of the patient. Particle size is of major importance in the administration of this type of preparation. It has been reported that the optimum particle size for penetration into the pulmonary cavity is of the order of 0.5 to 7 µm. Fine mists are produced by pressurized aerosols and hence their use in considered advantageous.

VII. Adjuvants

Immunization protocols have used adjuvants to stimulate responses for many years. Some adjuvants affect the way in which antigens are presented. For example, the immune response is increased when protein antigens are precipitated by alum. Emulsification of antigens also prolongs the duration of antigen presentation. Other adjuvants, for example, certain organic molecules obtained from bacteria, act on the host rather than on the antigen. An example is muramyl dipeptide (N-acetylmuramyl-L-alanyl-D-isoglutamine [MDP]), a bacterial peptidoglycan. MDP is believed to stimulate macrophages, but also appears to stimulate B cells directly. The effects of adjuvants, therefore, are not antigen-specific. When administered together with a purified antigen, however, they can be used to selectively promote the response to the antigen. Adjuvants have been used experimentally to promote a generalized increase in immunity against unknown antigens (e.g., U.S. Pat. No. 4,877,611).

The present invention contemplates that a variety of adjuvants may be employed, including the RIBI MPL-SE adjuvant. Certain selected adjuvants preferred for use are biodegradable and biocompatible polymers, such as PLG, PLA and PLGA, particularly those formulated as microspheres and microparticles (Maloy et al., 1994; specifically incorporated herein by reference). Certain other useful adjuvants are listed in Table B. This list is not intended to be exhaustive, merely exemplary of the different kinds of adjuvants that can be used in accordance with this invention.

TABLE B

| Exemplary Adjuvants | |
|---|---|
| Alhydrogel | |
| Alkyl Lysophosphilipids (ALP) | |
| Bcg | |
| Bestatin | |
| Biliverdin | including derivatives and glyco-conjugates |
| Bilirubin | including derivatives and glyco-conjugates, such as monoglycourano-glycans and diglycouranoglycans |
| Biotin | including biotinylated derivatives |
| Carnosine | including derivatives |
| Chitin | |
| Chitosan | deacetylated chitin |
| Cholesteryl Succinate | |
| *Cornyebacterium Parvum* | whole or part of cell including oligosaccharides and glycolipids |
| *C. Granulosum* | whole or part of cell including P40 a peptidoglycan with a glycoprotein |
| Monophoshoryl Lipid A | Deacetylated |
| Monophosphoryl Lipid A | Synthetic |
| Isoprinosine | |
| Lithosperman | lithosperman A, lithosperman B or lithosperman C |
| Trehalose Monomycolate | |
| Trehalose Dimycolate | |
| *Mycobacterial* Species | whole or part of cell including glycolipids, phenolic glycolipids, peptides such as 45/47 kda and BCG |
| Muramyl Dipeptide | N-acetyl muramyl-L-alanyl-D-isoglutamine |
| Muramyl Tripeptide | MF75.2 |
| Threonyl-Muramyl Dipeptide | |
| Murametide | |
| Murabutide | |
| Lipoteichoic Acid | LTA |
| Ribitol Teichoic Acid | RTA |
| Glycerol Teichoic Acid | GTA |
| Superantigens | *S. aureus* enterotoxins, *S. epidermidis* enterotoxins, *S. pyogenes* enterotoxins, *E. coli* exotoxins |
| *Staphylococcus* Species | whole or part of cell including peptidoglycans and enterotoxins |
| Viruses | whole or part of particle including Vaccinia, Newcastle disease virus, vesicular stomatitis virus, papilloma virus and rhinovirus |
| Synthetic Peptides | pentamers, hexamers, heptamers, octamers, nonamers, decamers, etc.; such as polylysine and threonine-alanine peptides |
| Recombinant Prolactin | |
| Glycosaminoglycans | and lipid and peptide derivatives |
| Glycosaminoglycouranoglycans | |
| Glycosaminoglycolipids | |
| Glycosaminoglycourano-Glycolipids | |
| Glycosaminoglycopeptides | |
| Glycosaminoglycourano-Glycopeptides | |
| Phosphorylated Glycosaminoglycans | |

TABLE B-continued

Exemplary Adjuvants

| | |
|---|---|
| Sulphanted Glycosaminoglycan | |
| Qs-21 | |
| Quil-A | |
| Polymethylmethyl Acrylate (PMMA) | |
| Retinoic Acid | |
| Lentinan | |
| Levan | |
| Malic Anhydride-Divinyl Ether (MVE-2) | |
| Hemocyanin | from keyhole limpet (KLH) |
| Hemoerythrin | molluscan, arthropod hemoerythrin from annelids and lower invertebrates |
| Pteridines | |
| Nucleic Acids | preferably poly A, poly T, poly AT, poly GC and poly IC-LC |
| Oligonucleotides | varying kilobases |
| Lentinen | |
| Lectins | part or whole; from plants and animals |

Certain useful adjuvants are the teichoic acids from Gram negative cells. These include the lipoteichoic acids (LTA), ribitol teichoic acids (RTA) and glycerol teichoic acid (GTA). Active forms of their synthetic counterparts may also be employed in connection with the invention (Takada et al., 1995).

Hemocyanins and hemoerythrins may also be used in the invention. The use of hemocyanin from keyhole limpet (KLH) is preferred, although other molluscan and arthropod hemocyanins and hemoerythrins may be employed.

Various polysaccharide adjuvants may also be used. For example, Yin et al. (1989) describe the use of various pneumococcal polysaccharide adjuvants on the antibody responses of mice. The doses that produce optimal responses, or that otherwise do not produce suppression, as indicated in Yin et al. (1989) should be employed. Polyamine varieties of polysaccharides are preferred, such as chitin and chitosan, including deacetylated chitin.

A further preferred group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative MTPPE, are also contemplated.

U.S. Pat. No. 4,950,645 describes a lipophilic disaccharide-tripeptide derivative of muramyl dipeptide which is proposed for use in artificial liposomes formed from phosphatidyl choline and phosphatidyl glycerol. It is said to be effective in activating human monocytes and destroying tumor cells, but is non-toxic in generally high doses. The compounds of U.S. Pat. No. 4,950,645 and PCT Patent Application WO 91/16347, are also proposed for use in the present invention.

BCG and BCG-cell wall skeleton (CWS) may also be used as adjuvants in the invention, with or without trehalose dimycolate. Trehalose dimycolate may be used itself. Azuma et al. (1988) show that trehalose dimycolate administration correlates with augmented resistance to influenza virus infection in mice. Trehalose dimycolate may be prepared as described in U.S. Pat. No. 4,579,945.

Amphipathic and surface active agents, e.g., saponin and derivatives such as QS21 (Cambridge Biotech), form yet another group of adjuvants for use with the immunogens of the present invention. Nonionic block copolymer surfactants (Rabinovich et al., 1994) may also be employed. Oligonucleotides, as described by Yamamoto et al. (1988) are another useful group of adjuvants. Quil A and lentinen are further suitable adjuvants.

Superantigens are also contemplated for use as adjuvants in the present invention. "Superantigens" are generally bacterial products that stimulate a greater proportion of T lymphocytes than peptide antigens without a requirement for antigen processing (Mooney et. al., 1994). Superantigens include *Staphylococcus* exoproteins, such as the alpha, beta, gamma and delta enterotoxins from *S. aureus* and *S. epidermidis*, and the alpha, beta, gamma and delta *E. coli* exotoxins.

Common *Staphylococcus* enterotoxins are known as staphylococcal enterotoxin A (SEA) and staphylococcal enterotoxin B (SEB), with enterotoxins through E (SEE) being described (Rott et. al., 1992). *Streptococcus pyogenes* B (SEB), *Clostridium perfringens* enterotoxin (Bowness et. al., 1992), cytoplasmic membrane-associated protein (CAP) from *S. pyogenes* (Sato et. al., 1994) and toxic shock syndrome toxin-1 (TSST-1) from *S. aureus* (Schwab et. al., 1993) are further useful superantigens.

Another group of adjuvants for use in the invention are the detoxified endotoxins, such as the refined detoxified endotoxin of U.S. Pat. No. 4,866,034. These refined detoxified endotoxins are effective in producing adjuvant responses in mammals.

The detoxified endotoxins may be combined with other adjuvants. Combination of detoxified endotoxins with trehalose dimycolate is contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins, is also envisioned to be useful, as described in U.S. Pat. No. 4,520,019.

MPL is another immunopotentiating agent for use herein, which has been used to date to up-regulate the immunogenicty of various vaccines and to confer significant protection against infection and challenge. MPL is known to be safe and effective (Vosika et al., 1984). Indeed, 100 µg/m$^2$ is known to be safe for human use, even on an outpatient basis (Vosika et al., 1984).

MPL generally induces polyclonal B cell activation, and has been shown to augment antibody production in many systems, for example, in immunologically immature, aging, nude and Xid mice. Antibody production has been shown against erythrocytes; T cell dependent and independent antigens; Pnu-immune vaccine; isolated tumor-associated antigens (U.S. Pat. No. 4,877,611); against syngeneic tumor cells (Ravindranath et al, 1994a; 1994b); and against tumor-associated gangliosides (Ravindranath et al., 1994a; 1994b).

Another useful attribute of MPL is that it augments IgM responses, which is a useful feature of an adjuvant for use in certain embodiments of the present invention. Myers et al. (1995) reported on the ability of MPL to induce IgM antibodies, by virtue T-cell-independent antibody production. In the Myers et al. (1995) studies, MPL was conjugated to the hapten, TNP. MPL was proposed for use as a carrier for other haptens, such as peptides.

MPL also activates and recruits macrophages, and MPL-stimulated T cells enhance IL-1 secretion by macrophages. MPL is also known to activate superoxide production, lysozyme activity, phagocytosis, and killing of *Candida* in murine peritoneal macrophages. The effects of MPL on T cells include the endogenous production of cytotoxic factors, such as TNF, in serum of BCG-primed mice by MPL. MPL is known to act with TNF-α to induce release of IFN-γ by NK cells.

MPL is also known to be a potent T cell adjuvant. For example, MPL stimulates proliferation of melanoma-antigen specific CTLs. Nontoxic MPL inactivates suppressor T cell activity. Naturally, in the physiological environment, the inactivation of T suppressor cells allows for increased benefit for the animal. MPL is also known to induce aggregation of platelets and to phosphorylate a platelet protein prior to induction of serotonin secretion.

The structure and function of MPL are now known in the art. The fatty acid moieties of MPL can vary, even in commercial species. Baker et al. (1992) analyzed the structural features that influence the ability of lipid A and its analogs to abolish expression of suppressor T cell activity. They reported that decreasing the number of phosphate groups in lipid A from two to one, i.e., creating monophosphoryl lipid A, MPL, as well as decreasing the fatty acyl content, primarily by removing the residue at the 3 position, resulted in a progressive reduction in toxicity. However, these structural modifications did not influence its ability to abolish the expression of Ts function (Baker et al., 1992). These types of MPL may be used in the present invention.

Baker et al. (1992) also showed that reducing the fatty acyl content from five to four (lipid A precursor $IV_A$ or $I_a$) eliminated the capacity to influence Ts function, but not to induce polyclonal activation of B cells. These studies show that in order to be able to abolish the expression of Ts function, lipid A should be a glucosamine disaccharide; may have either one or two phosphate groups; and should have at least five fatty acyl groups. In addition, the chain length of the nonhydroxylated fatty acid, as well as the location of acyloxyacyl groups (2' versus 3' position), may play an important role (Baker et al., 1992). Fatty acyl chain lengths of $C_{12}$ to $C_{14}$ are particularly contemplated for use in this invention.

Synthetic MPLs form a further group of suitable adjuvants. For example, the MPL derivatives described in U.S. Pat. No. 4,987,237 are contemplated for use in the present invention. U.S. Pat. No. 4,987,237 describes MPL derivatives that contain one or more free groups, such as amines, on a side chain attached to the primary hydroxyl groups of the monophosphoryl lipid A nucleus through an ester group. The derivatives provide a convenient method for coupling the lipid A through coupling agents to various biologically active materials. The immunostimulant properties of lipid A are maintained. All MPL derivatives in accordance with U.S. Pat. No. 4,987,237 are envisioned for use as adjuvants with this invention.

Various adjuvants, even those that are not commonly used in humans, may still be employed in animals, where, for example, one desires to subsequently obtain activated T cells or to protect valuable or valued animals from infection.

VIII. Therapeutic Kits

The present invention also provides therapeutic kits comprising ELI-Ag1 protein, peptide and/or nucleic acid component(s) for use in the present prophylactic, vaccination and treatment methods. Such kits will generally contain, in suitable container means, a pharmaceutically acceptable formulation of at least one of the ELI-Ag1 protein, peptides and/or nucleic acids of the invention. The kits may also contain other pharmaceutically acceptable formulations for combined vaccination or therapy. For example, such kits may contain any one or more of a range of ELI-Ag1 proteins, peptides or antigens, other proteins or peptides, including Ag2/PRA(1-18), Ag2/PRA1-106, Ag2/PRA27-106, Csa, Ag2-Csa fusion proteins, Gel-1 and/or Ure, and/or conventional anti-fungal therapeutics.

Acyl urea compounds may be used to treat *Coccidioides* spp. and diseases such as coccidioidomycosis. These include acyl urea compounds such as those disclosed in U.S. Pat. Nos. 5,420,163 and 5,837,734, each specifically incorporated herein by reference. Such compounds may be used in the combined compositions and kits of the invention and in the combination methods of the invention, and U.S. Pat. Nos. 5,420,163 and 5,837,734 are therefore also specifically incorporated herein by reference in regard to the methodological, treatment and prophylactic embodiments.

The kits may have a single container (container means) that contains the ELI-Ag1 protein, peptide or DNA component, with or without any additional components, or they may have distinct containers for each desired agent. Where combined therapeutics are provided, a single solution may be pre-mixed, either in a molar equivalent combination, or with one component in excess of the other. Alternatively, each of the ELI-Ag1 protein, peptide or DNA components and other agents, such as *C. immitis* antigens and/or antifungal therapeutics may be maintained separately within distinct containers prior to administration to an animal or patient.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

The containers of the kit will generally include at least one vial, test tube, flask, bottle, syringe or other container means, into which the ELI-Ag1 protein, peptide component and any other desired agent, may be placed and, preferably, suitably aliquoted. Where separate components are included, the kit will also generally contain a second vial or other container into which these are placed, enabling the administration of separated designed doses. The kits may also comprise a second/third container means for containing a sterile, pharmaceutically acceptable buffer or other diluent.

The kits may also contain a means by which to administer the ELI-Ag1 protein, peptide component to an animal or patient, e.g., one or more needles or syringes, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

In general, the kits may also contain diagnostic components so that the invention may be used to confirm the presence ELI-Ag1 protein, peptide prior to treatment, and/or determine the degree of *Coccidioides* spp. in a biological sample from a patient. Combined detection kits may thus include diagnostic agents, proteins, antibodies and nucleic acids.

Kits with components for detection can also be used to monitor the success of vaccination and/or therapies against *Coccidioides* spp. infection. The lack of detection of *Coccidioides* spp., or a decrease in the levels of *Coccidioides* spp. in comparison to the levels in a corresponding biological sample prior to therapy, is indicative of a patient that is being successfully treated for the condition associated with *Coccidioides* spp. infection or colonization.

IX. Therapeutic Regimens

Particularly important embodiments of the present invention concern the use of the ELI-Ag1 protein, peptide and DNA in immunological-based therapies for the prevention or treatment of *Coccidioides* spp. infections and associated diseases and conditions. The treatment of patients with Valley Fever is particularly contemplated, although the treatment also extends to veterinary embodiments and to prophylactic measures in subjects at risk for *Coccidioides* spp. infection and/or those traveling to infected areas. In fact, since protective immunity is shown herein, the present invention is particularly useful for preparing vaccines.

Therefore, the invention encompasses ELI-Ag1 protein, peptide antigen and/or nucleic acid compositions, or "vaccines", preferably formulated with pharmaceutically acceptable carriers, diluents and/or adjuvants. Other formulations, vaccines or "antigenic cocktails" are also provided, comprising additional components, such as peptides, antigens, adjuvants, multimers and the like, as are often employed in the formulation of vaccines.

The present invention thus particularly provides methods of generating an immune response, preferably, a protective immune response, which methods generally comprise administering to an animal, including a human subject, a pharmaceutically acceptable composition comprising an "immunologically effective" or "immunostimulatory" amount of an ELI-Ag1 protein, peptide or nucleic acid composition in accordance with the invention. The composition may include partially or significantly purified ELI-Ag1 proteins and/or peptides, obtained from natural or recombinant sources. Smaller peptides that include immunogenic epitopes, such as those of about 8, about 12, about 15, about 18, about 20, about 25, about 30, and about 35 amino acids may be used. The ELI-Ag1 proteins and/or peptides may also be combined with other agents and *Coccidioides* spp. components, as desired.

By "immunologically effective" and "immunostimulatory" amount" is meant an amount of an ELI-Ag1 protein, peptide or DNA composition that is capable of generating an immune response in the recipient animal or patient, preferably a protective immune response. This particularly includes the generation of T cell responses, including cytotoxic T cell responses, but also the generation of antibody responses (B cell response). The generation of immune responses, whether or not they are immunoprotective, has significant utility in the production of useful bioreagents, e.g., activated T cells and even reactive antibodies, for use as tools and in diagnostic embodiments. Therefore, although the invention includes vaccination regimens, it will be understood that achieving "vaccination" is not necessary for practicing all useful aspects of the invention.

The invention is preferably used in the generation of immunoprotective responses that have important utility in various clinical and veterinary prophylactic and therapeutic embodiments. Accordingly, such methods for the stimulation of an immune response include vaccination regimens designed to prevent or lessen *Coccidioides* spp. infections and associated diseases, and treatment regimens that may lessen the severity or duration of any infection or medical condition. So, even where therapy and vaccination are concerned, it will be understood that complete protection any from *Coccidioides* spp. infection whatsoever is not a requirement of the invention and that any clinical or veterinary benefit is a useful outcome of practicing the invention.

The use of the present ELI-Ag1-derived peptides and epitopes provides various advantages. Exemplary advantages include the ease of preparation and purification, the relatively low cost and improved reproducibility of production, and advantageous biodistribution. The preparation of vaccines that contain peptide sequences as active ingredients is generally well understood in the art, as exemplified by U.S. Pat. Nos. 4,608,251; 4,601,903; 4,599,231; 4,599,230; 4,596,792; and 4,578,770, each incorporated herein by reference.

Whether protein-, peptide- or DNA-based, various methods of achieving adjuvant effects for the vaccines are included. For example, the use of agents such as aluminum hydroxide or phosphate (alum), commonly used as 0.05 to 0.1 percent solution in phosphate buffered saline; and admixtures with synthetic polymers of sugars (Carbopol) used as 0.25 percent solution. Emulsions in physiologically acceptable oil vehicles such as mannide mono-oleate (Aracel A) or emulsion with 20 percent solution of a perfluorocarbon (Fluosol-DA) used as a block substitute may also be employed.

One may also generate an immune response in an animal or patient by administering to the animal or human subject a pharmaceutically acceptable composition comprising an immunologically effective amount of an ELI-Ag1 protein- or peptide-encoding nucleic acid composition, or even an immunologically effective amount of an attenuated live organism that includes and expresses an ELI-Ag1 protein- or peptide-encoding nucleic acid composition (see below). As with the peptide vaccines and therapeutics, the "immunologically effective amounts" are those amounts capable of stimulating T cell and/or B cell responses, preferably T cell responses, and more preferably, proving immunoprotection.

All vaccines of the invention should be administered in a manner compatible with the dosage formulation, and in such amount as will be immunogenic and therapeutically effective. The quantity to be administered depends on the subject to be treated, including, e.g., the capacity of the individual's immune system to react, and the degree of protection/treatment desired. Precise amounts of active ingredient required to be administered will be readily determinable by the skilled practitioner. Suitable regimes for initial administration and booster shots are also variable, and are typified by an initial administration followed by subsequent inoculations or other administrations.

The manner of application may be varied widely, as will be understood by those of ordinary skill in the art. Any of the conventional methods for administration of a vaccine are applicable. These will include oral application on a solid physiologically acceptable base or in a physiologically acceptable dispersion, parenterally, by injection and the like. The dosage of the vaccine may also vary with the route of administration.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1-5 years, usually three years, will be desirable to maintain protective levels. The course of the immunization may be followed by assays for activated T cells produced.

X. DNA Vaccination

In light of the working examples herein, and the knowledge of those of ordinary skill in the art regarding DNA vaccination, particularly in the *Coccidioides* field, it will be understood that virtually all vaccination regimens of the present invention are appropriate for use with genetic immunization. In addition to parenteral routes of DNA inoculation, including intramuscular and intravenous injections, mucosal vaccination is also contemplated, as may be achieved by direct application.

The stimulation of immune responses by administering a nucleic molecule to an animal, termed "DNA or genetic vaccination", is now well known in the art. Indeed, successful DNA vaccination has been demonstrated for a number of diseases using a variety of antigen-encoding DNA, as evidenced by U.S. Pat. Nos. 6,384,018, 6,284,533 and 6,165,993, each specifically incorporated herein by reference. The earlier scientific articles of Tang et al. (1992); Cox et al. (1993); Fynan et al. (1993); Ulmer et al. (1993); Wang et al. (1993) and Whitton et al. (1993) are also each incorporated herein by reference. The use of attenuated organisms, such as vaccinia viruses and *salmonella*, that express recombinant DNA products is also now established in the art and contemplated for use in the present invention.

The naked DNA technology, often referred to as genetic immunization, is particularly suitable to protect against infectious organisms. Immunization with DNA has been successfully employed to protect animals from challenge with influenza A (Ulmer et al., 1993). The use of the ELI-Ag1 protein- or peptide-encoding nucleic acid compositions of the present invention in such genetic immunization techniques is thus another useful vaccination regimen. The ELI-Ag1 protein- or peptide-encoding nucleic acid segments could be used in virtually any form, including naked DNA and plasmid DNA, and may be administered to the animal in a variety of ways, as described, for example, by Fynan et al. (1993).

In addition to naked DNA technology, or genetic immunization, using recombinant DNA or plasmids, other embodiments of the invention deliver DNA entrapped in liposomes or lipofectamine-DNA complexes. In yet further embodiments, the ability of viruses to enter cells and to integrate into host cell genome is used to transfer ELI-Ag1 protein- or peptide-encoding nucleic acids into target cells. Gene therapy vectors of the present invention thus include viral vectors.

Retroviruses have promise as gene delivery vectors due to their ability to integrate their genes into the host genome, transferring a large amount of foreign genetic material, infecting a broad spectrum of species and cell types and of being packaged in special cell-lines. Other viruses, such as adenovirus, herpes simplex viruses (HSV), cytomegalovirus (CMV), and adeno-associated virus (AAV), such as those described by U.S. Pat. Nos. 5,139,941 and 5,843,742, incorporated herein by reference, may also be engineered to serve as vectors for gene transfer.

Adenoviruses do not integrate their genetic material into the host genome and therefore do not require host replication for gene expression, making them ideally suited for rapid, efficient, heterologous gene expression. Adenoviral vectors may be employed with the present invention, and techniques for preparing replication-defective infective viruses are well known in the art, as exemplified by U.S. Pat. Nos. 6,410,010 and 6,403,370, each specifically incorporated herein by reference.

In certain further embodiments, an HSV gene therapy vector may be used. A factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. HSV also is relatively easy to manipulate and can be grown to high titers. Thus, delivery is less of a problem, both in terms of volumes needed to attain sufficient MOI and in a lessened need for repeat dosings.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

XI. Recombinant Vectors, Host Cells and Expression

Recombinant vectors form important further aspects of the present invention. As described in the foregoing sections, recombinant expression may be used in this invention to prepare proteins and/or peptides for subsequent delivery or to express proteins and/or peptides in vivo, wherein a therapeutic benefit naturally results. Unless otherwise particularly specified, the recombinant vectors discussed herein include those for use in vitro and in vivo.

The term "recombinant vector, expression vector or construct", as used herein, thus means any type of genetic construct containing a nucleic acid coding for an expressed product in which part or all of the nucleic acid encoding sequence is capable of being transcribed. Typically, the transcript is translated into a peptide or protein. Thus, "expression" preferably includes both transcription of a nucleic acid segment and translation of mRNA into a product.

Vectors typically have a coding portion of a nucleic acid or DNA segment positioned under the transcriptional control of a promoter. A "promoter" refers to a DNA sequence recognized by the synthetic machinery of the cell, or introduced synthetic machinery, required to initiate the specific transcription of a gene. The phrases "operatively positioned", "under control" or "under transcriptional control" mean that the promoter is in the correct location and orientation in relation to the nucleic acid segment to control RNA polymerase initiation and expression of the nucleic acid segment.

The promoter may be in the form of the promoter that is naturally associated with the *Coccidioides* spp. Ag2/PRA, as is known in the art and as may be obtained by isolating the 5' non-coding sequences located upstream of the coding segment, for example, using recombinant cloning and/or PCR™ technology, in connection with the compositions disclosed herein. PCR™ technology is disclosed in U.S. Pat. Nos. 4,683,202 and 4,682,195, each incorporated herein by reference.

In other embodiments, certain advantages will be gained by positioning the coding nucleic acid or DNA segment under the control of a recombinant, or heterologous, promoter. As used herein, a recombinant or heterologous promoter refers to a promoter that is not normally associated with *Coccidioides* spp. Ag2/PRA in its natural environment. Such promoters may include promoters normally associated with other nucleic acids and genes, and/or promoters isolated from any other bacterial, viral, eukaryotic, or mammalian cell.

Naturally, it will be important to employ a promoter that effectively directs the expression of the nucleic acid or DNA segment in the cell type or organism chosen for expression. The use of promoter and cell type combinations for protein expression is generally known to those of skill in the art of molecular biology, for example, see Sambrook et al. (2001; incorporated herein by reference). The promoters employed may be constitutive, or inducible, and can be used under the appropriate conditions to direct high level expression of the introduced nucleic acid or DNA segment, such as is advantageous in the large-scale production of recombinant proteins or peptides.

At least one module in a promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid of the invention is not believed to be critical, so long as it is capable of expressing the nucleic acid in the targeted cell. Thus, where a mammalian or human cell is targeted, it is preferable to position the nucleic acid coding region adjacent to and under the control of a promoter that is capable of being expressed in a mammalian or human cell. Generally speaking, such a promoter might include either a mammalian, human or viral promoter. Exemplary promoters include those derived from HSV and tetracycline controlled promoters.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters that are well-known in the art to achieve expression of a transgene are contemplated as well, provided that the levels of expression are sufficient for a given purpose. Virtually any element/promoter may be employed in the context of the present invention to regulate the *Coccidioides* spp. peptide expression.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a transgene of the invention. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

As indicated, it is contemplated that one may use any regulatory element to express the *Coccidioides* spp. peptide of the present invention. However, under certain circumstances it may be desirable to use the innate promoter region associated with the gene of interest to control its expression, such as the native *Coccidioides* spp. Ag2/PRA promoter. As noted above, in most cases, genes are regulated at the level of transcription by regulatory elements that are located upstream, or 5', to the genes.

In general, to identify regulatory elements for *Coccidioides* spp. Ag2/PRA, one would obtain a genomic DNA segment corresponding to the region located between about 5 to 50 nucleotides up to about 2000 nucleotides or more upstream from the transcriptional start site of the gene. A convenient method used to obtain such a sequence is to utilize restriction enzyme(s) to excise an appropriate DNA fragment. Restriction enzyme technology is commonly used in the art and will be generally known to the skilled artisan. For example, one may use a combination of enzymes from the extensive range of known restriction enzymes to digest the genomic DNA. Analysis of the digested fragments would determine which enzyme(s) produce the desired DNA fragment. The desired region may then be excised from the genomic DNA using the enzyme(s). If desired, one may even create a particular restriction site by genetic engineering for subsequent use in ligation strategies.

Alternatively, one may choose to prepare a series of DNA fragments differentiated by size through the use of a deletion assay with linearized DNA. In such an assay, enzymes are also used to digest the genomic DNA; however, in this case, the enzymes do not recognize specific sites within the DNA but instead digest the DNA from the free end(s). In this case, a series of size differentiated DNA fragments can be achieved by stopping the enzyme reaction after specified time intervals. Of course, one may also choose to use a combination of both restriction enzyme digestion and deletion assay to obtain the desired DNA fragment(s).

Once the desired DNA fragment has been isolated, its potential to regulate a gene and determine the basic regulatory unit may be examined using any one of several conventional techniques. It is recognized that once the core regulatory region is identified, one may choose to employ a longer sequence that comprises the identified regulatory unit. This is because although the core region is all that is ultimately required, it is believed that particular advantages may accrue, in terms of regulation and level of induction achieved, where one employs sequences that correspond to the natural control regions over longer regions. The preferred length will be in part determined by the type of expression system used and the results desired.

Numerous methods are known in the art for precisely locating regulatory units within larger DNA sequences. Most conveniently, the desired control sequence is isolated within a DNA fragment(s) that is subsequently modified using DNA synthesis techniques to add restriction site linkers to the fragment(s) termini. This modification readily allows the insertion of the modified DNA fragment into an expression cassette that contains a reporter gene that confers on its recombinant host cell a readily detectable phenotype that is either expressed or inhibited, as may be the case.

Generally reporter genes encode a polypeptide not otherwise produced by the host cell; or a protein or factor produced by the host cell but at much lower levels; or a mutant form of a polypeptide not otherwise produced by the host cell. Preferably the reporter gene encodes an enzyme that produces a calorimetric, fluorometric or other readily detectable change in the host cell, which is detectable by in situ analysis and is a quantitative or semi-quantitative function of transcriptional activation. Exemplary reporter genes encode esterases, phosphatases, proteases and other proteins detected by activity that generates a chromophore or fluorophore, as will be known to the skilled artisan. Two well-known examples of such reporter genes are *E. coli* beta-galactosidase and chloramphenicol-acetyl-transferase (CAT). Alternatively, a reporter gene may render its host cell resistant to a selection agent. For example, the gene neo renders cells resistant to the antibiotic neomycin. It is contemplated that virtually any host cell system compatible with the reporter gene cassette may be used to determine the regulatory unit. Thus mammalian or other eukaryotic cells, insect, bacterial or plant cells may be used.

Once a DNA fragment containing the putative regulatory region is inserted into an expression cassette, which is in turn inserted into an appropriate host cell system using any of the techniques commonly known to those of skill in the art, the ability of the fragment to regulate the expression of the reporter gene is assessed. By using a quantitative reporter assay and analyzing a series of DNA fragments of decreasing size, for example produced by convenient restriction endonuclease sites, or through the actions of enzymes such as BAL31, *E. coli* exonuclease III or mung bean nuclease, and which overlap each other a specific number of nucleotides, one may determine both the size and location of the native regulatory unit.

Of course once the core regulatory unit has been determined, one may choose to modify the regulatory unit by mutating certain nucleotides within the core unit. The effects of these modifications may be analyzed using the same reporter assay to determine whether the modifications either enhance or reduce transcription. Thus key nucleotides within the core regulatory sequence can be identified.

It is recognized that regulatory units often contain both elements that either enhance or inhibit transcription. In the case that a regulatory unit is suspected of containing both types of elements, one may use competitive DNA mobility shift assays to separately identify each element. Those of skill in the art will be familiar the use of DNA mobility shift assays.

It may also be desirable to modify the identified regulatory unit by adding additional sequences to the unit. The added sequences may include additional enhancers, promoters or even other genes. Thus one may, for example, prepare a DNA fragment that contains the native regulatory elements positioned to regulate one or more copies of the native gene and/or another gene or prepare a DNA fragment that contains not one but multiple copies of the promoter region such that transcription levels of the desired gene are relatively increased.

Turning to the expression of the *Coccidioides* spp. peptide, once a suitable clone or clones have been obtained, one may proceed to prepare an expression system. The engineering of DNA segment(s) for expression in a prokaryotic or eukaryotic system may be performed by techniques known to those of skill in recombinant expression. It is believed that virtually any expression system may be employed in the expression of the proteins of the present invention.

In expression, one will typically include a polyadenylation signal to effect proper polyadenylation of the transcript. The nature of the polyadenylation signal is not believed to be crucial to the successful practice of the invention, and any such sequence may be employed. The SV40 polyadenylation signal is convenient and is known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals may be used. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

The *Coccidioides* spp. peptides of the present invention may be co-expressed with any other protein or peptide, such as another *Coccidioides* spp. antigen. Co-expression may be achieved by co-transfecting the cell with two distinct recombinant vectors, each bearing a copy of either the respective DNA. Alternatively, a single recombinant vector may be constructed to include the coding regions for both of the proteins, which could then be expressed in cells transfected with the single vector. In either event, the term "co-expression" herein refers to the expression of the *Coccidioides* spp. peptide with another protein or peptide in the same recombinant cell.

As used herein, the terms "engineered" and "recombinant" cells refer to a cell into which an exogenous nucleic acid or DNA segment has been introduced. Therefore, engineered cells are distinguishable from naturally occurring cells, which do not contain a recombinantly introduced exogenous nucleic acid or DNA segment. Engineered cells are thus cells having a nucleic acid or DNA segment introduced through the hand of man. Recombinant cells also include those having an introduced nucleic acid or DNA segment positioned adjacent to a promoter not naturally associated with the particular introduced nucleic acid or DNA segment. Recombinant cells of the present invention also include those in which the *Coccidioides* spp. peptide-encoding sequences have been removed, i.e., "knock-outs".

To express a recombinant *Coccidioides* spp. peptide in accordance with the invention one would prepare an expression vector that comprises a *Coccidioides* spp. peptide-encoding nucleic acid under the control of one or more promoters. To bring a coding sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as E. coli, fungi and yeast transformed with recombinant bacteriophage DNA, plasmid DNA or cosmid DNA expression vectors.

Certain examples of prokaryotic hosts are E. coli strain RR1, E. coli LE392, E. coli B, E. coli X 1776 (ATCC No. 31537) as well as E. coli W3110 (F-, lambda-, prototrophic, ATCC No. 273325); bacilli such as Bacillus subtilis; and other enterobacteriaceae such as Salmonella typhimurium, Serratia marcescens, and various Pseudomonas species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector that can be used to transform host cells, such as E. coli LE392.

Further useful vectors include pIN vectors; and pGEX vectors, for use in generating glutathione S-transferase (GST) soluble fusion proteins for later purification and separation or cleavage. Other suitable fusion proteins are those with β-galactosidase, ubiquitin, and the like.

Promoters that are most commonly used in recombinant DNA construction include the β-lactamase (penicillinase), lactose and tryptophan (tip) promoter systems. While these are the most commonly used, other microbial promoters have been discovered and utilized, and details concerning their nucleotide sequences have been published, enabling those of skill in the art to ligate them functionally with plasmid vectors.

The following details concerning recombinant protein production in bacterial cells, such as E. coli, are provided by way of exemplary information on recombinant protein production in general, the adaptation of which to a particular recombinant expression system will be known to those of skill in the art.

Bacterial cells, for example, E. coli, containing the expression vector are grown in any of a number of suitable media. The expression of the recombinant protein may be induced, e.g., by adding IPTG to the media (if an inducible expression construct is used) or by switching incubation to a higher temperature. After culturing the bacteria for a further period, generally of between 2 and 24 hours, the cells are collected by centrifugation and washed to remove residual media.

The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents, such as β-mercaptoethanol or DTT (dithiothreitol).

Under some circumstances, it may be advantageous to incubate the protein for several hours under conditions suitable for the protein to undergo a refolding process into a conformation that more closely resembles that of the native protein. Such conditions generally include low protein concentrations, less than 500 mg/ml, low levels of reducing agent, concentrations of urea less than 2 M and often the presence of reagents such as a mixture of reduced and oxidized glutathione which facilitate the interchange of disulfide bonds within the protein molecule.

The refolding process can be monitored, for example, by SDS-PAGE, or with antibodies specific for the native molecule (which can be obtained from animals vaccinated with the native molecule or smaller quantities of recombinant protein). Following refolding, the protein can then be purified further and separated from the refolding mixture by chromatography on any of several supports including ion exchange resins, gel permeation resins or on a variety of affinity columns.

For expression in Saccharomyces, the plasmid YRp7, for example, is commonly used. This plasmid already contains the trp1 gene, which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the particular coding sequences.

In a useful insect system, *Autograph californica* nuclear polyhedrosis virus (AcNPV) is used as a vector to express foreign genes. The virus grows in *Spodoptera frugiperda* cells. The *C. immitis* peptide coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051, incorporated herein by reference).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications and processing (e.g., cleavage) of protein products may be important for the function of the protein.

Different host cells have characteristic and specific mechanisms for the post-translational processing and modification of proteins. Appropriate cells lines or host systems can be chosen to ensure the correct modification and processing of the foreign protein expressed.

Expression vectors for use in mammalian such cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient. The promoters may be derived from the genome of mammalian cells (e.g., metallothionein promoter) or from mammalian viruses (e.g., the adenovirus late promoter; the vaccinia virus 7.5K promoter).

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment that also contains the SV40 viral origin of replication. Smaller or larger SV40 fragments may also be used, provided there is included the approximately 250 bp sequence extending from the HindIII site toward the BglI site located in the viral origin of replication.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant *Coccidioides* spp. peptides, stable expression may be used and cell lines that stably express the *Coccidioides* spp. peptides may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex virus thymidine kinase, hypoxanthine-guanine phosphoribosyltransferase and adenine phosphoribosyltransferase genes, in tk-, hgprt- or aprt-cells, respectively. Also, antimetabolite resistance can be used as the basis of selection for dhfr, which confers resistance to methotrexate; gpt, which confers resistance to mycophenolic acid; neo, that confers resistance to the aminoglycoside G-418; and hygro, which confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

It is contemplated that the *Coccidioides* spp. peptides of the invention may be "overexpressed", i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural cells is indicative of overexpression, as is a relative abundance of the specific protein in relation to the other proteins produced by the host cell and, e.g., visible on a gel.

The following examples are included to demonstrate certain preferred embodiments of the invention. It will be appreciated by those of skill in the art that the compositions and techniques disclosed in the examples that follow represent compositions and techniques discovered by the inventor to function well in the practice of the invention, and thus can be considered to constitute certain preferred modes for its practice. However, those of skill in the art should, in light of the present disclosure, appreciate that many changes can be made in the specific embodiments that are disclosed and still obtain a like or similar result without departing from the spirit and scope of the invention.

Example I

Use of Expression Library Immunization to Identify Protective Antigen

The present example describes the successful use of cDNA expression library immunization (ELI) to identify a new protective antigen from the fungal pathogen, *C. immitis*. The antigen identified, ELI-Ag1, may be used as a vaccine, or within a multivalent vaccine, for Coccidioidomycosis and Valley Fever.

A. Materials and Methods

1. Organism

*C. immitis* strain Silveira was maintained in vitro on 2% glucose-1% yeast-extract agar plates for 4 to 6 wks at room temperature. Virulence of the isolate was preserved by sequential in vivo passes through mice. Arthroconidia were harvested in sterile, pyrogen-free saline, filtered through a sterile rayon column to remove hyphal fragments, washed twice in saline and enumerated by hemacytometer counts. The viability of the inocula was confirmed by plate counts on 2% glucose-1% yeast extract agar. All procedures with live fungus and infected tissues were performed within a certified Biosafety Level 3 laboratory.

2. Library Creation

First-generation spherules were grown by culturing arthroconidia in RPMI 1640 medium with 10% fetal bovine sera for 36 hrs. at 37° C. with 20% $CO_2$ on a gyratory shaker (180 rpm). The spherules were collected by centrifugation at 450×g for 15 min. and washed 3 times in diethyl pyrocarbonate-treated phosphate buffered saline. The cell pellets were collected and resuspended in lysis buffer (200 mM Tris pH 7.6, 0.5 M NaCl, 10 mM EDTA) to approximately $4\times10^6$ cells per ml.

The spherules were disrupted in a Mini Bead-beater (Biospec Products, Bartlesville, Okla.) and the total RNA was isolated by a phenol-chloroform extraction followed by ethanol precipitation. From 1 mg total RNA, approximately 100 μg poly(A)$^+$ RNA was isolated and reverse transcribed using MMLV reverse transcriptase and the primer of SEQ ID NO:23:

5'-GAGAGAGAGAGAGAGAGAGAGAAC-TAGTCTCGAGTTTTTTTTTTTTTTTTTT-3'.

The cDNA was size fractionated on a Sepharose CL-2B gel filtration column to remove excess XhoI linker-primers Zap cDNA Synthesis and Zap-cDNA Gigapack III Gold Cloning Kit, Stratagene, La Jolla Calif.). Approximately 925 ng of cDNA was ligated into the unidirectional cloning Lambda ZAP Express vector, and packaged into Lambda bacteriophage particles using Gigapack III Gold in vitro packaging extract (Stratagene).

The unamplified phage library ($1.5\times10^6$ total pfu) was used to create 15 pools, each containing 100 plaques. These were plated and hybridized with a probe for Ag2/PRA by Southern analysis in order to identify and remove Ag2/PRA clones. Twelve of the 15 pools were negative for Ag2/PRA. Lambda phage were eluted from these plates by gentle rocking overnight in a 5 ml suspension medium (100 mM NaCl, 8 mM $MgSO_4$, 0.01% gelatin, 50 mM Tris (pH 7.5) at 4° C. The titer of the resulting Lambda phage suspensions was between 1.98 and $6.06\times10^7$ total PFU. Samples of each pool were aliquoted and cryopreserved at −80° C.

3. Preparation of DNA for Genetic Immunization and Pool Fractionation

Ten of the 12 sibling library pools that did not contain the Ag2/PRA gene were evaluated for their protective capacity in mice. For the first two studies, Lambda phage genomic DNA was converted into the pBK-CMV phagemid vector in the XLOLR indicator strain of *Escherichia coli* (Stratagene) via in vivo mass excision using the ExAssist helper phage (Stratagene). The reactions were plated at a density of 5 to $6\times10^3$ cfu per 150 mm plate containing Luria-Bertani (LB) medium with kanamycin (50 μg/ml) and grown for 24 h at 37° C. Bacterial lawns from a set of 25-30 plates (each set representing an individual cDNA pool) were harvested, suspended in liquid LB-kanamycin medium, and pelleted by centrifugation. Plasmid DNA was harvested from bacterial pellets with the Qiagen EndoFree Plasmid Giga Kit (Valencia, Calif.), quantitated spectrophotometrically, and adjusted to 2.0 mg/ml in sterile pyrogen-free saline for injection (Baxter Healthcare, Deerfield, Ill.). Levels of endotoxin were less than 20 units per 100 μg DNA, as measured by the *Limulus Amebocyte* Lysate (Cambrex Corporation, East Rutherford, N.J.).

4. Immunization and Infection

Female BALB/c mice, 5 wks of age, were purchased from Jackson Laboratories (Bar Harbor, Me.) and given food and water ad libitum. Just before immunization, the mice were anesthetized by an intramuscular injection of 0.1 ml of a mixture of ketamine (30 mg/ml) and xylazine (4 mg/ml). Genetic immunization was performed as described by Jiang et al. (1999a; specifically incorporated herein by reference).

For the first and second screen, groups of 10 mice were injected intramuscularly (i.m.) with 100 μl of DNA (200 μg) in the tibialis anterior muscle in a site which had been treated with Nair (Carter-Wallace, Inc., New York, N.Y.) on the day before. The injections were repeated at 3 wk intervals, for a total of 3 immunizations. For the third and forth level screen, mice were also given an intradermal (i.d.) injection of plasmid DNA in 30 μl of physiologic saline. The i.d. immunization was given in the pinnae of the ear of the mice 2 wks after the last i.m. injection. In all cases, 4 wks after the last intramuscular injection, the animals were challenged with approximately 2,500 arthroconidia via the intraperitoneal (i.p.) route. This dose represents a 54 $LD_{50}$ for BALB/c mice by this route of challenge (Kirkland and Fierer, 1983). Control mice received identical injections with vector alone.

Animals were monitored daily for mortality over a 35 to 40 day period post-challenge. Survivors were sacrificed, their lungs and spleens were gently homogenized in sterile plastic bags (Whirlpak; American Scientific Products, Dallas, Tex.) containing 2 ml of saline, and 0.5 ml of the homogenized tissues were plated on Mycobiotic medium (Difco Laboratories, Detroit, Mich.). Any survivors that did not show any positive cultures were eliminated from analysis since, in previous studies, mice do not clear an infection with 2,500 arthroconidia within 40 days, even after being vaccinated with the FKS vaccine or Ag2/PRA (Jiang et al., 1999a; 1999b). The data presented represent survivors that were culture positive for C. Immitis.

5. Statistical Analyses

Comparison of survival curves was accomplished using the Kaplan-Meier procedure. Probability values of <0.05 were considered significant.

B. Results

1. First-Level Screening

The first-level screening of the cDNA-ELI library was conducted in two separate trials, each with 10 BALB/c mice per pool. The combined results obtained in the two separate studies are depicted in FIG. 1. Of the 10 sibling pools, each containing between 80 and 100 genes, two showed a highly significant level of protection. Fifty nine percent of mice immunized with Pool 7 survived the 35 days period post-challenge and 50% of mice immunized with Pool 8 survived, whereas none of the mice immunized with the pBK-CMV vector alone survived (P<0.001 for both pools). Lower levels of protection were obtained with Pool 1 (P<0.01), Pool 2 (P<0.01), Pool 3 (P<0.05), Pool 4 (P<0.05), Pool 6 (P<0.01), and Pool 10 (P<0.005). Pool 5 was nonprotective.

2. Second-Level Screening

Since Pool 7 was the most protective, emphasis was given to identifying the protective component(s) in this pool. Fractionation of the pool into 5 subpools was performed by plating the corresponding in vivo excision reaction onto the XLOLR indicator strain of *E. coli* and randomly picking 360 individual colonies (representing approximately 3-fold coverage of the original 100 pfu). Individual colonies were grown overnight in 3 ml of LB-kanamycin medium and screened for the presence of cDNA inserts by restriction digestion of isolated plasmid DNA using EcoRI and XhoI. In addition, 0.5 ml was plated onto a 150 mm plate containing LB-kanamycin medium and an aliquot of each culture was also stored at −80° C. as a 12% DMSO stock. Out of the 360 clones, 297 contained inserts and were chosen for subsequent testing and, to ensure multiple representations within cDNA subpools, approximately 60 genes were randomly assigned into each of 5 pools. Bacterial lawns from the 60 LB-kanamycin plates, each plate representing a single clone, were grown overnight, mixed together, and the plasmid DNA was isolated as described below to create subsequent pools.

Groups of 10 BALB/c mice were immunized with the cDNA subpools, which were designated Pools 7-1, 7-2, 7-3, 7-4, and 7-5, and 28 days after the last of three i.m. immunizations, the mice were challenged with 2,625 viable arthroconidia via the i.p. route. The results established that 56% of the mice immunized with Pool 7-3 survived the 40 day period postinfection (FIG. 2), whereas none of the vector control mice survived (P<0.001). A lower level of protection was observed in Pool 7-5 (P<0.01) whereas none of the remaining pools provided any significant protection over 40 day period postinfection.

3. Third-Level Screening

In order to examine further the protective capacity of the 60 genes representing Pool 7-3, a third-level screening was conducted, wherein Pool 7-3 was fractionated into 6 sublibraries, each containing 10 clones. This was accomplished by first transforming each individual plasmid DNA from each of the 60 clones identified in the second level screening into *E. coli* DH5a. Single colony isolates of each of these 60 *E. coli* DH5α strains were inoculated into 5 ml of LB-kanamycin medium, grown overnight, and 0.5 ml of each culture was plated separately onto each of 3 large LB-kanamycin plates. Six cDNA subpools were then created, each containing 10 genes.

Immunization of mice was performed as above, except that mice were given an additional 60 μg of plasmid DNA in 30 μl of pyrogen-free saline via an i.d. injection in the pinnae of the ear 2 wks after the last i.m. injection. Two wks later, the mice were challenged with 2,340 viable arthroconidia via the i.p. route. Both the original Pool 7 and the derived Pool 7-3 were included for comparison. Of the 6 sublibraries from Pool 7-3, only Pool 7-3-5 induced a significant level of protection when compared to vector control mice (P<0.0001) (FIG. 3).

4. Fourth-Level Screening

DNA was prepared from each of the 10 individual clones used to prepare Pool 7-3-5. Groups of 10 BALB/c mice were used and the mice receiving the 7-3-5 pool received three i.m. injections of 200 μg DNA at 3 wk intervals, followed by an i.d. immunization with 60 μg in the pinnae of the ear 2 wks later. The mice were challenged with 2,340 arthroconidia 2 wks later. Of the 10 individual clones, the highest level of protection was obtained with clone 7-3-5-5 (P<0.0001), with a survival in 8 of 10 mice at day 40 postinfection (FIG. 4). This level of protection was slightly less than the 100% survival induced in mice immunized with the 7-3-5 pool, but the difference was not statistically significant. Four other clones in the 7-3-5 pool also induced protection, but at a much lower level. These were clones 7-3-5-1 (P<0.05), 7-3-5-2 (P<0.05), 7-3-5-3 (P<0.02), and 7-3-5-7 (P<0.05). The fact that Pool 7-3-5 contained these weakly protective clones, as well as clone 7-3-5-5 likely accounted for its slightly increased level of protection as compared with 7-3-5-5 alone.

Example II

Characterization of New Protective Antigen, ELI-Ag1

This example concerns the sequencing and characterization of ELI-Ag1, a highly protective antigen identified from *C. immitis* using the ELI technique. Features of the antigen sequence are described with reference to immunological considerations.

A. Methods of DNA Sequencing and Sequence Analyses

DNA sequence analysis was performed by Lark Technologies, Inc. (Houston, Tex.). The nucleotide sequence of the entire gene and flanking sequences upstream and downstream of the start codon were determined for both strands. Comparisons of the predicted protein sequence with protein sequences in the available databases and pairwise protein alignments were done using PSI-BLAST at the server of the National Center for Biotechnology Information at the National Library of Medicine (Altschul et al., 1997).

The molecular weight, isoelectric point, and motif searches were determined using programs available at Scansite (http://scansite.mit.edu). Hydropathy analysis was performed using the Kyte-Doolittle analysis (Kyte and Doolittle, 1982) present in DNASTAR (DNASTAR, Inc., Madison, Wis.). Antigenic peptides were determined using the method of Kolaskar and Tongaonkar (1990). Prediction of peptide motifs binding to MHC class I or II molecules was made using the RANKPEP program (Reche et al., 2002). Analysis of protein domains having putative functional groups was performed using PROSITE (Falquet et al., 2002).

B. Results

1. Sequencing of the Protective 7-3-5-5 Clone

Nucleic acid sequencing of the protective 7-3-5-5 clone identified a 1,080 bp insert, containing a 5' untranslated region comprised of 142 bp, a 672 bp ORF, and a 3' untranslated region containing 266 bp. The nucleotide sequence is SEQ ID NO:1 and the deduced amino acid sequence is SEQ ID NO:2.

The deduced primary translation product of the 672 bp ORF has 224 amino acids and, in the absence of any post-translational modification, has a predicted molecular mass of 23.2 kDa and an isoelectric point of 5.22. Sequence comparisons using PSI-BLAST showed that the 7-3-5-5 gene shares a 28% identity with 41% of the amino acids in a hypothetical protein (B24B19.340) from the filamentous fungus *Neurospora crassa*. Amino acid sequence analyses showed that the N-terminus contains a putative 19 amino acid signal sequence, with a potential cleavage site between positions 19 and 20, and a 15 amino acid C-terminal putative glycosyl phosphatidylinositol (GPI) anchor site.

2. Characterization of the Protective 7-3-5-5 Clone

Computational algorithms were used to predict the hydropathy, antigenic index, secondary structure, antigenic peptides and possible binding of peptide motifs to MHC molecules. The hydrophobicity plot showed two major hydrophobic regions, corresponding to the putative N-terminal signal sequence and the C-terminal GPI signal peptide. Antigenic analyses predicted that the translated 224 amino acid protein contains 10 antigenic determinants and 10 peptides that are predicted to bind to MHC Class I or Class II molecules (Table 1).

TABLE 1

Feature Analysis

| Feature | Start position | Sequence | End position | SEQ ID NO: |
|---|---|---|---|---|
| Antigenic determinants | 4 | SGIVFAFSALISLSTAHFRLVDP | 26 | 3 |
|  | 37 | TRFPCCG | 43 | 4 |
|  | 49 | SRTSVSL | 55 | 5 |
|  | 69 | DQTAVQVLLALGS | 81 | 6 |
|  | 88 | NITLVPTRFQVGLGDFCLPSVSLD | 111 | 7 |
|  | 113 | QRLGVKP | 119 | 8 |
|  | 125 | ATLQVVT | 131 | 9 |
|  | 138 | GLYNCADI | 145 | 10 |
|  | 151 | TEYTVPSS | 158 | 11 |
|  | 209 | TWGVLGAIVVGG | 220 | 12 |
| MHC Class I binding motifs[†] | 84 | GSNFNITLV | 92 | 13 |
|  | 157 | SSCKNGTGV | 165 | 14 |
|  | 137 | GGLYNCADI | 145 | 15 |
|  | 174 | AATRNANES | 182 | 16 |
|  | 147 | FSSTTEYTV | 155 | 17 |
| MHC Class II binding motifs[†] | 10 | FSALISLST | 18 | 18 |
|  | 147 | FSSTTEYTV | 156 | 19 |
|  | 170 | FSGEAATRN | 178 | 20 |
|  | 73 | VQVLLALGS | 81 | 21 |
|  | 46 | MSKSRTSVS | 54 | 22 |

[†]Listed in order of decreasing percentile score of the predicted peptide

Predictions of functional domains include two protein kinase C phosphorylation sites (94-96 and 158-160), five casein kinase II phosphorylation sites (54-57, 56-59, 109-112, 131-134, and 149-152), and overlapping N-myristoylation sites (5-10, 43-48, 80-85, 84-89, 122-17, 137-142, 138-143, 162-167, 191-196, 194-100, and 211-216). Four sites are potentially N-glycosylated (88-91, 124-127, 161-164, and 180-183) and four threonine residues may be O-glycosylated (37, 166, 174, and 195). A Scansite motif search revealed a chitin-binding domain from amino acids 141 through 155.

Example III

Immunization with Recombinant ELI-Ag1 Protects Against *Coccidioides* Infection

The present example shows that immunization with recombinant ELI-Ag1 provides significant protection against lethal *Coccidioides* challenge. ELI-Ag1 was expression in *E. coli* and the recombinant protein purified. Animals immunized with recombinant ELI-Ag1 were significantly protected against lethal *Coccidioides* challenge as compared to animals treated with the adjuvant system alone.

A. Methods

Recombinant ELI-Ag1 was produced by PCR™ cloning of the ELI-Ag1 open reading frame into pPROHTb to create a HIS-tagged protein to aid in purification. This vector was transformed into *E. coli* strain DH5α and the recombinant protein purified from cell lysates of induced bacteria. The recombinant protein was purified over nickel columns and the purity was assessed by SDS page and Western blot analysis.

Mice were immunized with 5 micrograms of recombinant ELI-Ag1 admixed with a dual adjuvant of 10 micrograms of CpG deoxynucleotides in Freund's incomplete adjuvant in a total volume of 0.2 ml. There were a total of three injections given subcutaneously at intervals of three weeks. The control animals were injected with adjuvant alone. Two weeks after the last immunization, mice were challenged intraperitoneally with 2,500 arthroconidia of *C. posadasii* and the mice were monitored for mortality.

B. Results

Figure 5:
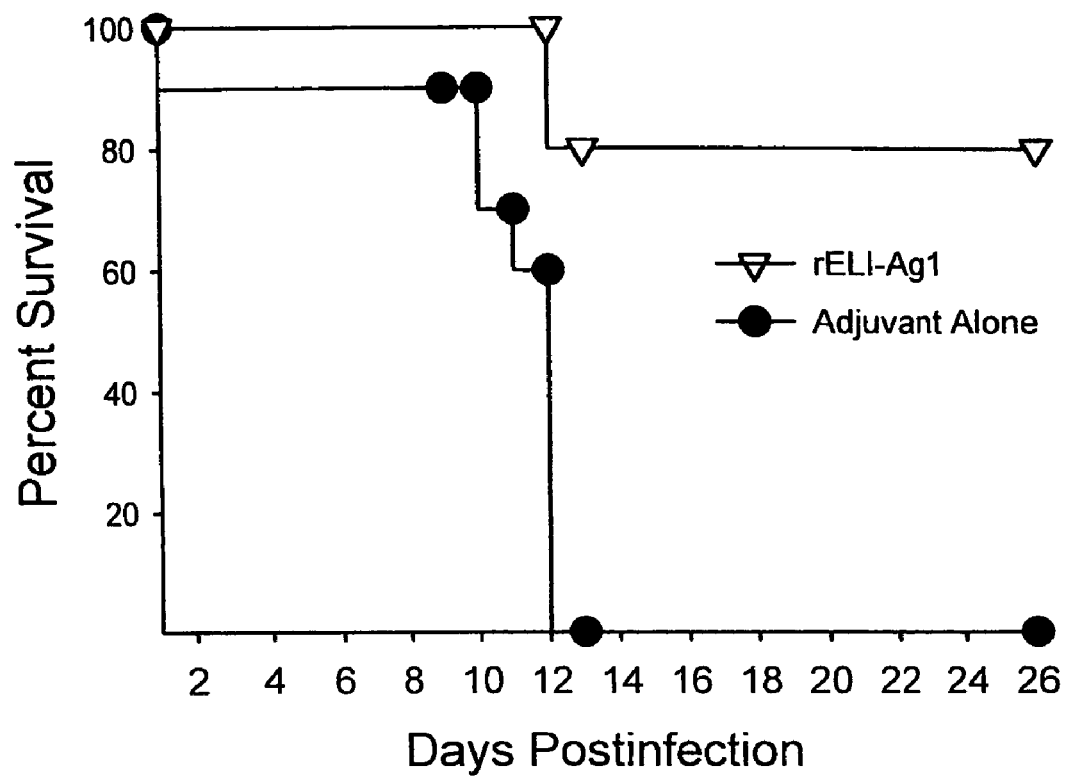
FIG. 5. Protection against *Coccidioides* infection by immunization with recombinant ELI-Ag1. ELI-Ag1 was expressed as a HIS-tagged protein in *E. coli* and the recombinant protein purified using nickel columns. Mice were immunized with 5 µg of recombinant ELI-Ag1 (Λ) admixed with a dual adjuvant (CpG deoxynucleotides in Freund's incomplete adjuvant), or with the dual adjuvant alone as a control (●). Two weeks after the last immunization, mice were challenged intraperitoneally with 2,500 arthroconidia of *C. posadasii* and the mice were monitored for mortality.

In this study, the control animals began to succumb at day 9 post challenge, and by day 13 there were no surviving animals. In contrast, to date (day 26 post challenge) only two ELI-Ag1-immunized animals have succumbed and the survivors are recovering and beginning to appear healthy. Statistical analysis of the survival curves by a log-rank method (Mantel-Haenszel analysis) revealed significant protection ($P<0.0017$) is conferred by immunization with ELI-Ag1 (FIG. 5).

Example IV

ELI-Ag1 Genetic Immunization Protects Against *Coccidioides* Pulmonary Challenge In addition to the protection against lethal *Coccidioides* challenge using the purified recombinant protein, the present example shows that genetic immunization with a vector expressing ELI-Ag1 provides protection against pulmonary challenge with *Coccidioides*. Genetic immunization of animals with ELI-Ag1 provided significant protection against lethal *Coccidioides* challenge via the pulmonary route, in controlled studies versus animals treated with the vector alone.

C57B1/6 mice were immunized at 3 week intervals with 50 µg of DNA from the pBKCMV vector alone or from the pBKCMV vector containing and expressing ELI-Ag1. Genetic immunization of the mice with ELI-Ag1 resulted in a significantly delayed mortality (p<0.036 Mantel) after pulmonary challenge with 34 arthroconidia.

Example V

ELI-Ag1-Ag2/PRA Combination Vaccine Protects Against *Coccidioides* Challenge

The present example shows that genetic immunization with a combination of ELI-Ag1 and Ag2/PRA results in higher final survival after pulmonary challenge with *Coccidioides*.

ELI-Ag1 protects against pulmonary challenge with *Coccidioides* when provided as a genetic immunization (e.g., see Example IV). Genetic immunization studies using a multivalent vaccine were first performed by combining ELI-Ag1 and Antigen-2 Proline Rich Antigen (Ag2/PRA) genes. In these studies, C57B1/6 mice were immunized at 3 week intervals with (1) 50 µg of DNA from: the pBKCMV vector alone; (2) the vector containing Ag2/PRA; (3) the vector containing ELI-Ag1; or (4) the combination of both genes ligated to the vector.

Figure 6:
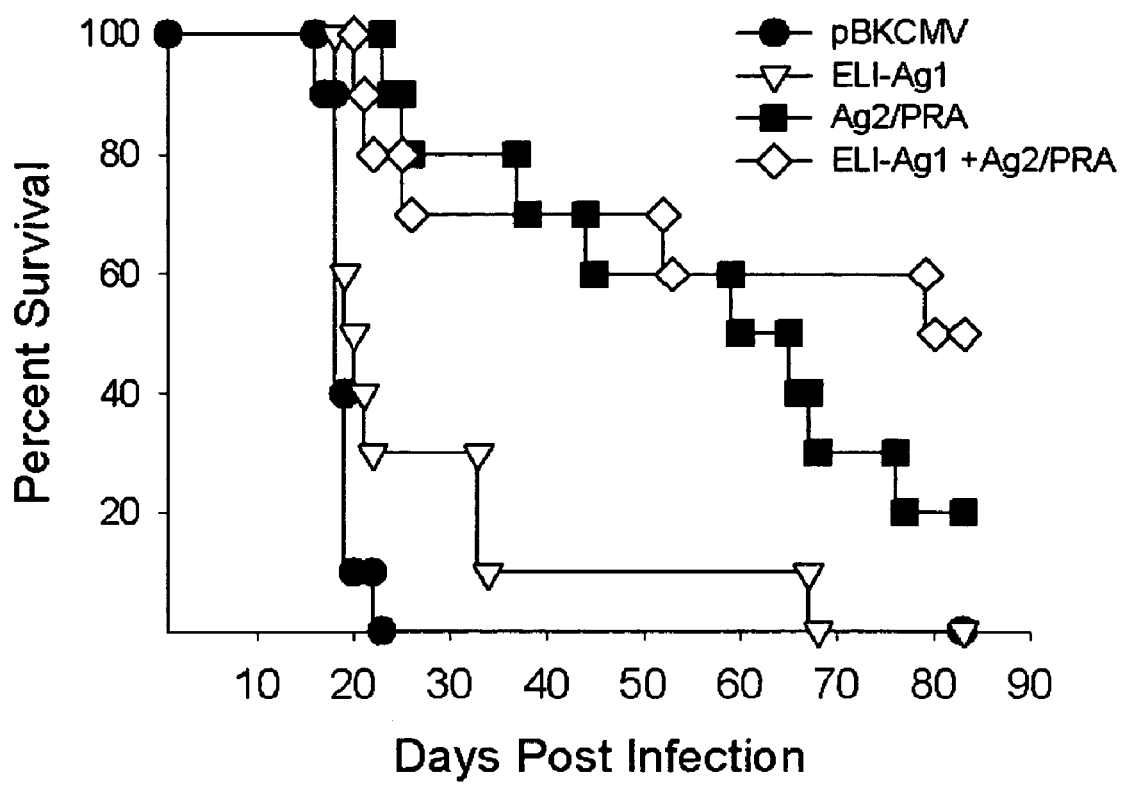
FIG. 6. Increased protection against pulmonary challenge with *Coccidioides* by genetic immunization with a combination of ELI-Ag1 and Ag2/PRA. C57B1/6 mice were immunized at 3 week intervals with 50 µg of DNA from: the pBKCMV vector alone as a negative control (●); the vector expressing the Ag2/PRA antigen (■); the vector expressing the ELI-Ag1 antigen (Λ); or the vector containing a combination of both genes ligated in the vector (◊). Mice from each group were then subject to pulmonary challenge with 34 arthroconidia and the mortality/survival determined.

As shown in FIG. 6, C57B1/6 mice immunized with ELI-Ag1 resulted in a significant delay in the mortality after pulmonary challenge with 34 arthroconidia (p<0.036 Mantel). Immunization with Ag2/PRA also resulted in a significantly delayed mortality (p<0.001, Mantel). Further, there was an increase in survival provided by a combined immunization with Ag2/PRA and ELI-Ag1 (50% vs. 20% for the combination vs. Ag2/PRA alone at day 83), although this was not statistically significant.

Example VI

ELI-Ag1 Adds Significant Protection to a Multivalent Vaccine

The increased survival observed following genetic immunization with a combination of ELI-Ag1 and Ag2/PRA (FIG. 6; Example IV), prompted further co-immunization studies. The results in the present example show that the addition of ELI-Ag1 to an Ag2/CSA fusion protein antigen results in a significant increase in protection against pulmonary challenge with *Coccidioides*.

One of the antigens employed in these studies is a fusion protein of Ag2/PRA and *Coccidioides*-specific Antigen (CSA) termed Ag2/CSA. The Ag2/CSA fusion protein was expressed in *Saccharomyces* and the fusion protein used in these studies was obtained from Dr. John Galgiani (***). The ELI-Ag1 antigen was expressed in *E. coli*. BALB/c mice were immunized with 1 µg Ag2/CSA fusion protein, 1 µg ELI-Ag1, or 1 µg of a combination of both antigens, all in CPG/IFA adjuvant or with CPG/IFA adjuvant alone (negative control).

Figure 7:
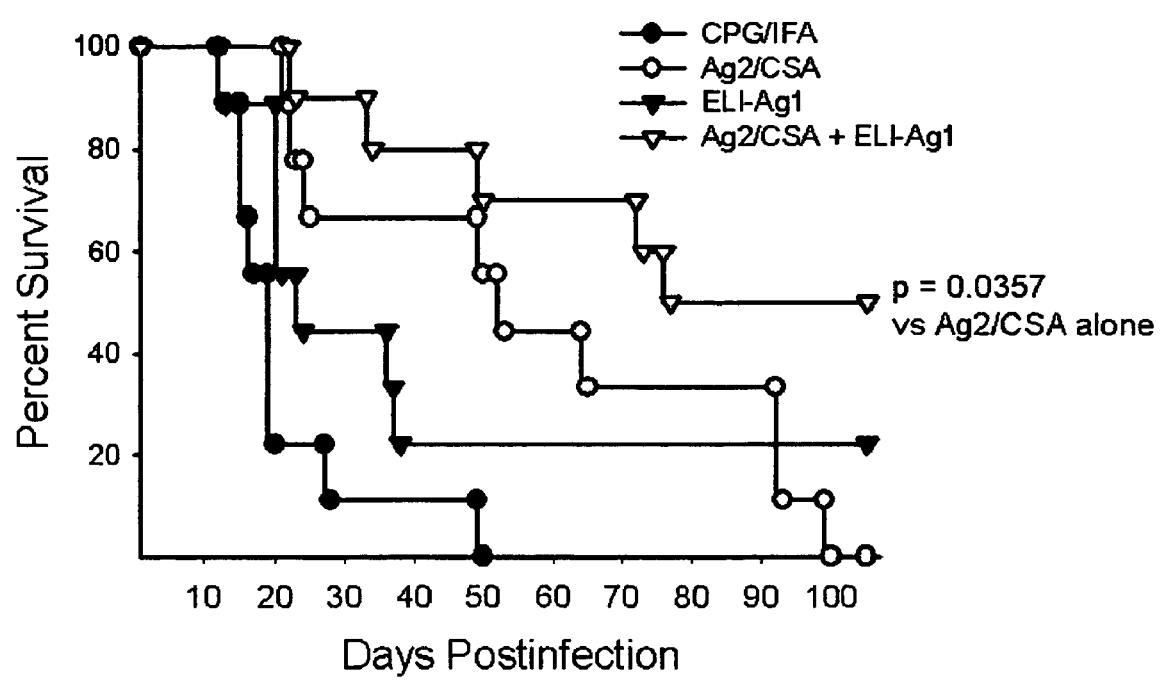
FIG. 7. Synergistic increase in protection against pulmonary challenge with *Coccidioides* by addition of ELI-Ag1 to an Ag2/CSA fusion protein. BALB/c mice were immunized with 1 µg of a fusion protein of Ag2/PRA and *Coccidioides*-specific Antigen (CSA) (Ag2/CSA antigen, expressed in *Saccharomyces*) in CPG/IFA adjuvant (o); 1 µg of ELI-Ag1 antigen (expressed in *E. coli*) in CPG/IFA adjuvant (Λ); 1 µg of a combination of both antigens in CPG/IFA adjuvant (Λ); or CPG/IFA adjuvant alone as a negative control (●). Mice from each group were then subject to pulmonary challenge with arthroconidia and the mortality/survival determined.

As shown in FIG. 7, Ag2/CSA and ELI-Ag1, when used individually, provided significant protection as compared to the adjuvant alone control. Using these recombinant proteins, the combination of ELI-Ag1 and Ag2/CSA resulted in a synergistic increase in protection. Although increased survival was observed following genetic immunization with a combination of ELI-Ag1 and Ag2/PRA (FIG. 6; Example IV), the increased protection from combined genetic immunization was not statistically significant. In contrast, the increase in protection resulting from the combined use of recombinant ELI-Ag1 and Ag2/CSA was statistically significant, with p=0.037 (Mantel) as compared to Ag2/CSA alone.

These results therefore show that utilization of ELI-Ag1 as part of a multivalent subunit vaccine results in increased protection against pulmonary challenge.

All of the compositions and methods disclosed and claimed herein can be made and executed without undue experimentation in light of the present disclosure. While the compositions and methods of this invention have been described in terms of certain preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abuodeh, Shubitz, Siege, "Resistance to *Coccidioides Immitis* in Mice after Immunization with Recombinant Protein or a DNA Vaccine of a Proline-Rich Antigen," *Infect. Immun.*, 67(6):2935-2940, 1999.

Altschul, Madden, Schaffer, "Gapped BLAST and PSI-BLAST: A New Generation of Protein Database Search Programs," *Nucleic Acids Res.*, 25:3389, 1997.

Ampel and Christian, "In vitro Modulation of Proliferation and Cytokine Production by Human Peripheral Blood Mononuclear Cells from Subjects with Various Forms of Coccidioidomycosis," *Infect. Immun.*, 65:4483-4487, 1997.

Azuma et al., "Correlation Between Augmented Resistance to Influenza Virus Infection and Histological Changes in Lung of Mice Treated with Trehalose-6,6'-dimycolate," *J. Biological Response Modifiers*, 7:473-482, 1988.

Baker et al., "Structural Features That Influence the Ability of Lipid A and Its Analogs To Abolish Expression of Suppressor T Cell Activity," *Infect. Immun.*, 60(7):2694-2701, 1992.

Barry, Lai, Johnston, "Protection Against *Mycoplasma* Infection Using Expression Library Immunization," *Nature*, 377(6550):632-635, 1995.

Beaman, Pappagianis, Benjamini, "Mechanisms of Resistance to Infection with *Coccidioides Immitis* in Mice," *Infect. Immun.*, 23(3):681-685, 1979.

Beaman, "Fungi Activation of Murine Macrophages by Recombinant Gamma Interferon," *Infect. Immun.*, 55(12):2951-2955, 1987.

Billetta et al., *Immunol. Lett.*, 73(2-3):269, 2000.

Bowness et al., "*Clostridium perfringens* enterotoxin is a superantigen reactive with human T cell receptors V beta 6.9 and V beta 22," *J. Exp. Med.*, 176(3):893-896, 1992.

Brayton, Vogel, Allsopp, "Expression Library Immunization to Identify Protective Antigens from *Cowdria Ruminantium*," *Ann. N.Y. Acad. Sci.*, 849:369-371, 1998.

Brutlag et al., *CABIOS*, 6:237-245, 1990.

Chou and Fasman, "Prediction of Protein Conformation," *Biochemistry*, 13(2):222-245, 1974a.

Chou and Fasman, "Conformational Parameters for Amino Acids in Helical, β-Sheet, and Random Coil Regions Calculated from Proteins," *Biochemistry*, 13(2):211-222, 1974b.

Chou and Fasman, "Prediction of the Secondary Structure of Proteins from Their Amino Acid Sequence," *Adv. Enzymol. Relat. Areas Mol. Biol.*, 47:45-148, 1978a.

Chou and Fasman, "Empirical Predictions of Protein Conformation," *Ann. Rev. Biochem.*, 47:251-276, 1978b.

Chou and Fasman, "Prediction of β-Turns," *Biophys. J*, 26:367-384, 1979.

Cox, Kennell, Boncyk, Murphy, "Induction and Expression of Cell-Mediated Immune Responses in Inbred Mice Infected with *Coccidioides Immitis,*" *Infect. Immun.*, 56:13-17, 1988.

Cox, "Coccidioidomycosis," *In: Fungal Infections and Immune Responses*, Murphy, Friedman and Bendinelli, Eds., Plenum Press, New York, pp. 173-211, 1993.

Cox et al., *J. Virol.*, 67(9):5664-5667, 1993.

Cox and Magee, "Protective Immunity in Coccidioidomycosis," *Res. Immunol.*, 149:417-428, 1998.

Cox and Magee, "Coccidioidomycosis: host response and vaccine development," *Clinical Microbiology Reviews*, 17(4):804-39, 2004.

Deavin et al., *Mol. Immunol.*, 33:145-55, 1996.

Delgado, Xue, Yu, Hung, Cole, "A recombinant beta-1,3-glucanosyltransferase homolog of *Coccidioides posadasii* protects mice against coccidioidomycosis," *Infect. Immun.*, 71(6)3010-9, 2003.

Dugger, Villareal, Nguyen, Zimmermann, Law, Galgiani, "Cloning and Sequence Analysis of the cDNA for a Protein from *Coccidioides Immitis* with Immunogenic Potential," *Biochem. Biophys. Res. Commun.*, 218:485-489, 1996.

Falquet, Pagni, Bucher, "The PROSITE Database, Its Status in 2002," *Nucleic Acids Res.*, 30:235-238, 2002.

Fetrow & Bryant, "New Programs for Protein Tertiary Structure Prediction," *Biotechnology*, 11:479-483, 1993.

Fisher, Koenig, White, "Molecular and Phenotypic Description of *Coccidioides Posadasii* sp. nov., Previously Recognized as the non-California Population of *Coccidioides Immitis,*" *Mycologia*, 94:73-84, 2002.

Franke, Sette, Sacci, Jr., Southwood, Corradin, and Hoffman, "A subdominant CD8+ cytotoxic T lymphocyte (CTL) epitope from the *Plasmodium yoelii* circumsporozoite protein induces CTLs that eliminate infected hepatocytes from culture," *Infect. Immun.*, 68:3403-3411, 2000.

Fynan et al., "DNA vaccines: Protective immunizations by parenteral, mucosal, and gene-gun inoculations," *Proc. Natl. Acad. Sci. USA*, 90:11478-11482, 1993.

Galgiani, "Coccidioidomycosis," *West J. Med.*, 159:153-171, 1993.

Hung, Ampel, Christian, Seshan, Cole, "A Major Cell Surface Antigen of *Coccidioides Immitis* which Elicits both Humoral and Cellular Immune Responses," *Infect. Immun.*, 68(2):584-593, 2000.

Jameson and Wolf, "The antigenic index: a novel algorithm for predicting antigenic determinants," *Comput. Appl. Biosci.*, 4:181-186, 1988.

Jiang, Magee, Quitugua, Cox, "Genetic Vaccination Against *Coccidioides Immitis*: Comparison of Vaccine Efficacy of Recombinant Antigen 2 and Antigen 2 DNA," *Infect. Immun.*, 67(2):630-635, 1999a.

Jiang, Magee, Cox, "Coadministration of Interleukin 12 Expression Vector with Antigen 2 cDNA Enhances Induction of Protective Immunity Against *Coccidioides Immitis,*" *Infect. Immun.*, 67(11):5848-5853, 1999b.

Kirkland and Fierer, "Inbred Mouse Strains Differ in Resistance to Lethal *Coccidioides Immitis* Infection," *Infect. Immun.*, 40:912-916, 1983.

Kirkland, Thomas Finley, Cole, "Immunogenicity of a 48-Kilodalton Recombinant T-Cell Reactive Protein from *Coccidioides Immitis*: Homology to 4-Hydroxyphenylpyruvate Dioxygenase and the Mammalian F Antigen," *Gene*, 161:107-111, 1995.

Kirkland, Thomas, Finley, Cole, "Immunogenicity of a 48-Kilodalton Recombinant T-Cell Reactive Protein of *Coccidioides Immitis,*" *Infect. Immun.*, 66(2):424-431, 1998.

Kirkland and Cole, "Coccidioidomycosis: Pathogenesis, Immune Response, and Vaccine Development," *In: Fungal Pathogenesis: Principles and Clinical Applications*, Calderone and Cihlar, Eds., Marcel Dekker, New York, pp 365-400, 2002.

Kolaskar and Tongaonkar, "A Semi-Empirical Method for Prediction of Antigenic Determinants on Protein Antigens," *FEBS Lett.* 276(1-2):172-174, 1990.

Kong, Levine, Smith, "Immunogenic Properties of Nondisrupted and Disrupted Spherules of *Coccidioides Iimmitis* in Mice," *Sabouraudia*, 2; 131-142, 1963.

Kyte and Doolittle, "A Simple Method for Displaying Hydropathic Character of a Protein," *J. Mol. Biol.*, 157: 105-132, 1982.

Lecara, Cox, Simpson, "*Coccidioides Iimmitis* Vaccine: Potential of an Alkali-Soluble, Water-Soluble Cell Wall Antigen," *Infect. Immun.*, 39:473-475, 1983.

Levine, Cobb, Smith, "Immunity to Coccidioidomycosis Induced in Mice by Purified Spherule, Arthrospore, and Mycelial Vaccines," *Trans. N.Y. Acad. Sci.*, 22:436-449, 1960.

Levine, Miller, Smith, "Influence of Vaccination on Respiratory Coccidioidal Disease in Cynomologous Monkeys," *J. Immunol.*, 89:242-251, 1962.

Levine, Pappagianis, Cobb, "Development of Vaccines for Coccidioidomycosis," *Mycopathol. Mycol. Appl.*, 41:177-185, 1970.

Li Yu, Hung, Lehmann, Cole, "Recombinant Urease and Urease DNA of *Coccidioides Immitis* Elicit an Immunoprotective Response against Coccidioidomycosis in Mice," *Infect. Immun.*, 69(5):2878-2887, 2001.

Magee and Cox, "Roles of gamma interferon and interleukin-4 in genetically determined resistance to *Coccidioides immitis,*" *Infect. Immun.*, 63:3514-3519, 1995.

Magee and Cox, "Interleukin-12 Regulation of Host Defenses Against *Coccidioides Immitis,*" *Infect. Immun.*, 64(9):3609-3613, 1996.

Maloy, Donachie, O'Hagan and Mowat, "Induction of mucosal and systemic immune responses by immunization with ovalbumin entrapped in poly(lactide-co-glycolide) microparticles," *Immunology*, 81:661-667, 1994.

Manoutcharian, Terrazas I, Gevorkian, Govezensky, "Protection Against Murine Cysticercosis using cDNA Expression Library Immunization," *Immunol. Ltrs.*, 62:131-136, 1998.

Manoutcharian, Terrazas, Gevorkian, Govezensky, "DNA Pulsed Macrophage-Mediated cDNA Expression Library Immunization in Vaccine Development," *Vaccine*, 18:389-391, 2000.

Melby, Ogden, Flores, "Identification of Vaccine Candidates for Experimental Visceral Leishmaniasis by Immunization with Sequential Fractions of a cDNA Expression Library," *Infect. Immun.*, 68(10):5595-5602, 2000.

Mooney et al., "Bacterial superantigen signaling via HLA class II on human B lymphocytes," *Mol. Immunol.*, 31(9): 675-681, 1994.

Moore, Lenghaus, Sheedy, Doran, "Improved Vectors for Expression Library Immunization—Application to *Mycoplasma Hyopneumoniae* Infection in Pigs," *Vaccine*, 20:115-120, 2000.

Myers et al., "Monophosphoryl Lipid A Behaves as a T-Cell-Independent Type 1 Carrier for Hapten-Specific Antibody Responses in Mice," *Infect. Immun.*, 63(1):168-174, 1995.

Pan and Cole, "Molecular and Biochemical Characterization of *Coccidioides immitis*-Specific (CS) Antigen," *Infect. Immun.*, 63:3994-4002, 1995.

Pappagianis, Levine, Smith, Berman, Kobayashi, "Immunization of Mice with Viable *Coccidioides Immitis*," *J. Immunol.*, 86:28-34, 1961.

Pappagianis and Levine, "The Present Status of Vaccination Against Coccidioidomycosis in Man," *Am. J. Epidemiol.*, 102:30-41, 1975.

Pappagianis, "Epidemiology of Coccidioidomycosis," *In: Coccidioidomycosis*, Ed., Stevens, Plenum Publishing Corp., New York, pp 63-85, 1980.

Pappagianis, "Marked increase in cases of coccidioidomycosis in California: 1991, 1992, and 1993," *Clin. Inf. Dis.*, 19:S14-18, 1994.

Parker, Bednarek, Coligan, "Scheme for ranking potential HLA-A2 binding peptides based on independent binding of individual peptide side-chains," *J. Immunol.*, 152:163, 1994.

Peng et al., "Localization within a proline-rich antigen (Ag2/PRA) of protective antigenicity against infection with *Coccidioides immitis* in mice," *Infect. Immun.*, 70(7): 3330-5, 2002.

Piedrafita, Xu, Hunter, Harrison, Liew, "Protective Immune Responses Induced by Vaccination with an Expression Library Genomic Library of *Leishmania Major*," *J. Immunol.*, 163(3):1467-1472, 1999.

Putney and Burke, "Improving protein therapeutics with sustained-release formulations," *Nature Biotechnol.*, 16:153-157, 1998.

Rabinovich et al., "Vaccine Technologies: View to the Future," *Science*, 265:1401-1402, 1994.

Ravindranath et al., "Efficacy of tumor cell vaccine after incorporating monophosphoryl lipid A (MPL) in tumor cell membranes containing tumor-associated ganglioside," *Experientia*, 50:648-653, 1994a.

Ravindranath et al., "Attachment of Monophosphoryl Lipid A (MPL) to Cells and Liposomes Augments Antibody Response to membrane-bound Gangliosides," *J. Autoimmunity*, 7:803-816, 1994b.

Reche, Glutting, Reinherz, "Prediction of MHC Class I Binding Peptides Using Profile Motifs," *Human Immunol.*, 63:701-709, 2002.

Restifo, Bacik, Irvine, Yewdell, McCabe, Anderson, Eisenlohr, Rosenberg, Bennink, "Antigen processing in vivo and the elicitation of primary CTL responses," *J. Immunol.*, 154:4414-4422, 1995.

Rothbard and Taylor, *EMBO J.*, 7:93-100, 1988.

Rott et al., "Protection from experimental allergic encephalomyelitis by application of a bacterial superantigen," *Int. Immunol.*, 4(3):347-353, 1992.

Sambrook et al., *Molecular Cloning: A Laboratory Manual*, Third Edition, Cold Spring Harbor Laboratory Press, Cold Spring Harbor, N.Y., 2001.

Sato et al., "Cytoplasmic membrane-associated protein (CAP) isolated from *Streptococcus* pyrogenes: as a new bacterial superantigen," *Microbiol. Immunol.*, 38(2):139-147, 1994.

Saunders and Moxon, "Implications of Sequencing Bacterial Genomes for Pathogenesis and Vaccine Development," *Current Opinion in Biotechnology*, 9:618-623, 1998.

Schwab et al., "Superantigen can reactivate bacterial cell wall-induced arthritis," *J. Immunol.*, 150(9):4151-4159, 1993.

Singh, Wu, Barry, "Generation of Genome-WideCD8 T Cell Responses in HLA-A*0201 Transgenic Mice by an HIV-1 Ubiquitin Expression Library Immunization Vaccine," *J. Immunol.*, 168:379-391, 2002.

Smooker, Setiady, Rainczuk, Spithill, "Expression Library Immunization Protects Mice Against A Challenge with Virulent Rodent Malaria," *Vaccine*, 18:2533-2540, 2000.

Stevens, "Current Concepts: Coccidioidomycosis," *N. Eng. J. Med.*, 332:1077-1082, 1995.

Sykes and Johnston, "Linear Expression Elements: A Rapid, in vivo, Method to Screen for Gene Functions," *Nature Biotechnol.*, 17:355-359, 1999.

Sykes, Lewis, Squires, Johnston, "Evaluation of SIV Library Vaccines with Genetic Cytokines in a Macaque Challenge," *Vaccine*, 20:2382-2395, 2002.

Takada et al., "Molecular and Structural Requirements of a Lipoteichoic Acid from *Enterococcus hirae* ATCC 9790 for Cytokine-Inducing, Antitumor, and Antigenic Activities," *Infection and Immunity*, 63(1):57-65, 1995.

Tang et al., *Nature*, 356:152-154, 1992.

Ulmer et al., "Heterologous Protection Against Influenza by Injection of DNA Encoding a Viral Protein," *Science*, 259:1745-1749, 1993.

Vosika et al., *Cancer Immunol. Immunother.*, 18:107, 1984.

Wang et al., *Proc. Natl. Acad. Sci. USA*, 90:4156-4160, 1993.

Weinberger et al., *Science*, 228:740-742, 1985.

Whitton et al., *J. Virol.* 67:(1)348-352, 1993.

Wolf et al., "An Integrated Family of Amino Acid Sequence Analysis Programs," *Comput. Appl. Biosci.*, 4(1):187-191, 1988.

Wunderlich, Moura, Del Portillo, "Genetic Immunization of BALB/c Mice with a Plasmid Bearing the Gene Coding for a Hybrid Merozoite Surface Protein 1-Hepatitis B Virus Surface Protein Fusion Protects Mice against Lethal *Plasmodium Chabaudi Chabaudi* PCI Infection," *Infect. Immun.*, 68(10):5839-5845, 2000.

Yamamoto et al., "In vitro Augmentation of Natural Killer Cell Activity and Production of Interferon-α/β and -γ with Deoxyribonucleic Acid Fraction from *Mycobacterium bovis* BCG," *Jpn. J. Cancer Res.*, 79:866-873, 1988.

Yin et al., "Effect of Various Adjuvants on the Antibody Response of Mice to Pneumococcal Polysaccharides," *J. Biological Response Modifiers*, 8:190-205, 1989.

Yu, Smithson, Thomas, Kirkland, Cole, "Isolation and characterization of the urease gene (URE) from the pathogenic fungus *Coccidioides immitis*," *Gene*, 198(1-2):387-91, 1997.

Zhu, Yang, Magee, Cox, "Molecular cloning and characterization of *Coccidioides immitis* Antigen 2 cDNA," *Infect. Immun.*, 64(7):2695-2699, 1996.

Zhu, Tryon, Magee, Cox, "Identification of a *Coccidioides immitis* Antigen 2 domain that expresses B-cell-reactive epitopes," *Infect. Immun.*, 65:3376-3380, 1997.

Zimmermann, Johnson, Martens, White, Zimmer, Pappagianis, "Protection Against Lethal Murine Coccidioidomycosis by a Soluble Vaccine from Spherules," *Infect. Immun.*, 66(5):2342-2345, 1998.

What is claimed is:

1. A purified protein that comprises the amino acid sequence of amino acids 20-224 of SEQ ID NO:2.

2. A purified protein that comprises the amino acid sequence of SEQ ID NO:2.

3. The protein of claim 2, wherein said protein consists of the amino acid sequence of SEQ ID NO:2.

4. A composition comprising the protein of claim 1 in a pharmaceutically acceptable carrier or diluent.

5. A composition comprising the protein of claim 2 in a pharmaceutically acceptable carrier or diluent.

6. A composition comprising the protein of claim 3 in a pharmaceutically acceptable carrier or diluent.

7. The composition of claim 4, further comprising an adjuvant.

8. The composition of claim 5, further comprising an adjuvant.

9. The composition of claim 6, further comprising an adjuvant.

* * * * *

UNITED STATES PATENT AND TRADEMARK OFFICE
CERTIFICATE OF CORRECTION

PATENT NO.         : 7,342,101 B1
APPLICATION NO. : 10/985853
DATED                  : March 11, 2008
INVENTOR(S)         : Cox et al.

It is certified that error appears in the above-identified patent and that said Letters Patent is hereby corrected as shown below:

On the title page Item 54; and Column 1, line 3: Please correct title:
"COCCIDIODES" To read -- COCCIDIOIDES --

On the title page Item 56: References Cited, Other Publications:
Please correct the publications to read as follows:
  -- Billetta et al., "identification of a Novel Antigen from *Coccidioides Immitis* Using Immuno-Based Functional Genomic Methods," *The Midwinter Conference of Immunologists*, Jan. 22-25, 2000. --

-- Corry et al., "Cytokine Production by Peripheral Blood Mononuclear Cells in Human Coccidioidomycosis," *J. Infect. Dis.*, 174:440-443, 1996. --

-- Cox and Magee, "*Coccidioidomycosis*: Host Response and Vaccine Development," *Clin. Microbiol. Rev.*, 17(4):804-839, 2004. --

-- Li et al., "Recombinant Urease and Urease DNA of *Coccidioidomycosis Immitis* Elicit and Immunoproteactive Response Against *Coccidioidomycosis* in Mice," *Infect Immun.*, 69(5):2878-87, 2001 --

Signed and Sealed this

Twenty-fourth Day of June, 2008

JON W. DUDAS
*Director of the United States Patent and Trademark Office*

SEQUENCE LISTING

<160> NUMBER OF SEQ ID NOS: 23

<210> SEQ ID NO 1
<211> LENGTH: 1080
<212> TYPE: DNA
<213> ORGANISM: Coccidioides immitis

<400> SEQUENCE: 1

```
ggcacgaggg taaagtaaac catcgaaggg atagcataca ttttcaaccg cattctcttt     60
ttactctcac cttcccaaaa gtaatcgtcc acctcgttga agcggtctgc agagcaccag    120
agagtctctc aaagcaacca caatgcatct ctcaggaata gtctttgcgt tcagtgctct    180
catttccctc tccacagccc atttcaggct ggttgacccg ccacccagag gtttttcgga    240
ggacatgctc actaggttcc cttgcggcgg ccaatcaatg tccaagtccc gtaccagcgt    300
ttccttaacc gatctcgaga tgcccatcgc attggagatg ggccatgatc agacagctgt    360
gcaggtatta ttggcgctgg gcagccaccc gggatcgaac ttcaacatca ccttggtgcc    420
gacatttagg caagttgggc tgggagactt ttgcttgcca tctgttagct tagatgagca    480
gcgtctgggt gtgaagccgg tagatgggat gaatgccacg ctgcaggtcg tgacaaacgg    540
agacccaaat ggtggattgt ataattgcgc cgatatcacg ttctcttcca caacggagta    600
taccgttccc agcagctgca aaaacggcac cggagtcgcg gccacgccat tctcgggaga    660
agcagcaaca cgtaatgcaa acgagtccac gccgaacgga cagccgcaac gtggcaactc    720
tggatctgga ccaacatcga atatagctgg tcatttggag acagctacct ggggagtttt    780
aggcgcaatt gttgtagggg gtgttgcgtt gctataagag aggccagccg gtcccttctg    840
ggttatgggt aaaagctcat ccaaatcagt aggtagcaag tgctatcttg tttttatgaa    900
ctggaaatcc aaaagctttg gagttgggtt ggacaggtga aggtatgtat gtatgtacat    960
atatatatac cctgtctaat tatggggcga tcaacaatat agatcttttc agcaccattg   1020
gaaaaaaaaa aaaaaaaaaa aaaaaaaaaa aaaaaaaaaa aaaaaaaaaa aaaaaaaaaa   1080
```

<210> SEQ ID NO 2
<211> LENGTH: 224
<212> TYPE: PRT
<213> ORGANISM: Coccidioides immitis

<400> SEQUENCE: 2

```
Met His Leu Ser Gly Ile Val Phe Ala Phe Ser Ala Leu Ile Ser Leu
1               5                   10                  15

Ser Thr Ala His Phe Arg Leu Val Asp Pro Pro Pro Arg Gly Phe Ser
            20                  25                  30

Glu Asp Met Leu Thr Arg Phe Pro Cys Gly Gly Gln Ser Met Ser Lys
        35                  40                  45

Ser Arg Thr Ser Val Ser Leu Thr Asp Leu Glu Met Pro Ile Ala Leu
    50                  55                  60

Glu Met Gly His Asp Gln Thr Ala Val Gln Val Leu Leu Ala Leu Gly
65                  70                  75                  80

Ser His Pro Gly Ser Asn Phe Asn Ile Thr Leu Val Pro Thr Phe Arg
                85                  90                  95

Gln Val Gly Leu Gly Asp Phe Cys Leu Pro Ser Val Ser Leu Asp Glu
            100                 105                 110

Gln Arg Leu Gly Val Lys Pro Val Asp Gly Met Asn Ala Thr Leu Gln
        115                 120                 125
```

```
Val Val Thr Asn Gly Asp Pro Asn Gly Gly Leu Tyr Asn Cys Ala Asp
    130                 135                 140

Ile Thr Phe Ser Ser Thr Thr Glu Tyr Thr Val Pro Ser Ser Cys Lys
145                 150                 155                 160

Asn Gly Thr Gly Val Ala Ala Thr Pro Phe Ser Gly Glu Ala Ala Thr
                165                 170                 175

Arg Asn Ala Asn Glu Ser Thr Pro Asn Gly Gln Pro Gln Arg Gly Asn
            180                 185                 190

Ser Gly Ser Gly Pro Thr Ser Asn Ile Ala Gly His Leu Glu Thr Ala
        195                 200                 205

Thr Trp Gly Val Leu Gly Ala Ile Val Val Gly Gly Val Ala Leu Leu
    210                 215                 220

<210> SEQ ID NO 3
<211> LENGTH: 23
<212> TYPE: PRT
<213> ORGANISM: ARTIFICIAL
<220> FEATURE:
<223> OTHER INFORMATION: SYNTHETIC PEPTIDE

<400> SEQUENCE: 3

Ser Gly Ile Val Phe Ala Phe Ser Ala Leu Ile Ser Leu Ser Thr Ala
1               5                   10                  15

His Phe Arg Leu Val Asp Pro
            20

<210> SEQ ID NO 4
<211> LENGTH: 7
<212> TYPE: PRT
<213> ORGANISM: ARTIFICIAL
<220> FEATURE:
<223> OTHER INFORMATION: SYNTHETIC PEPTIDE

<400> SEQUENCE: 4

Thr Arg Phe Pro Cys Cys Gly
1               5

<210> SEQ ID NO 5
<211> LENGTH: 7
<212> TYPE: PRT
<213> ORGANISM: ARTIFICIAL
<220> FEATURE:
<223> OTHER INFORMATION: SYNTHETIC PEPTIDE

<400> SEQUENCE: 5

Ser Arg Thr Ser Val Ser Leu
1               5

<210> SEQ ID NO 6
<211> LENGTH: 13
<212> TYPE: PRT
<213> ORGANISM: ARTIFICIAL
<220> FEATURE:
<223> OTHER INFORMATION: SYNTHETIC PEPTIDE

<400> SEQUENCE: 6

Asp Gln Thr Ala Val Gln Val Leu Leu Ala Leu Gly Ser
1               5                   10

<210> SEQ ID NO 7
<211> LENGTH: 24
<212> TYPE: PRT
<213> ORGANISM: ARTIFICIAL
```

```
<220> FEATURE:
<223> OTHER INFORMATION: SYNTHETIC PEPTIDE

<400> SEQUENCE: 7

Asn Ile Thr Leu Val Pro Thr Arg Phe Gln Val Gly Leu Gly Asp Phe
1               5                   10                  15

Cys Leu Pro Ser Val Ser Leu Asp
            20

<210> SEQ ID NO 8
<211> LENGTH: 7
<212> TYPE: PRT
<213> ORGANISM: ARTIFICIAL
<220> FEATURE:
<223> OTHER INFORMATION: SYNTHETIC PEPTIDE

<400> SEQUENCE: 8

Gln Arg Leu Gly Val Lys Pro
1               5

<210> SEQ ID NO 9
<211> LENGTH: 7
<212> TYPE: PRT
<213> ORGANISM: ARTIFICIAL
<220> FEATURE:
<223> OTHER INFORMATION: SYNTHETIC PEPTIDE

<400> SEQUENCE: 9

Ala Thr Leu Gln Val Val Thr
1               5

<210> SEQ ID NO 10
<211> LENGTH: 8
<212> TYPE: PRT
<213> ORGANISM: ARTIFICIAL
<220> FEATURE:
<223> OTHER INFORMATION: SYNTHETIC PEPTIDE

<400> SEQUENCE: 10

Gly Leu Tyr Asn Cys Ala Asp Ile
1               5

<210> SEQ ID NO 11
<211> LENGTH: 8
<212> TYPE: PRT
<213> ORGANISM: ARTIFICIAL
<220> FEATURE:
<223> OTHER INFORMATION: SYNTHETIC PEPTIDE

<400> SEQUENCE: 11

Thr Glu Tyr Thr Val Pro Ser Ser
1               5

<210> SEQ ID NO 12
<211> LENGTH: 12
<212> TYPE: PRT
<213> ORGANISM: ARTIFICIAL
<220> FEATURE:
<223> OTHER INFORMATION: SYNTHETIC PEPTIDE

<400> SEQUENCE: 12

Thr Trp Gly Val Leu Gly Ala Ile Val Val Gly Gly
1               5                   10

<210> SEQ ID NO 13
<211> LENGTH: 9
```

```
<212> TYPE: PRT
<213> ORGANISM: ARTIFICIAL
<220> FEATURE:
<223> OTHER INFORMATION: SYNTHETIC PEPTIDE

<400> SEQUENCE: 13

Gly Ser Asn Phe Asn Ile Thr Leu Val
1               5

<210> SEQ ID NO 14
<211> LENGTH: 9
<212> TYPE: PRT
<213> ORGANISM: ARTIFICIAL
<220> FEATURE:
<223> OTHER INFORMATION: SYNTHETIC PEPTIDE

<400> SEQUENCE: 14

Ser Ser Cys Lys Asn Gly Thr Gly Val
1               5

<210> SEQ ID NO 15
<211> LENGTH: 9
<212> TYPE: PRT
<213> ORGANISM: ARTIFICIAL
<220> FEATURE:
<223> OTHER INFORMATION: SYNTHETIC PEPTIDE

<400> SEQUENCE: 15

Gly Gly Leu Tyr Asn Cys Ala Asp Ile
1               5

<210> SEQ ID NO 16
<211> LENGTH: 9
<212> TYPE: PRT
<213> ORGANISM: ARTIFICIAL
<220> FEATURE:
<223> OTHER INFORMATION: SYNTHETIC PEPTIDE

<400> SEQUENCE: 16

Ala Ala Thr Arg Asn Ala Asn Glu Ser
1               5

<210> SEQ ID NO 17
<211> LENGTH: 9
<212> TYPE: PRT
<213> ORGANISM: ARTIFICIAL
<220> FEATURE:
<223> OTHER INFORMATION: SYNTHETIC PEPTIDE

<400> SEQUENCE: 17

Phe Ser Ser Thr Thr Glu Tyr Thr Val
1               5

<210> SEQ ID NO 18
<211> LENGTH: 9
<212> TYPE: PRT
<213> ORGANISM: ARTIFICIAL
<220> FEATURE:
<223> OTHER INFORMATION: SYNTHETIC PEPTIDE

<400> SEQUENCE: 18

Phe Ser Ala Leu Ile Ser Leu Ser Thr
1               5

<210> SEQ ID NO 19
<211> LENGTH: 9
<212> TYPE: PRT
```

```
<213> ORGANISM: ARTIFICIAL
<220> FEATURE:
<223> OTHER INFORMATION: SYNTHETIC PEPTIDE

<400> SEQUENCE: 19

Phe Ser Ser Thr Thr Glu Tyr Thr Val
1               5

<210> SEQ ID NO 20
<211> LENGTH: 9
<212> TYPE: PRT
<213> ORGANISM: ARTIFICIAL
<220> FEATURE:
<223> OTHER INFORMATION: SYNTHETIC PEPTIDE

<400> SEQUENCE: 20

Phe Ser Gly Glu Ala Ala Thr Arg Asn
1               5

<210> SEQ ID NO 21
<211> LENGTH: 9
<212> TYPE: PRT
<213> ORGANISM: ARTIFICIAL
<220> FEATURE:
<223> OTHER INFORMATION: SYNTHETIC PEPTIDE

<400> SEQUENCE: 21

Val Gln Val Leu Leu Ala Leu Gly Ser
1               5

<210> SEQ ID NO 22
<211> LENGTH: 9
<212> TYPE: PRT
<213> ORGANISM: ARTIFICIAL
<220> FEATURE:
<223> OTHER INFORMATION: SYNTHETIC PEPTIDE

<400> SEQUENCE: 22

Met Ser Lys Ser Arg Thr Ser Val Ser
1               5

<210> SEQ ID NO 23
<211> LENGTH: 50
<212> TYPE: DNA
<213> ORGANISM: ARTIFICIAL
<220> FEATURE:
<223> OTHER INFORMATION: SYNTHETIC OLIGONUCLEOTIDE

<400> SEQUENCE: 23
gagagagaga gagagagaga actagtctcg agttttttttt tttttttttt          50
```